(12) United States Patent
Fuqua et al.

(10) Patent No.: US 7,429,650 B2
(45) Date of Patent: Sep. 30, 2008

(54) METHODS AND COMPOSITIONS IN BREAST CANCER DIAGNOSIS AND THERAPEUTICS

(75) Inventors: Suzanne Fuqua, Sugar Land, TX (US);
Peter O'Connell, Houston, TX (US); D. Craig Allred, Houston, TX (US);
Torsten A. Hopp, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 372 days.

(21) Appl. No.: 10/437,107

(22) Filed: May 13, 2003

(65) Prior Publication Data

US 2003/0186313 A1 Oct. 2, 2003

Related U.S. Application Data

(62) Division of application No. 10/052,092, filed on Jan. 18, 2002, now Pat. No. 6,821,732.

(60) Provisional application No. 60/304,018, filed on Jul. 9, 2001, provisional application No. 60/262,990, filed on Jan. 19, 2001.

(51) Int. Cl.
*C07H 21/04* (2006.01)
(52) U.S. Cl. .................... 536/23.1; 536/24.31; 536/24.3
(58) Field of Classification Search ........................ None
See application file for complete search history.

(56) References Cited

U.S. PATENT DOCUMENTS 5,563,035 A 10/1996 Weigel 6,162,606 A 12/2000 Raam
2003/0207380 A1 * 11/2003 Saito et al. .................. 435/69.1

FOREIGN PATENT DOCUMENTS

WO    WO 95/11995    * 5/1995
WO    WO/99/58675    * 11/1999

OTHER PUBLICATIONS

Garcia et al. (PNAS USA 1992, vol. 89, pp. 11538-11542).*
GenBank record NM_018086, *Homo sapiens* fidgetin (FIGN) mRNA, Nov. 18, 2006.*
GenBank record AF173235, *Polyxenus fasciculatus* 18S ribosomal RNA gene, Nov. 4, 2005.*
GenBank record X90668, *P. lagurus* gene for 18S ribosomal RNA, Jun. 6, 2003.*
Cox et al. Nature Genetics, vol. 26, Oct. 2000, pp. 198-202.*
GenBank record AF184588, *Jonopsidium acaule* LEAFY protein (LEAFY1) gene, Oct. 1, 1999.*
American Journal of Botany 87(5):634-641, 2000.*

(Continued)

*Primary Examiner*—Juliet C Switzer
(74) *Attorney, Agent, or Firm*—Fulbright & Jaworski, LLP

(57) ABSTRACT

The present invention is directed to compositions regarding a specific mutation in estrogen receptor alpha and their use as diagnostic markers in breast tissue, such as premalignant lesions, for the development of breast cancer. More specifically, cells of breast cancer whose nucleic acid comprises the estrogen receptor alpha mutation identify the breast cancer to be an invasive breast cancer.

10 Claims, 9 Drawing Sheets

OTHER PUBLICATIONS

Greene et al. (Science 231 (4742) 1150-1154 (1986)).*
Burstein, Nelson A.; Overall Principles of Cancer Management—Hormone Therapy; published in Cancer, A Manual for Practitioners (American Cancer Society Massachusetts Division); 6th Edition, 1982, pp. 67-71.
Donegan, William L.; Prognostic Factors; Cancer 1992; 70:1755-1764.
Brooks, S. C., et al.; Relation of Tumor Content of Estrogen and Progesterone Receptors with Response of Patient to Endocrine Therapy; Cancer 46:2775-2778, 1980.
Degenshein, George A., et al.; The Value of Progesterone Receptor Assays in the Management of Advanced Breast Cancer; Cancer 46:2789-2793, 1980.
Fuqua, Suzanne A. W., et al.; Variant Human Breast Tumor Estrogen Receptor with Constitutive Transcriptional Activity; Cancer Research 51:105-109, Jan. 1, 1991.
Gelbfish, Gary A., et al.; Relationship of Estrogen and Progesterone Receptors to Prognosis in Breast Cancer; Ann Surg. 207(1):75-79, Jan. 1998.
Greene, Geoffrey, et al.; Sequence and Expression of Human Estrogen Receptor Complementary DNA; Science vol. 231, pp. 1150-1154: Mar. 7, 1986.
Kohail, Hanaa M., et al.; A Multifactorial Analysis of Steroid Hormone Receptors in Stages I and II Breast Cancer; Ann. Surg 201(5):611-617, May 1985.
Elledge, Richard M., et al.; Prognostic Factors and Therapeutic Decisions in Axillary Node-Negative Breast Cancer; Annu. Rev. Med. 1993, 44:201-210.
McGuire, William L.; Prognostic factors for recurrence and survival in human breast cancer; Breast Cancer Research and Treatment 10:5-9, 1987.
Millis, Rosemary R.; Correlation of Hormone Receptor with Pathological Features in Human Breast Cancer; Cancer 46:2869-2871, 1980.
McCarty, Kenneths, et al.; Correlation of Estrogen and Progesterone Receptors with Histologic Differentiation in Mammary Carcinoma; Cancer 46:2851-2858, 1980.
O'Connell, Peter, et al.; Loss of Heterozygosity at D14S62 and Metastatic Potential of Breast Cancer; Reports, Journal of the National Cancer Institute, vol. 91(16), pp. 1391-1397; Aug. 18, 1999.
Shousha, S., et al.; Oestrogen receptors in mucinous carcinoma of the breast: an immunohistological study using paraffin wax sections; J. Clin. Pathol. 1989; 42:902-905.
Shousha, S., et al.; Immunohistological study of oestrogen receptors in breast carcinomas that are biochemically receptor negative; J. Clin. Pathol. 1990; 43:239-242.
Williams, M. R., et al.; Oestrogen receptors in primary and advanced breast cancer: An eight year review of 704 cases; Br. J. Cancer (1987), 55:67-73.
Vogelstein, Bert, et al.; The multistep nature of cancer; TIG vol. 9 (4), pp. 138-141, Apr. 1993.
Weigel, Ronald, J., et al.; Transcriptional Control of Estrogen Receptor in Estrogen Receptor-negative Breast Carcinoma; Cancer Research, vol. 53 (15):3472-3474, Aug. 1, 1993.
Scott, Gary K., et al.; Truncated Forms of DNA-binding Estrogen Receptors in Human Breast Cancer; J. Clin. Invest. 1991, 88:700-706.
Ince, B. Avery, et al.; Powerful Dominant Negative Mutants of the Human Estrogen Receptor; The Journal of Biological Chemistry, vol. 268 (19), 14026-14032, 1993.
Fuqua, Suzanne A. W., et al.; Inhibition of Estrogen Receptor Action by a Naturally Occurring Variant in Human Breast Tumors; Cancer Research 52:483-486, Jan. 15, 1992.
Castles, Carl G., et al.; Expression of a Constitutively Active Estrogen Receptor Variant in the Estrogen Receptor-negative BT-20 Human Breast Cancer Cell Line: Cancer Research 53 (24):5934-5939, Dec. 15, 1993.
Keaveney, M., et al.; Evidence for a Previously Unidentified Upstream Exon in the Human Oestrogen Receptor Gene; J. Mol. Endocr., vol. 6:111-115, 1991.
Piva, R., et al.; Sequencing of an RNA Transcript of the Human Estrogen Receptor Gene: Evidence for a New Transcriptional Event; J. Steroid Biochem. Molec. Biol., 46 (5), pp. 531-538, 1993.
McDonnell, Donald P., The Molecular Pharmacology of SERMs, TEM, vol. 10 (8):301-311, 1999.
Barkhem, Tomas, et al.; Differential Response of Estrogen Receptor a and Estrogen Receptor B to Partial Estrogen Agonists/Antagonists; Molecular Pharmacology, 54:105-112, 1998.
Sun, Jun, et al.; Novel Ligands that Function as Selective Estrogens or Antiestrogens for Estrogen Receptor-a or Estrogen Receptor-B; Endocrinology, vol. 140 (2):800-804, 1999.
Barkhem, Tomas, et al.; Characterization of the "Estrogenicity" of Tamoxifen and Raloxifene in HepG2 Cells: Regulation of Gene Expression from an ERE Controlled Reporter Vector Versus Regulation of the Endogenous SHBG and PS2 Genes; J. Steroid Biochem. Molec. Biol., vol. 62 (1), pp. 53-64, 1997.
Cowley, Shaun, M., et al.; Estrogen Receptors a and B Form Heterodimers on DNA; The Journal of Biological Chemistry, vol. 272 (32), pp. 19858-19862, Aug. 8, 1997.
Paige, Lisa A., et al.; Estrogen receptor (ER) modulators each induce distinct conformational changes in ER a and ER B; Proc. Natl. Acad. Sci. USA, vol. 96, pp. 3999-4004, Mar. 1999.
Shiau, Andrew K., et al.; The Structural Basis of Estrogen Receptor/Coactivator Recognition and the Antagonism of This Interaction by Tamoxifen; Cell, vol. 95, pp. 927-937, Dec. 28, 1998.
Cowley, Shaun M., et al.; A comparison of transcriptional activation by ERa and ERB; Journal of Steroid Biochemistry and Molecular Biology, vol. 69, pp. 165-175, 1999.
Tremblay, Gilles B., et al.; Cloning, Chromosomal Localization, and Functional Analysis of the Murine Estrogen Receptor B; Molecular Endocrinology 11:353-365, 1997.
Witkowska, H. Ewa, et al.; Characterization of bacterially expressed rat estrogen receptor B ligand binding domain by mass spectrometry; Structural comparison with estrogen receptor a; Steroids 62:621-631, 1997.
McGuire, William L., et al.; Estrogen Receptor Variants in Clinical Breast Cancer; Molecular Endocrinology 5:1571-1577, 1991.
van Agthoven, Ton, et al.; Differential Expression of Estrogen, Progesterone, and Epidermal Growth Factor Receptors in Normal, Benign, and Malignant Human Breast Tissues using Dual Staining Immunohistochemistry; American Journal of Pathology, vol. 144 (6), pp. 1238-1246, Jun. 1994.
Zhang, Ziu-Xia, et al.; An Estrogen Receptor Mutant with Strong Hormone-independent Activity from a Metastatic Breast Cancer; Cancer Research 57:1244-1249, Apr. 1, 1997.
Tremblay, Gilles B., et al.; Ligand-independent Activation of the Estrogen Receptors a and B by Mutations of a Conserved Tyrosine Can Be Abolished by Antiestrogens; Cancer Research 58:877-881, Mar. 1, 1998.
Anandappa, Shanez Y., et al.; Variant estrogen Receptor a mRNAs in Human Breast Cancer Specimens; Int. J. Cancer: 88, pp. 209-216, 2000.
Schuur, Eric R., et al.; Monoallelic Amplification of Estrogen Receptor-a Expression in Breast Cancer; Cancer Research 60, pp. 2598-2601, May 15, 2000.
Fasco, Michael J., et al.; Expression of an estrogen receptor alpha variant protein in cell lines and tumors; Molecular and Cellular Endocrinology 162, pp. 167-180, 2000.
Rost, Natalia S., et al.; Immunochemical analyses of estrogen receptors in human breast tumors by a novel monoclonal estrogen receptor antibody (EVG F9); Steroids 65, pp. 429-436, 2000.
O'Connell, Peter, et al.; Analysis of Loss of Heterozygosity in 399 Premalignant Breast Lesions at 15 Genetic Loci; Journal of the National Cancer Institute, vol. 90 (9), pp. 697-703; May 6, 1998.
Page, David L., et al.; Premalignant and Malignant Disease of the Breast: The Roles of the Pathologist; Mod Pathol 1998; 11(2):120-128.
Page, David L.; The Woman at High Risk for Breast Cancer—Importance of Hyperplasia; Special Problems in Breast Cancer Therapy, vol. 76(2), pp. 221-230, Apr. 1996.
Roger, Pascal, et al.; Dissociated Overexpression of Cathepsin D and Estrogen Receptor Alpha in Preinvasive Mammary Tumors; Human Pathology, vol. 31 (5), pp. 593-600, May 2000.

Lishman, S. C., et al.; Atypical lobular hyperplasia and lobular carcinoma in situ: surgical and molecular pathology; Histopathology 1999, 35, 195-200.

Page, David L., et al.; Evaluation and Management of High Risk and Premalignant Lesions of the Breast; World J. Surg. 18, 32-38, 1994.

Page, David L., et al.; Anatomic Markers of Human Premalignancy and Risk of Breast Cancer; Cancer 66:1326-1335, 1990.

Cardiff, R. D., et al.; Biology of Breast Preneoplasia; Cancer 39:2734-2746, 1977.

Stoll, B. A.; Premalignant Breast Lesions: Role for Biological Markers in Predicting Progression to Cancer; European Journal of Cancer, vol. 35 (5), pp. 693-697, 1999.

Slentz-Kesler, Kimberly, et al.; Identification of the Human Mnk2 Gene (MKNK2) through Protein Interaction with Estrogen Receptor B; Genomics 69, 63-71, 2000.

Dupont, William D., et al.; Risk Factors for Breast Cancer in Women with Proliferative Breast Disease; N. Engl. J. Med. 1985; 312:146-151.

Lakhani, Sunil R.; The Transition from Hyperplasia to Invasive Carcinoma of the Breast; Journal of Pathology, 187:272-278, 1998.

Allred, D. Craig, et al.; Biomarkers in Early Breast Neoplasia; Journal of Cellular Biochemistry; 17G:125-131 (1993).

Allred, D. Craig, et al; Immunohistochemical Studies of Early Breast Cancer Evolution; Breast Cancer Research and Treatment 32:13-18, 1994.

van't Veer, Laura J., et al.; Gene Expression Profiling Predicts Clinical Outcome of Breast Cancer; Nature, vol. 415, Jan. 31, 2002, pp. 530-536.

Solie, Therese, et al.; Gene Expression Patterns of Breast Carcinomas Distinguish Tumor Subclasses with Clinical Implications; PNAS, Sep. 11, 2001, vol. 98, No. 19, 10869-10874.

Sgroi, Dennis C., et al.; In Vivo Gene Expression Profile Analysis of Human Breast Cancer Progression; Cancer Research 59, 5656-5661, Nov. 15, 1999.

Perou, Charles M., et al; Distinctive Gene Expression Patterns in Human Mannary Epithelial Cells and Breast Cancer; Proc. Natl. Acad. Sci. USA, vol. 96, pp. 9212-9217, Aug. 1999.

Perou, Charles M., et al; Molecular Portraits of Human Breast Tumors; Nature, vol. 407, Aug. 17, 2000, pp. 747-752.

Fasco et al., "Gender-dependent expression of alpha and beta estrogen receptors in human nontumor and tumor lung tissue", Mol Cell Endocrinol; Feb. 25, 2002, 125-40; vol. 188.

Fujimoto et al., "Clinical Implications of the Expression of Estrogen Receptor- $\alpha$ and—$\beta$ in Primary and Metastatic Lesions of Uterine Endometrial Cancers"; Oncology; 2002; 269-277; vol. 62 (3).

Herynk et al., "Association between the Estrogen Receptor $\alpha$ A908G Mutation and Outcomes in Invasive Breast Cancer"; Clinical Cancer Research; Jun. 1, 2007; 3235-3243; vol. 13 (11).

Iwao et al., "Quantitative Analysis of Estrogen Receptor- $\alpha$ and—$\beta$ Messenger RNA Expression in Breast Carcinoma by Real-Time Polymerase Chain Reaction", Cancer; Oct. 15, 2000; 1732-1738; vol. 89 (8).

Koduri et al., "Quantitation of alternatively spliced estrogen receptor alpha mRNAs as separate gene populations"; Steroids; Jan. 1, 2001; 17-23(7); vol. 66 (1).

Mollerup et al., "Expression of estrogen receptors and $\beta$ in human lung tissue and cell lines"; Lung Cancer; Aug. 2002, 153-159(7); vol. 37(2).

Tyulmenkov et al., "Comparison of transcriptional synergy of estrogen receptors $\alpha$ and $\beta$ from multiple tandem estrogen response elements"; Molecular and Cellular Endocrinology, Jul. 25, 2000; 151-161(11); vol. 165 (1).

* cited by examiner 18 month old virgin mice – pH1b IHC

SEQUENCE LISTING

<160> NUMBER OF SEQ ID NOS: 49

<210> SEQ ID NO 1
<211> LENGTH: 6450
<212> TYPE: DNA
<213> ORGANISM: Human

<400> SEQUENCE: 1
gagttgtgcc tggagtgatg tttaagccaa tgtcagggca aggcaacagt ccctggccgt        60
cctccagcac ctttgtaatg catatgagct cgggagacca gtacttaaag ttggaggccc       120

```
gggagcccag gagctggcgg agggcgttcg tcctgggagc tgcacttgct ccgtcgggtc    180
gccggcttca ccggaccgca ggctcccggg gcagggccgg ggccagagct cgcgtgtcgg    240
cgggacatgc gctgcgtcgc ctctaacctc gggctgtgct cttttttccag gtggcccgcc   300
ggtttctgag ccttctgccc tgcggggaca cggtctgcac cctgcccgcg ccacggacc    360
atgaccatga ccctccacac caaagcatct gggatggccc tactgcatca gatccaaggg    420
aacgagctgg agcccctgaa ccgtccgcag ctcaagatcc cctggagcg ccccctgggc     480
gaggtgtacc tggacagcag caagcccgcc gtgtacaact accccgaggg cgccgcctac    540
gagttcaacg ccgcggccgc cgccaacgcg caggtctacg tcagaccgg cctcccctac     600
ggccccgggt ctgaggctgc ggcgttcggc tccaacggcc tgggggggttt cccccccactc  660
aacagcgtgt ctccgagccc gctgatgcta ctgcacccgc cgccgcagct gtcgcctttc    720
ctgcagcccc acggccagca ggtgccctac tacctggaga cgagcccag cggctacacg     780
gtgcgcgagg ccggcccgcc ggcattctac aggccaaatt cagataatcg acgccagggt    840
ggcagagaaa gattggccag taccaatgac aagggaagta tggctatgga atctgccaag    900
gagactcgct actgtgcagt gtgcaatgac tatgcttcag gctaccatta tggagtctgg    960
tcctgtgagg gctgcaaggc cttcttcaag agaagtattc aaggacataa cgactatatg   1020
tgtccagcca ccaaccagtg caccattgat aaaaacagga ggaagagctg ccaggcctgc   1080
cggctccgca aatgctacga agtgggaatg atgaaaggtg ggatacgaaa agaccgaaga   1140
ggagggagaa tgttgaaaca caagcgccag agagatgatg gggagggcag gggtgaagtg   1200
gggtctgctg gagacatgag agctgccaac ctttggccaa gcccgctcat gatcaaacgc   1260
tctaagaaga cagcctggc cttgtccctg acggccgacc agatggtcag tgccttgttg    1320
gatgctgagc cccccatact ctattccgag tatgatccta ccagacccttt cagtgaagct   1380
tcgatgatgg gcttactgac caacctggca gacagggagc tggttcacat gatcaactgg   1440
gcgaagaggg tgccaggctt tgtggatttg accctccatg atcaggtcca ccttctagaa   1500
tgtgcctggc tagagatcct gatgattggt ctcgtctggc gctccatgga gcacccagtg   1560
aagctactgt ttgctcctaa cttgctcttg gacaggaacc agggaaaatg tgtagagggc   1620
atggtggaga tcttcgacat gctgctggct acatcatctc ggttccgcat gatgaatctg   1680
cagggagagg agtttgtgtg cctcaaatct attattttgc ttaattctgg agtgtacaca   1740
tttctgtcca gcaccctgaa gtctctggaa gagaaggacc atatccaccg agtcctggac   1800
aagatcacag acactttgat ccacctgatg gccaaggcag gcctgaccct gcagcagcag   1860
caccagcggc tggcccagct cctcctcatc ctctcccaca tcaggcacat gagtaacaaa   1920
ggcatggagc atctgtacag catgaagtgc aagaacgtgg tgcccctcta tgacctgctg   1980
ctggagatgc tggacgccca ccgcctacat gcgcccacta gccgtggagg gcatccgtg    2040
gaggagacgg accaaagcca cttggccact gcgggctcta cttcatcgca ttccttgcaa   2100
aagtattaca tcacggggga ggcagagggt ttccctgcca cagtctgaga gctccctggc   2160
tcccacacgg ttcagataat ccctgctgca ttttaccctc atcatgcacc actttagcca   2220
aattctgtct cctgcataca ctccggcatg catccaacac caatggcttt ctagatgagt   2280
ggccattcat ttgcttgctc agttcttagt ggcacatctt ctgtcttctg ttgggaacag   2340
ccaaagggat tccaaggcta aatctttgta acagctctct ttcccccttg ctatgttact   2400
aagcgtgagg attcccgtag ctcttcacag ctgaactcag tctatgggtt ggggctcaga   2460
```

```
taactctgtg catttaagct acttgtagag acccaggcct ggagagtaga cattttgcct    2520
ctgataagca cttttttaaat ggctctaaga ataagccaca gcaaagaatt taaagtggct    2580
cctttaattg gtgacttgga gaaagctagg tcaagggttt attatagcac cctcttgtat    2640
tcctatggca atgcatcctt ttatgaaagt ggtacacctt aaagctttta tatgactgta    2700
gcagagtatc tggtgattgt caattcactt cccctatag gaatacaagg ggccacacag    2760
ggaaggcaga tcccctagtt ggccaagact tattttaact tgatacactg cagattcaga    2820
gtgtcctgaa gctctgcctc tggctttccg gtcatgggtt ccagttaatt catgcctccc    2880
atggacctat ggagagcaac aagttgatct tagttaagtc tccctatatg agggataagt    2940
tcctgatttt tgttttattt tttgtgttac aaaagaaagc cctccctccc tgaacttgca    3000
gtaaggtcag cttcaggacc tgttccagtg ggcactgtac ttggatcttc ccggcgtgtg    3060
tgtgccttac acaggggtga actgttcact gtggtgatgc atgatgaggg taaatggtag    3120
ttgaaaggag caggggccct ggtgttgcat ttagccctgg ggcatggagc tgaacagtac    3180
ttgtgcagga ttgttgtggc tactagagaa caagagggaa agtagggcag aaactggata    3240
cagttctgag cacagccaga cttgctcagg tggccctgca caggctgcag ctacctagga    3300
acattccttg cagaccccgc attgcctttg ggggtgccct gggatccctg gggtagtcca    3360
gctcttattc atttcccagc gtggccctgg ttggaagaag cagctgtcaa gttgtagaca    3420
gctgtgttcc tacaattggc ccagcaccct ggggcacggg agaagggtgg ggaccgttgc    3480
tgtcactact caggctgact ggggcctggt cagattacgt atgcccttgg tggtttagag    3540
ataatccaaa atcagggttt ggtttgggga agaaaatcct cccccttcct cccccgcccc    3600
gttccctacc gcctccactc ctgccagctc atttccttca atttcctttg acctataggc    3660
taaaaagaa aggctcattc cagccacagg gcagccttcc ctgggccttt gcttctctag    3720
cacaattatg ggttacttcc ttttcttaa caaaaagaa tgtttgattt cctctgggtg    3780
accttattgt ctgtaattga aaccctattg agaggtgatg tctgtgttag ccaatgaccc    3840
aggtagctgc tcgggcttct cttggtatgt cttgtttgga aaagtggatt tcattcattt    3900
ctgattgtcc agttaagtga tcaccaaagg actgagaatc tgggagggca aaaaaaaaa    3960
aaaaagtttt tatgtgcact taaatttggg gacaattta tgtatctgtg ttaaggatat    4020
gcttaagaac ataattcttt tgttgctgtt tgtttaagaa gcaccttagt ttgtttaaga    4080
agcaccttat atagtataat atatattttt ttgaaattac attgcttgtt tatcagacaa    4140
ttgaatgtag taattctgtt ctggatttaa tttgactggg ttaacatgca aaaaccaagg    4200
aaaaatattt agtttttttt ttttttttg tatacttttc aagctacctt gtcatgtata    4260
cagtcattta tgcctaaagc ctggtgatta ttcatttaaa tgaagatcac atttcatatc    4320
aacttttgta tccacagtag acaaaatagc actaatccag atgcctattg ttggatattg    4380
aatgacagac aatcttatgt agcaaagatt atgcctgaaa ggaaaatta ttcagggcag    4440
ctaattttgc ttttaccaaa atatcagtag taatattttt ggacagtagc taatgggtca    4500
gtgggttctt tttaatgttt atacttagat tttcttttaa aaaattaaa ataaaacaaa    4560
aaaaatttct aggactagac gatgtaatac cagctaaagc caaacaatta tacagtggaa    4620
ggttttacat tattcatcca atgtgttttct attcatgtta agatactact acatttgaag    4680
tgggcagaga acatcagatg attgaaatgt tcgcccaggg gtctccagca actttggaaa    4740
tctcttttgta ttttttacttg aagtgccact aatggacagc agatattttc tggctgatgt    4800
tggtattggg tgtaggaaca tgatttaaaa aaaaaactct tgcctctgct ttcccccact    4860
```

```
ctgaggcaag ttaaaatgta aaagatgtga tttatctggg gggctcaggt atggtgggga    4920
agtggattca ggaatctggg gaatggcaaa tatattaaga agagtattga aagtatttgg    4980
aggaaaatgg ttaattctgg gtgtgcacca aggttcagta gagtccactt ctgccctgga    5040
gaccacaaat caactagctc catttacagc catttctaaa atggcagctt cagttctaga    5100
gaagaaagaa caacatcagc agtaaagtcc atggaatagc tagtggtctg tgtttctttt    5160
cgccattgcc tagcttgccg taatgattct ataatgccat catgcagcaa ttatgagagg    5220
ctaggtcatc caaagagaag accctatcaa tgtaggttgc aaaatctaac ccctaaggaa    5280
gtgcagtctt tgatttgatt tccctagtaa ccttgcagat atgtttaacc aagccatagc    5340
ccatgccttt tgagggctga acaaataagg gacttactga taatttactt ttgatcacat    5400
taaggtgttc tcaccttgaa atcttataca ctgaaatggc cattgattta ggccactggc    5460
ttagagtact ccttcccctg catgacactg attacaaata cttcctatt catactttcc     5520 aattatgaga tggactgtgg gtactgggag tgatcactaa caccatagta atgtctaata    5580
ttcacaggca gatctgcttg gggaagctag ttatgtgaaa ggcaaataaa gtcatacagt    5640
agctcaaaag gcaaccataa ttctctttgg tgcaagtctt gggagcgtga tctagattac    5700
actgcaccat tcccaagtta atcccctgaa aacttactct caactggagc aaatgaactt    5760
tggtcccaaa tatccatctt ttcagtagcg ttaattatgc tctgtttcca actgcatttc    5820
ctttccaatt gaattaaagt gtggcctcgt tttagtcat ttaaaattgt tttctaagta     5880
attgctgcct ctattatggc acttcaattt tgcactgtct tttgagattc aagaaaaatt    5940
tctattcatt tttttgcatc caattgtgcc tgaactttta aaatatgtaa atgctgccat    6000
gttccaaacc catcgtcagt gtgtgtgttt agagctgtgc accctagaaa caacatactt    6060
gtcccatgag caggtgcctg agacacagac cctttgcat tcacagagag gtcattggtt     6120
atagagactt gaattaataa gtgacattat gccagtttct gttctctcac aggtgataaa    6180
caatgctttt tgtgcactac atactcttca gtgtagagct cttgttttat gggaaaaggc    6240
tcaaatgcca aattgtgttt gatggattaa tatgcccttt tgccgatgca tactattact    6300
gatgtgactc ggttttgtcg cagctttgct ttgtttaatg aaacacactt gtaaacctct    6360
tttgcacttt gaaaaagaat ccagcgggat gctcgagcac ctgtaaacaa ttttctcaac    6420
ctatttgatg ttcaaataaa gaattaaact                                    6450
```

<210> SEQ ID NO 2
<211> LENGTH: 1644
<212> TYPE: DNA
<213> ORGANISM: Artificial Sequence
<220> FEATURE:
<223> OTHER INFORMATION: Synthetic Estrogen Receptor Ligand Binding
      Domain Fusion

<400> SEQUENCE: 2

```
atggtgagca agggcgagga gctgttcacc ggggtggtgc ccatcctggt cgagctggac      60
ggcgacgtaa acggccacag gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
```

```
aagctggagt acaactacat cagccacaac gtctatatca ccgccgacaa gcagaagaac    480
ggcatcaagg cccacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgcccgcatg cccggagggt ctgctggaga catgagagct    720
gccaaccttt ggccaagccc gctcatgatc aaacgctcta agaagaacag cctggccttg    780
tccctgacgg ccgaccagat ggtcagtgcc ttgttggatg ctgagccccc catactctat    840
tccgagtatg atcctaccag acccttcagt gaagcttcga tgatgggctt actgaccaac    900
ctggcagaca gggagctggt tcacatgatc aactgggcga gagggtgcc aggctttgtg    960 gatttgaccc tccatgatca ggtccacctt ctagaatgtg cctggctaga gatcctgatg   1020
attggtctcg tctggcgctc catggagcac ccagtgaagc tactgtttgc tcctaacttg   1080
ctcttggaca ggaaccaggg aaaatgtgta gagggcatgg tggagatctt cgacatgctg   1140
ctggctacat catctcggtt ccgcatgatg aatctgcagg gagaggagtt tgtgtgcctc   1200
aaatctatta ttttgcttaa ttctggagtg tacacatttc tgtccagcac cctgaagtct   1260
ctggaagaga aggaccatat ccaccgagtc ctggacaaga tcacagacac tttgatccac   1320
ctgatggcca aggcaggcct gaccctgcag cagcagcacc agcggctggc ccagctcctc   1380
ctcatcctct cccacatcag gcacatgagt aacaaaggca tggagcatct gtacagcatg   1440
aagtgcaaga acgtggtgcc cctctatgac ctgctgctgg agatgctgga cgcccaccgc   1500
ctacatgcgc ccactagccg tggaggggca tccgtggagg agacggacca aagccacttg   1560
gccactgcgg gctctacttc atcgcattcc ttgcaaaagt attacatcac gggggaggca   1620
gagggtttcc ctgccacagt ctga                                          1644
```

<210> SEQ ID NO 3
<211> LENGTH: 1237
<212> TYPE: DNA
<213> ORGANISM: Human

<400> SEQUENCE: 3

```
tcctcccctg aatcagtttg tatgggctca ccaaagccta ctgttcaatt ttcaggagtt     60
ttgtaagcca tttgtcagac aagtggcctg aagtttgtta tggtggtggt atttacacca    120
tgaaaattgg catgttatgg tggtagtatt taccccatga aaactggtac aaattgaaat    180 cttttttcttc ttctcttgga gagccacttg ttgaacactt accagctcac ctgtgcttga    240
aagtatttct tcaaataaaa tgaaagctgg ttagctttga aaattttttg tctaaaagtt    300
tacacgggaa aaaaattaac taattttttt tttccacctg tgttttcagg gatacgaaaa    360
gaccgaagag gagggagaat gttgaaacac aagcgccaga gagatgatgg ggagggcagg    420
ggtgaagtgg ggtctgctgg agacatgaga gctgccaacc tttggccaag cccgctcatg    480
atcaaacgct ctaagaagaa cagcctggcc ttgtccctga cggccgacca gatggtcagt    540
gccttgttgg atgctgagcc cccatactc tattccgagt atgatcctac cagacccttc    600
agtgaagctt cgatgatggg cttactgacc aacctggcag acagggagct ggttcacatg    660
atcaactggg cgaagagggt gccaggtaag aatgcgaagc gcagctttta agagtcaata    720
gcttttcaag aacttgttgt gatgtcatgg gagaaatagt gggggaaaaa gaagcaataa    780
catgttatgt aattggtttc aaggttacag gagatgtgtt catttttcagt atcaatacac    840
```

```
tgtaattttc caggagatta ggaaataata tttttaaatc agaatctaga agactgaaat        900
tcttaaattg acataattta tttttaaccc atctcattta ccaaaaagat ttagggtgga        960
cactacatgg taaaactatt taatagtgta tgttcacagt agcagaaact tttaacacta       1020
aatgaactac aaaagtttgt aatattaatg acctttgttg aaaacatctc aattattaat       1080
caaacgattt tatcttaaaa agattttaa gattcggtgt ggtggctcgt gcctgtaatc        1140
ctagcacttt ttggggctga ggtgggagga ttgcttgagc caagagctt gaggaaagag        1200 aggacagcga ttctcgtacg aacggttacg attctga                                1237

<210> SEQ ID NO 4
<211> LENGTH: 392
<212> TYPE: DNA
<213> ORGANISM: Human

<400> SEQUENCE: 4
tcgaagagga gggagaatgt tgaagcacaa gcgccagaga gatgatgggg agggcagggg         60
tgaagtgggg tctgctggag acatgagagc tgccaacctt tggccaagcc cgctcatgat        120
caaacgctct aagaagaaca gcctggcctt gtccctgacg gccgaccaga tggtcagtgc        180
cttgttggat gctgagcccc ccatactcta ttccgagtat gatcctacca gacccttcag        240
tgaagcttcg atgatgggct tactgaccaa cctggcagac agggagctgg ttcacatgat        300
caactgggcg aagagggtgc caggaaccag ggaaaatgtg tagagggcat ggtggagatc        360
ttcgacatgc tgctggctac atcatctcgg tt                                      392

<210> SEQ ID NO 5
<211> LENGTH: 2106
<212> TYPE: DNA
<213> ORGANISM: Human

<400> SEQUENCE: 5
atgaccatga ccctccacac caaagcatct gggatggccc tactgcatca gatccaaggg         60
aacgagctgg agcccctgaa ccgtccgcag ctcaagatcc cctggagcg gcccctgggc         120 gaggtgtacc tggacagcag caagcccgcc gtgtacaact accccgaggg cgccgcctac        180
gagttcaacg ccgcggccgc cgccaacgcg caggtctacg gtcagaccgg cctcccctac        240
ggccccgggt ctgaggctgc ggcgttcggc tccaacggct gggggggttt ccccccactc        300
aacagcgtgt ctccgagccc gctgatgcta ctgcacccgc cgccgcagct gtcgcctttc        360
ctgcagcccc acggccagca ggtgccctac tacctggaga cgagcccag cggctacacg        420 gtgcgcgagg ccggcccgcc ggcattctac aggccaaatt cagataatcg acgccagggt        480
ggcagagaaa gattggccag taccaatgac aaggaagta tggctatgga atctgccaag        540
gagactcgct actgtgcagt gtgcaatgac tatgcttcag gctaccatta tggagtctgg        600
tcctgtgagg gctgcaaggc cttcttcaag agaagtattc aaggacataa cgactatatg        660
tgtccagcca ccaaccagtg caccattgat aaaaacagga ggaagagctg ccaggcctgc        720
cggctccgca atgctacgaa gtgggaatg atgaaaggtg ggatacgaaa agaccgaaga        780
ggagggagaa tgttgaaaca caagcgccag agagatgatg ggagggcag gggtgaagtg        840 gggtctgctg gagacatgag agctgccaac ctttggccaa gccgctcat gatcaaacgc        900 tctaagaaga acagcctggc cttgtccctg acggccgacc agatggtcag tgccttgttg        960
gatgctgagc cccccatact ctattccgag tatgatccta ccagaccctt cagtgaagct       1020
tcgatgatgg gcttactgac caacctggca gacagggagc tggttcacat gatcaactgg       1080
```

-continued

```
gcgaagaggg tgccaggctt tgtggatttg accctccatg atcaggtcca ccttctagaa   1140
tgtgcctggc tagagatcct gatgattggt ctcgtctggc gctccatgga gcacccagtg   1200
aagctactgt ttgctcctaa cttgctcttg gacaggaacc agggaaaatg tgtagagggc   1260
atggtggaga tcttcgacat gctgctggct acatcatctc ggttccgcat gatgaatctg   1320
cagggagagg agtttgtgtg cctcaaatct attattttgc ttaattctgg agtgtacaca   1380
tttctgtcca gcaccctgaa gtctctggaa gagaaggacc atatccaccg agtcctggac   1440
aagatcacag acactttgat ccacctgatg gccaaggcag gcctgaccct gcagcagcag   1500
caccagcggc tggcccagct cctcctcatc ctctcccaca tcaggcacat gaggaaccag   1560
ggaaaatgtg tagagggcat ggtggagatc ttcgacatgc tgctggctac atcatctcgg   1620
ttccgcatga tgaatctgca gggagaggag tttgtgtgcc tcaaatctat tattttgctt   1680
aattctggag tgtacacatt tctgtccagc accctgaagt ctctggaaga aaggaccat   1740 atccaccgag tcctggacaa gatcacagac actttgatcc acctgatggc caaggcaggc   1800
ctgaccctgc agcagcagca ccagcggctg gcccagctcc tcctcatcct ctcccacatc   1860
aggcacatga gtaacaaagg catggagcat ctgtacagca tgaagtgcaa gaacgtggtg   1920
cccctctatg acctgctgct ggagatgctg gacgccacc gcctacatgc gcccactagc   1980
cgtggagggg catccgtgga ggagacggac caaagccact tggccactgc gggctctact   2040
tcatcgcatt ccttgcaaaa gtattacatc acggggagg cagagggttt ccctgccaca   2100
gtctga                                                              2106
```

<210> SEQ ID NO 6
<211> LENGTH: 2092
<212> TYPE: DNA
<213> ORGANISM: Human

<400> SEQUENCE: 6

```
gaattccaaa attgtgatgt ttcttgtatt tttgatgaag gagaaatact gtaatgatca    60
ctgtttacac tatgtacact ttaggccagc cctttgtagc gttatacaaa ctgaaagcac   120
accggacccg caggctcccg gggcagggcc ggggccagag ctcgcgtgtc ggcgggacat   180
gcgctgcgtc gcctctaacc tcgggctgtg ctctttttcc aggtggcccg ccggtttctg   240
agccttctgc cctgcgggga cacggtctgc accctgcccg cggccacgga ccatgaccat   300
gaccctccac accaaagcat ctgggatggc cctactgcat cagatccaag gaacgagct    360 ggagcccctg aaccgtccgc agctcaagat ccccctggag cggcccctgg gcgaggtgta   420
cctggacagc agcaagcccg ccgtgtacaa ctaccccgag ggcgccgcct acagttcaa    480 cgccgcggcc gccgccaacg cgcaggtcta cggtcagacc ggcctcccct acggccccgg   540
gtctgaggct gcgcgttcg gctccaacgg cctgggggt ttcccccac tcaacagcgt     600 gtctccgagc ccgctgatgc tactgcaccc gccgccgcag ctgtcgcctt cctgcagcc    660 ccacggccag caggtgccct actacctgga gaacgagccc agcggctaca cggtgcgcga   720
ggccggcccg ccggcattct acaggccaaa ttcagataat cgacgccagg gtggcagaga   780
aagattggcc agtaccaatg acaagggaag tatggctatg aatctgcca aggagactcg   840 ctactgtgca gtgtgcaatg actatgcttc aggctaccat tatggagtct ggtcctgtga   900
gggctgcaag gccttcttca agagaagtat tcaaggacat aacgactata tgtgtccagc   960
caccaaccag tgcaccattg ataaaaacag gaggaagagc tgccaggcct gccggctccg   1020
```

```
caaatgctac gaagtgggaa tgatgaaagg tgggatacga aaagaccgaa gaggagggag    1080
aatgttgaaa cacaagcgcc agagagatga tggggagggc aggggtgaag tggggtctgc    1140
tggagacatg agagctgcca acctttggcc aagcccgctc atgatcaaac gctctaagaa    1200
gaacagcctg gccttgtccc tgacggccga ccagatggtc agtgccttgt tggatgctga    1260 gcccccata ctctattccg agtatgatcc taccagaccc ttcagtgaag cttcgatgat    1320
gggcttactg accaacctgg cagacaggga gctggttcac atgatcaact gggcgaagag    1380
ggtgccaggc tttgtggatt tgaccctcca tgatcaggtc caccttctag aatgtgcctg    1440
gctagagatc ctgatgattg gtctcgtctg gcgctccatg gagcacccag tgaagctact    1500
gtttgctcct aacttgctct tggacaggaa ccagggaaaa tgtgtagagg catggtgga    1560 gatcttcgac atgctgctgg ctacatcatc tcggttccgc atgatgaatc tgcagggaga    1620
ggagtttgtg tgcctcaaat ctattatttt gcttaattct ggagtgtaca catttctgtc    1680
cagcaccctg aagtctctgg aagagaagga ccatatccac cgagtcctgg acaagatcac    1740
agacactttg atccacctga tggccaaggc aggcctgacc ctgcagcagc agcaccagcg    1800
gctggcccag ctcctcctca tcctctccca catcaggcac atgagtaaca aaggcatgga    1860
gcatctgtac agcatgaagt gcaagaacgt ggtgcccctc tatgacctgc tgctggagat    1920
gctggacgcc caccgcctac atgcgcccac tagccgtgga ggggcatccg tggaggagac    1980
ggaccaaagc cacttggcca ctgcgggctc tacttcatcg cattccttgc aaaagtatta    2040
catcacgggg gaggcagagg gtttccctgc cacagtctga gagctccctg gc            2092

<210> SEQ ID NO 7
<211> LENGTH: 6450
<212> TYPE: DNA
<213> ORGANISM: Human

<400> SEQUENCE: 7
gagttgtgcc tggagtgatg tttaagccaa tgtcagggca aggcaacagt ccctggccgt      60
cctccagcac ctttgtaatg catatgagct cgggagacca gtacttaaag ttggaggccc     120
gggagcccag gagctggcgg agggcgttcg tcctgggagc tgcacttgct ccgtcgggtc     180
gccggcttca ccggaccgca ggctcccggg gcagggccgg ggccagagct cgcgtgtcgg     240
cgggacatgc gctgcgtcgc ctctaacctc gggctgtgct cttttttccag gtggcccgcc    300 ggtttctgag ccttctgccc tgcggggaca cggtctgcac cctgcccgcg gccacggacc     360
atgaccatga ccctccacac caaagcatct gggatggccc tactgcatca gatccaaggg    420
aacgagctgg agcccctgaa ccgtccgcag ctcaagatcc ccctggagcg gccccctgggc   480 gaggtgtacc tggacagcag caagcccgcc gtgtacaact accccgaggg cgccgcctac    540
gagttcaacg ccgcggccgc cgccaacgcg caggtctacg gtcagaccgg cctcccctac    600
ggcccccggg t ctgaggctgc ggcgttcggc tccaacggcc tggggggttt ccccccactc   660
aacagcgtgt ctccgagccc gctgatgcta ctgcacccgc cgccgcagct gtcgcctttc    720
ctgcagcccc acggccagca ggtgcccttc tacctggaga cgagcccag cggctacacg     780 gtgcgcgagg ccggccccgcc ggcattctac aggccaaatt cagataatcg acgcagggt    840 ggcagagaaa gattgccag taccaatgac aaggaagta tggctatgga atctgccaag     900
gagactcgct actgtgcagt gtgcaatgac tatgcttcag gctaccatta tggagtctgg    960
tcctgtgagg gctgcaaggc cttcttcaag agaagtattc aaggacataa cgactatatg     1020
tgtccagcca ccaaccagtg caccattgat aaaaacagga ggaagagctg ccaggcctgc   1080
```

```
cggctccgca aatgctacga agtgggaatg atgaaaggtg ggatacgaaa agaccgaaga    1140
ggagggagaa tgttgaaaca caagcgccag agagatgatg gggagggcag gggtgaagtg    1200
gggtctgctg gagacatgag agctgccaac ctttggccaa gcccgctcat gatcaaacgc    1260
tctaagaaga acagcctggc cttgtccctg acggccgacc agatggtcag tgccttgttg    1320
gatgctgagc cccccatact ctattccgag tatgatccta ccagacccct cagtgaagct    1380
tcgatgatgg gcttactgac caacctggca gacagggagc tggttcacat gatcaactgg    1440
gcgaagaggg tgccaggctt tgtggatttg accctccatg atcaggtcca ccttctagaa    1500
tgtgcctggc tagagatcct gatgattggt ctcgtctggc gctccatgga gcacccagtg    1560
aagctactgt ttgctcctaa cttgctcttg acaggaacc agggaaaatg tgtagagggc     1620
atggtggaga tcttcgacat gctgctggct acatcatctc ggttccgcat gatgaatctg    1680
cagggagagg agtttgtgtg cctcaaatct attattttgc ttaattctgg agtgtacaca    1740
tttctgtcca gcaccctgaa gtctctggaa gagaaggacc atatccaccg agtcctggac    1800
aagatcacag acactttgat ccacctgatg gccaaggcag gcctgaccct gcagcagcag    1860
caccagcggc tggcccagct cctcctcatc ctctcccaca tcaggcacat gagtaacaaa    1920
ggcatggagc atctgtacag catgaagtgc aagaacgtgg tgcccctcta tgacctgctg    1980
ctggagatgc tggacgccca ccgcctacat gcgcccacta gccgtggagg ggcatccgtg    2040
gaggagacgg accaaagcca cttggccact gcgggctcta cttcatcgca ttccttgcaa    2100
aagtattaca tcacggggga ggcagagggt ttccctgcca cagtctgaga gctccctggc    2160
tcccacacgg ttcagataat ccctgctgca ttttaccctc atcatgcacc actttagcca    2220
aattctgtct cctgcataca ctccggcatg catccaacac caatggcttt ctagatgagt    2280
ggccattcat ttgcttgctc agttcttagt ggcacatctt ctgtcttctg ttgggaacag    2340
ccaaagggat tccaaggcta aatctttgta acagctctct ttcccccttg ctatgttact    2400
aagcgtgagg attcccgtag ctcttcacag ctgaactcag tctatgggtt ggggctcaga    2460
taactctgtg catttaagct acttgtagag acccaggcct ggagagtaga cattttgcct    2520
ctgataagca cttttaaat ggctctaaga ataagccaca gcaaagaatt taaagtggct     2580
cctttaattg gtgacttgga gaaagctagg tcaagggttt attatagcac cctcttgtat    2640
tcctatggca atgcatcctt ttatgaaagt ggtacacctt aaagctttta tatgactgta    2700
gcagagtatc tggtgattgt caattcactt cccccctatag aatacaagg ggccacacag    2760
ggaaggcaga tcccctagtt ggccaagact tattttaact tgatacactg cagattcaga    2820
gtgtcctgaa gctctgcctc tggctttccg gtcatgggtt ccagttaatt catgcctccc    2880
atggacctat ggagagcaac aagttgatct tagttaagtc tccctatatg agggataagt    2940
tcctgatttt tgttttattt tttgtgttac aaaagaaagc cctccctccc tgaacttgca    3000
gtaaggtcag cttcaggacc tgttccagtg ggcactgtac ttggatcttc ccggcgtgtg    3060
tgtgccttac acaggggtga actgttcact gtggtgatgc atgatgaggg taaatggtag    3120
ttgaaaggag caggggccct ggtgttgcat ttagccctgg ggcatggagc tgaacagtac    3180
ttgtgcagga ttgttgtggc tactagagaa caagagggaa agtagggcag aaactggata    3240
cagttctgag cacagccaga cttgctcagg tggccctgca caggctgcag ctacctagga    3300
acattccttg cagaccccgc attgcctttg ggggtgccct gggatccctg ggtagtccca    3360
gctcttattc atttcccagc gtggccctgg ttggaagaag cagctgtcaa gttgtagaca    3420
```

```
gctgtgttcc tacaattggc ccagcaccct ggggcacggg agaagggtgg ggaccgttgc    3480
tgtcactact caggctgact ggggcctggt cagattacgt atgcccttgg tggtttagag    3540
ataatccaaa atcagggttt ggtttgggga agaaaatcct cccccttcct cccccgcccc    3600
gttccctacc gcctccactc ctgccagctc atttccttca atttcctttg acctataggc    3660 taaaaagaa aggctcattc cagccacagg gcagccttcc ctgggccttt gcttctctag    3720
cacaattatg ggttacttcc tttttcttaa caaaaagaa tgtttgattt cctctgggtg    3780
accttattgt ctgtaattga aaccctattg agaggtgatg tctgtgttag ccaatgaccc    3840
aggtagctgc tcgggcttct cttggtatgt cttgtttgga aaagtggatt tcattcattt    3900
ctgattgtcc agttaagtga tcaccaaagg actgagaatc tgggagggca aaaaaaaaa    3960 aaaaagtttt tatgtgcact taaatttggg gacaatttta tgtatctgtg ttaaggatat    4020
gcttaagaac ataattcttt tgttgctgtt tgtttaagaa gcaccttagt ttgtttaaga    4080
agcaccttat atagtataat atatatttt ttgaaattac attgcttgtt tatcagacaa    4140
ttgaatgtag taattctgtt ctggatttaa tttgactggg ttaacatgca aaaaccaagg    4200
aaaaatattt agttttttt tttttttttg tatacttttc aagctacctt gtcatgtata    4260
cagtcattta tgcctaaagc ctggtgatta ttcatttaaa tgaagatcac atttcatatc    4320
aacttttgta tccacagtag acaaaatagc actaatccag atgcctattg ttggatattg    4380
aatgacagac aatcttatgt agcaaagatt atgcctgaaa aggaaaatta ttcagggcag    4440
ctaattttgc ttttaccaaa atatcagtag taatattttt ggacagtagc taatgggtca    4500
gtgggttctt tttaatgttt atacttagat tttccttttaa aaaaattaaa ataaaacaaa    4560
aaaaatttct aggactagac gatgtaatac cagctaaagc caaacaatta tacagtggaa    4620
ggttttacat tattcatcca atgtgtttct attcatgtta agatactact acatttgaag    4680
tgggcagaga acatcagatg attgaaatgt tcgcccaggg gtctccagca actttggaaa    4740
tctctttgta ttttttacttg aagtgccact aatggacagc agatattttc tggctgatgt    4800
tggtattggg tgtaggaaca tgatttaaaa aaaaaactct tgcctctgct ttccccact    4860 ctgaggcaag ttaaaatgta aaagatgtga tttatctggg gggctcaggt atggtgggga    4920
agtggattca ggaatctggg gaatggcaaa tatattaaga agagtattga aagtatttgg    4980
aggaaaatgg ttaattctgg gtgtgcacca aggttcagta gagtccactt ctgccctgga    5040
gaccacaaat caactagctc catttacagc catttctaaa atggcagctt cagttctaga    5100
gaagaaagaa caacatcagc agtaaagtcc atggaatagc tagtggtctg tgtttctttt    5160
cgccattgcc tagcttgccg taatgattct ataatgccat catgcagcaa ttatgagagg    5220
ctaggtcatc caaagagaag acccctatcaa tgtaggttgc aaaatctaac ccctaaggaa    5280
gtgcagtctt tgatttgatt ccctagtaa ccttgcagat atgtttaacc aagccatagc    5340
ccatgccttt tgagggctga acaaataagg gacttactga taatttactt ttgatcacat    5400
taaggtgttc tcaccttgaa atcttataca ctgaaatggc cattgattta ggccactggc    5460
ttagagtact ccttcccctg catgacactg attacaaata ctttcctatt catactttcc    5520
aattatgaga tggactgtgg gtactgggag tgatcactaa caccatagta atgtctaata    5580
ttcacaggca gatctgcttg gggaagctag ttatgtgaaa ggcaaataaa gtcatacagt    5640
agctcaaaag gcaaccataa ttctctttgg tgcaagtctt gggagcgtga tctagattac    5700
actgcaccat tccaagttta atcccctgaa aacttactct caactggagc aaatgaactt    5760
tggtcccaaa tatccatctt ttcagtagcg ttaattatgc tctgtttcca actgcatttc    5820
```

-continued

```
ctttccaatt gaattaaagt gtggcctcgt ttttagtcat ttaaaattgt tttctaagta    5880
attgctgcct ctattatggc acttcaattt tgcactgtct tttgagattc aagaaaaatt    5940
tctattcatt tttttgcatc caattgtgcc tgaactttta aaatatgtaa atgctgccat    6000
gttccaaacc catcgtcagt gtgtgtgttt agagctgtgc accctagaaa caacatactt    6060
gtcccatgag caggtgcctg agacacagac ccctttgcat tcacagagag gtcattggtt    6120
atagagactt gaattaataa gtgacattat gccagtttct gttctctcac aggtgataaa    6180
caatgctttt tgtgcactac atactcttca gtgtagagct cttgttttat gggaaaaggc    6240
tcaaatgcca aattgtgttt gatggattaa tatgcccttt tgccgatgca tactattact    6300
gatgtgactc ggttttgtcg cagctttgct ttgtttaatg aaacacactt gtaaacctct    6360
tttgcacttt gaaaagaat ccagcgggat gctcgagcac ctgtaaacaa ttttctcaac     6420
ctatttgatg ttcaaataaa gaattaaact                                    6450
```

<210> SEQ ID NO 8
<211> LENGTH: 7
<212> TYPE: DNA
<213> ORGANISM: Artificial Sequence
<220> FEATURE:
<223> OTHER INFORMATION: Estrogen Response Element
<220> FEATURE:
<221> NAME/KEY: misc_feature
<222> LOCATION: (4)..(4)
<223> OTHER INFORMATION: N equals C or G

<400> SEQUENCE: 8 tgantca                                                              7

<210> SEQ ID NO 9
<211> LENGTH: 595
<212> TYPE: PRT
<213> ORGANISM: Human

<400> SEQUENCE: 9

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

```
Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
            210                 215                 220

Asn Gln Cys Thr Ile Asp Lys Asn Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
            290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
            450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590
```

Ala Thr Val
        595

<210> SEQ ID NO 10
<211> LENGTH: 547
<212> TYPE: PRT
<213> ORGANISM: Artificial Sequence
<220> FEATURE:
<223> OTHER INFORMATION: Synthetic Estrogen Receptor Ligand Binding
      Domain Fusion

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Arg Met Pro Gly Gly Ser Ala Gly Asp Met Arg Ala
225                 230                 235                 240

Ala Asn Leu Trp Pro Ser Pro Leu Met Ile Lys Arg Ser Lys Lys Asn
                245                 250                 255

Ser Leu Ala Leu Ser Leu Thr Ala Asp Gln Met Val Ser Ala Leu Leu
            260                 265                 270

Asp Ala Glu Pro Pro Ile Leu Tyr Ser Glu Tyr Asp Pro Thr Arg Pro
        275                 280                 285

Phe Ser Glu Ala Ser Met Met Gly Leu Leu Thr Asn Leu Ala Asp Arg
    290                 295                 300

Glu Leu Val His Met Ile Asn Trp Ala Lys Arg Val Pro Gly Phe Val
305                 310                 315                 320

Asp Leu Thr Leu His Asp Gln Val His Leu Leu Glu Cys Ala Trp Leu
                325                 330                 335

Glu Ile Leu Met Ile Gly Leu Val Trp Arg Ser Met Glu His Pro Val
            340                 345                 350

Lys Leu Leu Phe Ala Pro Asn Leu Leu Asp Arg Asn Gln Gly Lys
              355                 360                 365

Cys Val Glu Gly Met Val Glu Ile Phe Asp Met Leu Leu Ala Thr Ser
        370                 375                 380

Ser Arg Phe Arg Met Met Asn Leu Gln Gly Glu Glu Phe Val Cys Leu
385                 390                 395                 400

Lys Ser Ile Ile Leu Leu Asn Ser Gly Val Tyr Thr Phe Leu Ser Ser
                405                 410                 415

Thr Leu Lys Ser Leu Glu Glu Lys Asp His Ile His Arg Val Leu Asp
            420                 425                 430

Lys Ile Thr Asp Thr Leu Ile His Leu Met Ala Lys Ala Gly Leu Thr
        435                 440                 445

Leu Gln Gln Gln His Gln Arg Leu Ala Gln Leu Leu Leu Ile Leu Ser
    450                 455                 460

His Ile Arg His Met Ser Asn Lys Gly Met Glu His Leu Tyr Ser Met
465                 470                 475                 480

Lys Cys Lys Asn Val Val Pro Leu Tyr Asp Leu Leu Leu Glu Met Leu
                485                 490                 495

Asp Ala His Arg Leu His Ala Pro Thr Ser Arg Gly Gly Ala Ser Val
            500                 505                 510

Glu Glu Thr Asp Gln Ser His Leu Ala Thr Ala Gly Ser Thr Ser Ser
        515                 520                 525

His Ser Leu Gln Lys Tyr Tyr Ile Thr Gly Glu Ala Glu Gly Phe Pro
    530                 535                 540

Ala Thr Val
545

<210> SEQ ID NO 11
<211> LENGTH: 113
<212> TYPE: PRT
<213> ORGANISM: human

<400> SEQUENCE: 11

Arg Arg Gly Gly Arg Met Leu Lys His Lys Arg Gln Arg Asp Asp Gly
1               5                   10                  15

Glu Gly Arg Gly Glu Val Gly Ser Ala Gly Asp Met Arg Ala Ala Asn
            20                  25                  30

Leu Trp Pro Ser Pro Leu Met Ile Lys Arg Ser Lys Lys Asn Ser Leu
        35                  40                  45

Ala Leu Ser Leu Thr Ala Asp Gln Met Val Ser Ala Leu Leu Asp Ala
    50                  55                  60

Glu Pro Pro Ile Leu Tyr Ser Glu Tyr Asp Pro Thr Arg Pro Phe Ser
65                  70                  75                  80

Glu Ala Ser Met Met Gly Leu Leu Thr Asn Leu Ala Asp Arg Glu Leu
                85                  90                  95

Val His Met Ile Asn Trp Ala Lys Arg Val Pro Gly Thr Arg Glu Asn
            100                 105                 110

Val

<210> SEQ ID NO 12
<211> LENGTH: 701
<212> TYPE: PRT
<213> ORGANISM: human

<400> SEQUENCE: 12

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
                35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Phe Gly Ser Asn Gly Leu Gly Gly
                85                  90                  95

Phe Pro Pro Leu Asn Ser Val Ser Pro Ser Leu Met Leu Leu His
                100                 105                 110

Pro Pro Pro Gln Leu Ser Pro Phe Leu Gln Pro His Gly Gln Gln Val
                115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
        340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
        370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
```

-continued

```
                420             425             430
Ser Arg Phe Arg Met Met Asn Leu Gln Gly Glu Glu Phe Val Cys Leu
            435                 440                 445
Lys Ser Ile Ile Leu Leu Asn Ser Gly Val Tyr Thr Phe Leu Ser Ser
        450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                    485                 490                 495
Leu Gln Gln Gln His Gln Arg Leu Ala Gln Leu Leu Ile Leu Ser
            500                 505                 510
His Ile Arg His Met Arg Asn Gln Gly Lys Cys Val Glu Gly Met Val
        515                 520                 525
Glu Ile Phe Asp Met Leu Leu Ala Thr Ser Ser Arg Phe Arg Met Met
        530                 535                 540
Asn Leu Gln Gly Glu Glu Phe Val Cys Leu Lys Ser Ile Ile Leu Leu
545                 550                 555                 560
Asn Ser Gly Val Tyr Thr Phe Leu Ser Ser Thr Leu Lys Ser Leu Glu
                565                 570                 575
Glu Lys Asp His Ile His Arg Val Leu Asp Lys Ile Thr Asp Thr Leu
            580                 585                 590
Ile His Leu Met Ala Lys Ala Gly Leu Thr Leu Gln Gln Gln His Gln
        595                 600                 605
Arg Leu Ala Gln Leu Leu Leu Ile Leu Ser His Ile Arg His Met Ser
        610                 615                 620
Asn Lys Gly Met Glu His Leu Tyr Ser Met Lys Cys Lys Asn Val Val
625                 630                 635                 640
Pro Leu Tyr Asp Leu Leu Leu Glu Met Leu Asp Ala His Arg Leu His
                645                 650                 655
Ala Pro Thr Ser Arg Gly Gly Ala Ser Val Glu Glu Thr Asp Gln Ser
            660                 665                 670
His Leu Ala Thr Ala Gly Ser Thr Ser Ser His Ser Leu Gln Lys Tyr
        675                 680                 685
Tyr Ile Thr Gly Glu Ala Glu Gly Phe Pro Ala Thr Val
690                 695                 700

<210> SEQ ID NO 13
<211> LENGTH: 595
<212> TYPE: PRT
<213> ORGANISM: human

<400> SEQUENCE: 13

Met Thr Met Thr Leu His Thr Lys Ala Ser Gly Met Ala Leu Leu His
1               5                   10                  15
Gln Ile Gln Gly Asn Glu Leu Glu Pro Leu Asn Arg Pro Gln Leu Lys
            20                  25                  30
Ile Pro Leu Glu Arg Pro Leu Gly Glu Val Tyr Leu Asp Ser Ser Lys
        35                  40                  45
Pro Ala Val Tyr Asn Tyr Pro Glu Gly Ala Ala Tyr Glu Phe Asn Ala
    50                  55                  60
Ala Ala Ala Ala Asn Ala Gln Val Tyr Gly Gln Thr Gly Leu Pro Tyr
65                  70                  75                  80
Gly Pro Gly Ser Glu Ala Ala Ala Phe Gly Ser Asn Gly Leu Gly Gly
                85                  90                  95
```

-continued

```
Phe Pro Pro Leu Asn Ser Val Ser Pro Ser Pro Leu Met Leu Leu His
        100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
        210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
        290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
        370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
        450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
```

-continued

```
            515                 520                 525
Lys Cys Lys Asn Val Val Pro Leu Tyr Asp Leu Leu Glu Met Leu
530                     535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
                580                 585                 590

Ala Thr Val
        595

<210> SEQ ID NO 14
<211> LENGTH: 595
<212> TYPE: PRT
<213> ORGANISM: Human

<400> SEQUENCE: 14

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
        210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285
```

```
Ala Asn Leu Trp Pro Ser Pro Leu Met Ile Lys Arg Ser Lys Lys Asn
    290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
        355                 360                 365
Asp Leu Thr Leu His Asp Gln Val His Leu Leu Glu Cys Ala Trp Leu
    370                 375                 380
Glu Ile Leu Met Ile Gly Leu Val Trp Arg Ser Met Glu His Pro Val
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
        515                 520                 525
Lys Cys Lys Asn Val Val Pro Leu Tyr Asp Leu Leu Leu Glu Met Leu
    530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
            580                 585                 590
Ala Thr Val
        595

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
caagcgccag agagatgatg                                              20

<210> SEQ ID NO 16
<211> LENGTH: 20
<212> TYPE: DNA
<213> ORGANISM: Artificial Sequence
<220> FEATURE:
<223> OTHER INFORMATION: Primer
```

<400> SEQUENCE: 16
acaaggcact gaccatctgg         20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gaccatctgg tcggccgtca         20

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
cagagagaat gatggggagg g         21

<210> SEQ ID NO 19
<211> LENGTH: 11522
<212> TYPE: DNA
<213> ORGANISM: Artificial Sequence
<220> FEATURE:
<223> OTHER INFORMATION: Vector pER8

<400> SEQUENCE: 19

| | | | | |
|---|---|---|---|---|
| gtttacccgc | caatatatcc | tgtcaaacac | tgatagttta | aactgaaggc gggaaacgac | 60 |
| aatctgatcc | aagctcaagc | taagcttgca | tgcctgcagg | atatcgtgga tccaagcttg | 120 |
| ccacgtgccg | ccacgtgccg | ccacgtgccg | ccacgtgcct | ctagaggatc catctccact | 180 |
| gacgtaaggg | atgacgcaca | atcccactat | ccttcgcaag | acccttcctc tatataagga | 240 |
| agttcatttc | atttggagag | gacacgctgg | gatccccaat | tccggcggaa atgaaagcgt | 300 |
| taacggccag | gcaacaagag | gtgtttgatc | tcatccgtga | tcacatcagc cagacaggta | 360 |
| tgccgccgac | gcgtgcggaa | atcgcgcagc | gtttggggtt | ccgttcccca aacgcggctg | 420 |
| aagaacatct | gaaggcgctg | gcacgcaaag | gcgttattga | aattgtttcc ggcgcatcac | 480 |
| gcgggattcg | tctgttgcag | gaagaggaag | aagggttgcc | gctggtaggt cgtgtggctg | 540 |
| ccggtgaacc | gtcgagcgcc | ccccgaccg | atgtcagcct | gggggacgag ctccacttag | 600 |
| acggcgagga | cgtggcgatg | gcgcatgccg | acgcgctaga | cgatttcgat ctggacatgt | 660 |
| tgggggacgg | ggattccccg | gtccgggat | ttaccccca | cgactccgcc ccctacggcg | 720 |
| ctctggatat | ggccgacttc | gagtttgagc | agatgtttac | cgatgccctt ggaattgacg | 780 |
| agtacggtgg | ggatccgtct | gctggagaca | tgagagctgc | caacctttgg ccaagcccgc | 840 |
| tcatgatcaa | acgctctaag | aagaacagcc | tggccttgtc | cctgacggcc gaccagatgg | 900 |
| tcagtgcctt | gttggatgct | gagcccccca | tactctattc | gagtatgat cctaccagac | 960 |
| ccttcagtga | agcttcgatg | atgggcttac | tgaccaacct | ggcagacagg gagctggttc | 1020 |
| acatgatcaa | ctgggcgaag | agggtgccag | gctttgtgga | tttgaccctc catgatcagg | 1080 |
| tccaccttct | agaatgtgcc | tggctagaga | tcctgatgat | tggtctcgtc tggcgctcca | 1140 |
| tggagcaccc | agtgaagcta | ctgtttgctc | ctaacttgct | cttggacagg aaccagggaa | 1200 |

-continued

```
aatgtgtaga gggcatggtg gagatcttcg acatgctgct ggctacatca tctcggttcc      1260
gcatgatgaa tctgcaggga gaggagtttg tgtgcctcaa atctattatt ttgcttaatt      1320
ctggagtgta cacatttctg tccagcaccc tgaagtctct ggaagagaag gaccatatcc      1380
accgagtcct ggacaagatc acagacactt tgatccacct gatggccaag gcaggcctga      1440
ccctgcagca gcagcaccag cggctggccc agctcctcct catcctctcc cacatcaggc      1500
acatgagtaa caaaggcatg gagcatctgt acagcatgaa gtgcaagaac gtggtgcccc      1560
tctatgacct gctgctggag atgctggacg cccaccgcct acatgcgccc actagccgtg      1620 gagggggcatc cgtggaggag acggaccaaa gccacttggc cactgcgggc tctacttcat      1680
cgcattcctt gcaaaagtat tacatcacgg gggaggcaga gggtttccct gccacagtct      1740
gagagctccc tggcgaattc ccagagatgt tagctgaaat catcactaat cagataccaa      1800
aatattcaaa tggaaatatc aaaaagcttc tgtttcatca aaaatgactc gacctaactg      1860
agtaagctag cttgttcgag tattatggca ttgggaaaac tgttttttctt gtaccatttg      1920 ttgtgcttgt aatttactgt gttttttatt cggttttcgc tatcgaactg tgaaatggaa      1980
atggatggag aagagttaat gaatgatatg gtccttttgt tcattctcaa attaatatta      2040
tttgtttttt ctcttatttg ttgtgtgttg aatttgaaat tataagagat atgcaaacat      2100
tttgttttga gtaaaaatgt gtcaaatcgt ggcctctaat gaccgaagtt aatatgagga      2160
gtaaaacatc ccaaacaagc ttggaaactg aaggcgggaa acgacaatct gatcatgagc      2220
ggagaattaa gggagtcacg ttatgacccc cgccgatgac gcgggacaag ccgttttacg      2280
tttggaactg acagaaccgc aacgattgaa ggagccactc agccgcgggt ttctggagtt      2340
taatgagcta agcacatacg tcagaaacca ttattgcgcg ttcaaaagtc gcctaaggtc      2400
actatcagct agcaaatatt tcttgtcaaa aatgctccac tgacgttcca taaattcccc      2460
tcggtatcca attagagtct catattcact ctcaatccaa ataatctgca ccggatcccc      2520
tagaatgaaa aagcctgaac tcaccgcgac gtctgtcgag aagtttctga tcgaaaagtt      2580
cgacagcgtc tccgacctga tgcagctctc ggagggcgaa gaatctcgtg ctttcagctt      2640
cgatgtagga gggcgtggat atgtcctgcg ggtaaatagc tgcgccgatg gtttctacaa      2700
agatcgttat gtttatcggc actttgcatc ggccgcgctc ccgattccgg aagtgcttga      2760
cattggggaa ttcagcgaga gcctgaccta ttgcatctcc cgccgtgcac agggtgtcac      2820
gttgcaagac ctgcctgaaa ccgaactgcc cgctgttctg cagccggtcg cggaggccat      2880
ggatgcgatc gctgcggccg atcttagcca dacgagcggg ttcggcccat tcggaccgca      2940
aggaatcggt caatacacta catggcgtga tttcatatgc gcgattgctg atccccatgt      3000
gtatcactgg caaactgtga tggacgacac cgtcagtgcg tccgtcgcgc aggctctcga      3060
tgagctgatg ctttgggccg aggactgccc cgaagtccgg cacctcgtgc acgcggattt      3120
cggctccaac aatgtcctga cggacaatgg ccgcataaca gcggtcattg actggagcga      3180
ggcgatgttc ggggattccc aatacgaggt cgccaacatc ttcttctgga ggccgtggtt      3240
ggcttgtatg gagcagcaga cgcgctactt cgagcggagg catccggagc ttgcaggatc      3300
gccgcggctc cgggcgtata tgctccgcat tggtcttgac caactctatc agagcttggt      3360
tgacggcaat ttcgatgatg cagcttgggc gcagggtcga tgcgacgcaa tcgtccgatc      3420
cggagccggg actgtcgggc gtacacaaat cgcccgcaga agcgcggccg tctgaccga      3480 tggctgtgta gaagtactcg ccgatagtgg aaaccgacgc cccagcactc gtccgagggc      3540
aaaggaatag cgatcgttca acatttggc aataaagttt cttaagattg aatcctgttg      3600
```

```
ccggtcttgc gatgattatc atataatttc tgttgaatta cgttaagcat gtaataatta    3660
acatgtaatg catgacgtta tttatgagat gggttttat gattagagtc ccgcaattat     3720
acatttaata cgcgatagaa aacaaaatat agcgcgcaaa ctaggataaa ttatcgcgcg    3780
cggtgtcatc tatgttacta gatcggggaa ttgatccccc ctcgacagct tgcatgccag    3840
cttgggctgc aggtcgaggc taaaaaacta atcgcattat catcccctcg acgtactgta    3900
catataacca ctggttttat atacagcagt actgtacata taaccactgg ttttatatac    3960
agcagtcgac gtactgtaca tataaccact ggttttatat acagcagtac tgtacatata    4020
accactggtt ttatatacag cagtcgaggt aagattagat atggatatgt atatggatat    4080
gtatatggtg gtaatgccat gtaatatgct cgactctagg atcttcgcaa gacccttcct    4140
ctatataagg aagttcattt catttggaga ggacacgctg aagctagtcg actctagcct    4200
cgaggcgcgc cgggcccagg cctacgcgtt aattaacta gtcgatccag gcctcccagc     4260
tttcgtccgt atcatcggtt tcgacaacgt tcgtcaagtt caatgcatca gtttcattgc    4320
ccacacacca gaatcctact aagtttgagt attatggcat tggaaaagct gttttcttct    4380
atcatttgtt ctgcttgtaa tttactgtgt tctttcagtt tttgttttcg acatcaaaa    4440 tgcaaatgga tggataagag ttaataaatg atatggtcct tttgttcatt ctcaaattat    4500
tattatctgt tgtttttact ttaatgggtt gaatttaagt aagaaaggaa ctaacagtgt    4560
gatattaagg tgcaatgtta gacatataaa acagtctttc acctctcttt ggttatgtct    4620
tgaattggtt tgtttcttca cttatctgtg taatcaagtt tactatgagt ctatgatcaa    4680
gtaattatgc aatcaagtta agtacagtat aggcttttg tgtcgagggg gtaccgagtc     4740
gaggaattca ctggccgtcg ttttacaacg tcgtgactgg gaaaaccctg gcgttaccca    4800
acttaatcgc cttgcagcac atcccccttt cgccagctgg cgtaatagcg aagaggcccg    4860
caccgatcgc ccttcccaac agttgcgcag cctgaatggc gggtaccgag ctcgaattca    4920
attcggcgtt aattcagtac attaaaaacg tccgcaatgt gttattaagt tgtctaagcg    4980
tcaatttgtt tacaccacaa tatatcctgc caccagccag ccaacagctc ccgaccggc     5040 agctcggcac aaaatcacca ctcgatacag gcagcccatc agtccgggac ggcgtcagcg    5100
ggagagccgt tgtaaggcgg cagactttgc tcatgttacc gatgctattc ggaagaacgg    5160
caactaagct gccgggtttg aaacacggat gatctcgcgg agggtagcat gttgattgta    5220
acgatgacag agcgttgctg cctgtgatca attcgggcac gaacccagtg gacataagcc    5280
tcgttcggtt cgtaagctgt aatgcaagta gcgtaactgc cgtcacgcaa ctggtccaga    5340
accttgaccg aacgcagcgg tggtaacggc gcagtggcgg ttttcatggc ttcttgttat    5400
gacatgtttt tttggggtac agtctatgcc tcgggcatcc aagcagcaag cgcgttacgc    5460
cgtgggtcga tgtttgatgt tatggagcag caacgatgtt acgcagcagg cagtcgccc     5520 taaaacaaag ttaaacatca tggggaagc ggtgatcgcc gaagtatcga ctcaactatc     5580
agaggtagtt ggcgtcatcg agcgccatct cgaaccgacg ttgctggccg tacatttgta    5640
cggctccgca gtggatggcg gcctgaagcc acacagtgat attgatttgc tggttacggt    5700
gaccgtaagg cttgatgaaa caacgcggcg agctttgatc aacgaccttt tggaaacttc    5760
ggcttcccct ggagagagcg agattctccg cgctgtagaa gtcaccattg ttgtgcacga    5820
cgacatcatt ccgtggcgtt atccagctaa gcgcgaactg caatttggag aatggcagcg    5880
caatgacatt cttgcaggta tcttcgagcc agccacgatc gacattgatc tggctatctt    5940
```

-continued

```
gctgacaaaa gcaagagaac atagcgttgc cttggtaggt ccagcggcgg aggaactctt   6000
tgatccggtt cctgaacagg atctatttga ggcgctaaat gaaaccttaa cgctatggaa   6060
ctcgccgccc gactgggctg gcgatgagcg aaatgtagtg cttacgttgt cccgcatttg   6120
gtacagcgca gtaaccggca aaatcgcgcc gaaggatgtc gctgccgact gggcaatgga   6180
gcgcctgccg gcccagtatc agcccgtcat acttgaagct agacaggctt atcttggaca   6240
agaagaagat cgcttggcct cgcgcgcaga tcagttggaa gaatttgtcc actacgtgaa   6300
aggcgagatc accaaggtag tcggcaaata atgtctagct agaaattcgt tcaagccgac   6360
gccgcttcgc cggcgttaac tcaagcgatt agatgcacta agcacataat tgctcacagc   6420
caaactatca ggtcaagtct gcttttatta ttttttaagcg tgcataataa gccctacaca   6480
aattgggaga tatatcatgc atgaccaaaa tcccttaacg tgagttttcg ttccactgag   6540
cgtcagaccc cgtagaaaag atcaaaggat cttcttgaga tccttttttt ctgcgcgtaa   6600
tctgctgctt gcaaacaaaa aaaccaccgc taccagcggt ggtttgtttg ccggatcaag   6660
agctaccaac tcttttccg aaggtaactg gcttcagcag agcgcagata ccaaatactg   6720
tccttctagt gtagccgtag ttaggccacc acttcaagaa ctctgtagca ccgcctacat   6780
acctcgctct gctaatcctg ttaccagtgg ctgctgccag tggcgataag tcgtgtctta   6840
ccgggttgga ctcaagacga tagttaccgg ataaggcgca gcggtcgggc tgaacggggg   6900
gttcgtgcac acagcccagc ttggagcgaa cgacctacac cgaactgaga tacctacagc   6960
gtgagctatg agaaagcgcc acgcttcccg aagggagaaa ggcggacagg tatccggtaa   7020
gcggcagggt cggaacagga gagcgcacga gggagcttcc agggggaaac gcctggtatc   7080
tttatagtcc tgtcgggttt cgccacctct gacttgagcg tcgatttttg tgatgctcgt   7140
caggggggcg gagcctatgg aaaaacgcca gcaacgcggc cttttacgg ttcctggcct   7200 tttgctggcc ttttgctcac atgttctttc ctgcgttatc ccctgattct gtggataacc   7260
gtattaccgc ctttgagtga gctgataccg ctcgccgcag ccgaacgacc gagcgcagcg   7320
agtcagtgag cgaggaagcg gaagagcgcc tgatgcggta ttttctcctt acgcatctgt   7380
gcggtatttc acaccgcata tggtgcactc tcagtacaat ctgctctgat gccgcatagt   7440
taagccagta tacactccgc tatcgctacg tgactgggtc atggctgcgc ccgacaccc    7500 gccaacaccc gctgacgcgc cctgacgggc ttgtctgctc ccggcatccg cttacagaca   7560
agctgtgacc gtctccggga gctgcatgtg tcagaggttt tcaccgtcat caccgaaacg   7620
cgcgaggcag ggtgccttga tgtgggcgcc ggcggtcgag tggcgacggc gcggcttgtc   7680
cgcgccctgg tagattgcct ggccgtaggc cagccatttt tgagcggcca gcggccgcga   7740
taggccgacg cgaagcggcg gggcgtaggg agcgcagcga ccgaagggta ggcgcttttt   7800
gcagctcttc ggctgtgcgc tggccagaca gttatgcaca ggccaggcgg gttttaagag   7860
ttttaataag ttttaaagag ttttaggcgg aaaaatcgcc ttttttctct tttatatcag   7920
tcacttacat gtgtgaccgg ttcccaatgt acggctttgg gttcccaatg tacgggttcc   7980
ggttcccaat gtacgtggttt gggttcccaa tgtacgtgct atccacagga aagagacctt   8040
ttcgaccttt tccctgct agggcaattt gccctagcat ctgctccgta cattaggaac    8100
cggcggatgc ttcgccctcg atcaggttgc ggtagcgcat gactaggatc gggccagcct   8160
gccccgcctc ctccttcaaa tcgtactccg gcaggtcatt tgacccgatc agcttgcgca   8220
cggtgaaaca gaacttcttg aactctccgg cgctgccact gcgttcgtag atcgtcttga   8280
acaaccatct ggcttctgcc ttgcctgcgg cgcggcgtgc caggcggtag agaaaacggc   8340
```

```
cgatgccggg atcgatcaaa aagtaatcgg ggtgaaccgt cagcacgtcc gggttcttgc   8400
cttctgtgat ctcgcggtac atccaatcag ctagctcgat ctcgatgtac tccggccgcc   8460
cggtttcgct ctttacgatc ttgtagcggc taatcaaggc ttcaccctcg gataccgtca   8520
ccaggcggcc gttcttggcc ttcttcgtac gctgcatggc aacgtgcgtg gtgtttaacc   8580
gaatgcaggt ttctaccagg tcgtctttct gctttccgcc atcggctcgc cggcagaact   8640
tgagtacgtc cgcaacgtgt ggacggaaca cgcggccggg cttgtctccc ttcccttccc   8700
ggtatcggtt catggattcg gttagatggg aaaccgccat cagtaccagg tcgtaatccc   8760
acacactggc catgccggcc ggccctgcgg aaacctctac gtgcccgtct ggaagctcgt   8820
agcggatcac ctcgccagct cgtcggtcac gcttcgacag acggaaaacg gccacgtcca   8880
tgatgctgcg actatcgcgg gtgcccacgt catagagcat cggaacgaaa aaatctggtt   8940
gctcgtcgcc cttgggcggc ttcctaatcg acggcgcacc ggctgccggc ggttgccggg   9000
attctttgcg gattcgatca gcggccgctt gccacgattc accggggcgt gcttctgcct   9060
cgatgcgttg ccgctgggcg gcctgcgcgg ccttcaactt ctccaccagg tcatcaccca   9120
gcgccgcgcc gatttgtacc gggccggatg gtttgcgacc gtcacgccga ttcctcgggc   9180
ttggggttc cagtgccatt gcagggccgg cagacaaccc agccgcttac gcctggccaa   9240
ccgcccgttc ctccacacat ggggcattcc acggcgtcgg tgcctggttg ttcttgattt   9300
tccatgccgc ctcctttagc cgctaaaatt catctactca tttattcatt tgctcattta   9360
ctctggtagc tgcgcgatgt attcagatag cagctcggta atggtcttgc cttggcgtac   9420
cgcgtacatc ttcagcttgg tgtgatcctc cgccggcaac tgaaagttga cccgcttcat   9480
ggctggcgtg tctgccaggc tggccaacgt tgcagccttg ctgctgcgtg cgctcggacg   9540
gccggcactt agcgtgtttg tgcttttgct cattttctct ttacctcatt aactcaaatg   9600
agttttgatt taatttcagc ggccagcgcc tggacctcgc gggcagcgtc gccctcgggt   9660
tctgattcaa gaacggttgt gccggcggcg gcagtgcctg ggtagctcac gcgctgcgtg   9720
atacgggact caagaatggg cagctcgtac ccggccagcg cctcggcaac ctcaccgccg   9780
atgcgcgtgc ctttgatcgc ccgcgacacg acaaaggccg cttgtagcct tccatccgtg   9840
acctcaatgc gctgcttaac cagctccacc aggtcggcgg tggcccatat gtcgtaaggg   9900
cttggctgca ccggaatcag cacgaagtcg gctgccttga tcgcggacac agccaagtcc   9960
gccgcctggc gcgctccgtc gatcactacg aagtcgcgcc ggcgatggc cttcacgtcg  10020
cggtcaatcg tcggcggtc gatgccgaca acggttagcg gttgatcttc ccgcacggcc  10080
gcccaatcgc gggcactgcc ctggggatcg gaatcgacta acagaacatc ggccccggcg  10140
agttgcaggg cgcgggctag atggggttgcg atggtcgtct tgcctgaccc gccttctgg  10200
ttaagtacag cgataacctt catgcgttcc ccttgcgtat ttgtttattt actcatcgca  10260
tcatatacgc agcgaccgca tgacgcaagc tgttttactc aaatacacat caccttttta  10320
gacggcggcg ctcggtttct tcagcggcca agctggccgg ccaggccgcc agcttggcat  10380
cagacaaacc ggcaggatt tcatgcagcc gcacggttga cgtgcgcg gcggctcga   10440
acacgtaccc ggccgcgatc atctccgcct cgatctcttc ggtaatgaaa aacggttcgt  10500
cctggccgtc ctggtgcggt ttcatgcttg ttcctcttgg cgttcattct cggcggccgc  10560
cagggcgtcg gcctcggtca atgcgtcctc acggaaggca ccgcgccgcc tggcctcggt  10620
gggcgtcact tcctcgctgc gctcaagtgc gcggtacagg tcgagcgat gcacgccaag  10680
```

-continued

| | | | | |
|---|---|---|---|---|
| cagtgcagcc | gcctctttca | cggtgcggcc | ttcctggtcg | atcagctcgc gggcgtgcgc | 10740 |
| gatctgtgcc | ggggtgaggg | tagggcgggg | gccaaacttc | acgcctcggg ccttggcggc | 10800 |
| ctcgcgcccg | ctccgggtgc | ggtcgatgat | tagggaacgc | tcgaactcgg caatgccggc | 10860 |
| gaacacggtc | aacaccatgc | ggccggccgg | cgtggtggtg | tcggcccacg gctctgccag | 10920 |
| gctacgcagg | cccgcgccgg | cctcctggat | gcgctcggca | atgtccagta ggtcgcgggt | 10980 |
| gctgcgggcc | aggcggtcta | gcctggtcac | tgtcacaacg | tcgccagggc gtaggtggtc | 11040 |
| aagcatcctg | gccagctccg | ggcggtcgcg | cctggtgccg | gtgatcttct cggaaaacag | 11100 |
| cttggtgcag | ccggccgcgt | gcagttcggc | ccgttggttg | tcaagtcct ggtcgtcggt | 11160 |
| gctgacgcgg | gcatagccca | gcaggccagc | ggcggcgctc | ttgttcatgg cgtaatgtct | 11220 |
| ccggttctag | tcgcaagtat | tctactttat | gcgactaaaa | cacgcgacaa gaaaacgcca | 11280 |
| ggaaaagggc | agggcggcag | cctgtcgcgt | aacttaggac | ttgtgcgaca tgtcgttttc | 11340 |
| agaagacggc | tgcactgaac | gtcagaagcc | gactgcacta | gcagcggag ggggttggat | 11400 |
| caaagtactt | tgatcccgag | gggaaccctg | tggttggcat | gcacatacaa atggacgaac | 11460 |
| ggataaacct | tttcacgccc | ttttaaatat | ccgttattct | aataaacgct ctttctctt | 11520 |
| ag | | | | | 11522 |

<210> SEQ ID NO 20
<211> LENGTH: 6610
<212> TYPE: DNA
<213> ORGANISM: Artificial Sequence
<220> FEATURE:
<223> OTHER INFORMATION: Vector pCI-n GL1-HEGO

<400> SEQUENCE: 20

| | | | | | |
|---|---|---|---|---|---|
| tcaatattgg | ccattagcca | tattattcat | tggttatata | gcataaatca atattggcta | 60 |
| ttggccattg | catacgttgt | atctatatca | taatatgtac | atttatattg gctcatgtcc | 120 |
| aatatgaccg | ccatgttggc | attgattatt | gactagttat | taatagtaat caattacggg | 180 |
| gtcattagtt | catagcccat | atatggagtt | ccgcgttaca | taacttacgg taaatggccc | 240 |
| gcctggctga | ccgcccaacg | acccccgccc | attgacgtca | ataatgacgt atgttcccat | 300 |
| agtaacgcca | atagggactt | tccattgacg | tcaatgggtg | gagtatttac ggtaaactgc | 360 |
| ccacttggca | gtacatcaag | tgtatcatat | gccaagtccg | cccctattg acgtcaatga | 420 |
| cggtaaatgg | cccgcctggc | attatgccca | gtacatgacc | ttacgggact ttcctacttg | 480 |
| gcagtacatc | tacgtattag | tcatcgctat | taccatggta | atgcggtttt ggcagtacac | 540 |
| caatgggcgt | ggatagcggt | ttgactcacg | gggatttcca | agtctccacc ccattgacgt | 600 |
| caatgggagt | ttgttttggc | accaaaatca | acgggacttt | ccaaaatgtc gtaataaccc | 660 |
| cgccccgttg | acgcaaatgg | gcggtaggcg | tgtacggtgg | gaggtctata taagcagagc | 720 |
| tcgtttagtg | aaccgtcaga | tcactagaag | ctttattgcg | gtagtttatc acagttaaat | 780 |
| tgctaacgca | gtcagtgctt | ctgacacaac | agtctcgaac | ttaagctgca gaagttggtc | 840 |
| gtgaggcact | gggcaggtaa | gtatcaaggt | tacaagacag | gtttaaggag accaatagaa | 900 |
| actgggcttg | tcgagacaga | gaagactctt | gcgtttctga | taggcaccta ttggtcttac | 960 |
| tgacatccac | tttgcctttc | tctccacagg | tgtccactcc | cagttcaatt acagctctta | 1020 |
| aggctagagt | acttaatacg | actcactata | ggctagcgaa | ggagatccgc catgcccac | 1080 |
| catcaccacc | atcacggata | tccatacgac | gtgccagatt | acgctcagtc gagtgccatg | 1140 |
| agcaagggcg | aggaactgtt | cactggcgtg | gtcccaattc | tcgtggaact ggatggcgat | 1200 |

```
gtgaatgggc acaaattttc tgtcagcgga gagggtgaag gtgatgccac atacggaaag    1260
ctcaccctga aattcatctg caccactgga aagctccctg tgccatggcc aacactggtc    1320
actaccttca cctatggcgt gcagtgcttt tccagatacc cagaccatat gaagcagcat    1380 gacttttca agagcgccat gcccgagggc tatgtgcagg agagaaccat cttttttcaaa   1440 gatgacggga actacaagac ccgcgctgaa gtcaagttcg aaggtgacac cctggtgaat    1500
agaatcgagc tgaagggcat tgactttaag gaggatggaa acattctcgg ccacaagctg    1560
gaatacaact ataactccca caatgtgtac atcatggccg acaagcaaaa gaatggcatc    1620
aaggtcaact tcaagatcag acacaacatt gaggatggat ccgtgcagct ggccgaccat    1680
tatcaacaga acactccaat cggcgacggc cctgtgctcc tcccagacaa ccattacctg    1740
tccacccagt ctgccctgtc taaagatccc aacgaaaaga gagaccacat ggtcctgctg    1800
gagtttgtga ccgctgctgg gatcacacat ggcatggacg agctgtacaa gggcgccggc    1860
gctggtgctg gtgctggcgc catcagcgcg ttgaccctcc acaccaaagc atctgggatg    1920
gccctactgc atcagatcca agggaacgag ctggagcccc tgaaccgtcc gcagctcaag    1980 atcccctgg agcggcccct gggcgaggtg tacctggaca gcagcaagcc cgccgtgtac    2040
aactaccccg agggcgccgc ctacgagttc aacgccgcgg ccgccgccaa cgcgcaggtc    2100
tacggtcaga ccggcctccc ctacggcccc gggtctgagg ctgcggcgtt cggctccaac    2160
ggcctggggg gtttcccccc actcaacagc gtgtctccga gccgctgat gctactgcac    2220 ccgccgccgc agctgtcgcc tttcctgcag ccccacggcc agcaggtgcc ctactacctg    2280
gagaacgagc ccagcggcta cacggtgcgc gaggccggcc cgccggcatt ctacaggcca    2340
aattcagata atcgacgcca gggtggcaga gaaagattgg ccagtaccaa tgacaaggga    2400
agtatggcta tggaatctgc caaggagact cgctactgtg cagtgtgcaa tgactatgct    2460
tcaggctacc attatggagt ctggtcctgt gagggctgca aggccttctt caagagaagt    2520
attcaaggac ataacgacta tatgtgtcca gccaccaacc agtgcaccat tgataaaaac    2580
aggaggaaga gctgccaggc ctgccggctc cgcaaatgct acgaagtggg aatgatgaaa    2640
ggtgggatac gaaaagaccg aagaggaggg agaatgttga acacaagcg ccagagagat    2700 gatggggagg cagggtga agtggggtct gctggagaca tgagagctgc caaccttttgg    2760 ccaagcccgc tcatgatcaa acgctctaag aagaacagcc tggccttgtc cctgacggcc    2820
gaccagatgt tcagtgcctt gttggatgct gagccccca tactctattc cgagtatgat    2880
cctaccagac ccttcagtga agcttcgatg atgggcttac tgaccaacct ggcagacagg    2940
gagctggttc acatgatcaa ctgggcgaag agggtgccag gctttgtgga tttgacctc    3000 catgatcagg tccaccttct agaatgtgcc tggctagaga tcctgatgat tggtctcgtc    3060
tggcgctcca tggagcaccc agtgaagcta ctgtttgctc ctaacttgct cttggacagg    3120
aaccagggaa aatgtgtaga gggcatggtg agatcttcg acatgctgct ggctacatca    3180
tctcggttcc gcatgatgaa tctgcaggga gaggagtttg tgtgcctcaa atctattatt    3240
ttgcttaatt ctggagtgta cacatttctg tccagcaccc tgaagtctct ggaagagaag    3300
gaccatatcc accgagtcct ggacaagatc acagacactt tgatccacct gatggccaag    3360
gcaggcctga ccctgcagca gcagcaccag cggctggccc agctcctcct catcctctcc    3420
cacatcaggc acatgagtaa caaaggcatg gagcatctgt acagcatgaa gtgcaagaac    3480
gtggtgcccc tctatgacct gctgctggag atgctggacg cccaccgcct acatgcgccc    3540
```

```
actagccgtg aggggcatc cgtggaggag acggaccaaa gccacttggc cactgcgggc   3600
tctacttcat cgcattcctt gcaaaagtat tacatcacgg gggaggcaga gggtttccct   3660
gccacagtct gagagctccc tggcggaatt cggatcgggc ggccgcttcg agcagacatg   3720
ataagataca ttgatgagtt tggacaaacc acaactagaa tgcagtgaaa aaaatgcttt   3780
atttgtgaaa tttgtgatgc tattgcttta tttgtaacca ttataagctg caataaacaa   3840
gttaacaaca acaattgcat tcattttatg tttcaggttc agggggagat gtgggaggtt   3900
ttttaaagca agtaaaacct ctacaaatgt ggtaaaatcg ataaggatcc gggctggcgt   3960
aatagcgaag aggcccgcac cgatcgccct tcccaacagt tgcgcagcct gaatggcgaa   4020
tggacgcgcc ctgtagcggc gcattaagcg cggcgggtgt ggtggttacg cgcagcgtga   4080
ccgctacact tgccagcgcc ctagcgcccg ctcctttcgc tttcttccct cctttctcg   4140
ccacgttcgc cggctttccc cgtcaagctc taaatcgggg gctcccttta gggttccgat   4200
ttagagcttt acggcacctc gaccgcaaaa aacttgattt gggtgatggt tcacgtagtg   4260
ggccatcgcc ctgatagacg gttttttcgcc ctttgacgtt ggagtccacg ttctttaata   4320
gtggactctt gttccaaact ggaacaacac tcaaccctat ctcggtctat tcttttgatt   4380
tataagggat tttgccgatt tcggcctatt ggttaaaaaa tgagctgatt taacaaatat   4440
ttaacgcgaa ttttaacaaa atattaacgt ttacaatttc gcctgatgcg gtattttctc   4500
cttacgcatc tgtgcggtat ttcacaccgc atatggtgca ctctcagtac aatctgctct   4560
gatgccgcat agttaagcca gccccgacac ccgccaacac ccgctgacgc gccctgacgg   4620
gcttgtctgc tcccggcatc cgcttacaga caagctgtga ccgtctccgg gagctgcatg   4680
tgtcagaggt tttcaccgtc atcaccgaaa cgcgcgagac gaaagggcct cgtgatacgc   4740
ctatttttat aggttaatgt catgataata atggtttctt agacgtcagg tggcacttt   4800
cggggaaatg tgcgcggaac ccctatttgt ttatttttct aaatacattc aaatatgtat   4860
ccgctcatga gacaataacc ctgataaatg cttcaataat attgaaaaag gaagagtatg   4920
agtattcaac atttccgtgt cgcccttatt cccttttttg cggcattttg ccttcctgtt   4980
tttgctcacc cagaaacgct ggtgaaagta aaagatgctg aagatcagtt gggtgcacga   5040
gtgggttaca tcgaactgga tctcaacagc ggtaagatcc ttgagagttt tcgccccgaa   5100
gaacgttttc caatgatgag cacttttaaa gttctgctat gtggcgcggt attatcccgt   5160
attgacgccg ggcaagagca actcggtcgc cgcatacact attctcagaa tgacttggtt   5220
gagtactcac cagtcacaga aaagcatctt acggatggca tgacagtaag agaattatgc   5280
agtgctgcca taaccatgag tgataacact gcggccaact tacttctgac aacgatcgga   5340
ggaccgaagg agctaaccgc ttttttgcac aacatggggg atcatgtaac tcgccttgat   5400
cgttgggaac cggagctgaa tgaagccata ccaaacgacg agcgtgacac cacgatgcct   5460
gtagcaatgg caacaacgtt gcgcaaacta ttaactggcg aactacttac tctagcttcc   5520
cggcaacaat taatagactg gatggaggcg gataaagttg caggaccact tctgcgctcg   5580
gcccttccgg ctggctggtt tattgctgat aaatctggag ccggtgagcg tgggtctcgc   5640
ggtatcattg cagcactggg gccagatggt aagccctccc gtatcgtagt tatctacacg   5700
acggggagtc aggcaactat ggatgaacga atagacaga tcgctgagat aggtgcctca   5760
ctgattaagc attggtaact gtcagaccaa gtttactcat atatacttta gattgattta   5820
aaacttcatt tttaatttaa aaggatctag gtgaagatcc ttttttgataa tctcatgacc   5880
aaaatccctt aacgtgagtt ttcgttccac tgagcgtcag accccgtaga aaagatcaaa   5940
```

```
ggatcttctt gagatccttt tttctgcgc gtaatctgct gcttgcaaac aaaaaaacca      6000
ccgctaccag cggtggtttg tttgccggat caagagctac caactctttt tccgaaggta      6060
actggcttca gcagagcgca gataccaaat actgtccttc tagtgtagcc gtagttaggc      6120
caccacttca agaactctgt agcaccgcct acatacctcg ctctgctaat cctgttacca      6180
gtggctgctg ccagtggcga taagtcgtgt cttaccgggt tggactcaag acgatagtta      6240
ccggataagg cgcagcggtc gggctgaacg ggggttcgt gcacacagcc cagcttggag       6300
cgaacgacct acaccgaact gagataccta cagcgtgagc tatgagaaag cgccacgctt      6360
cccgaaggga gaaaggcgga caggtatccg gtaagcggca gggtcggaac aggagagcgc      6420
acgagggagc ttccaggggg aaacgcctgg tatctttata gtcctgtcgg gtttcgccac      6480
ctctgacttg agcgtcgatt tttgtgatgc tcgtcagggg ggcggagcct atggaaaaac      6540
gccagcaacg cggcctttt acggttcctg gccttttgct ggccttttgc tcacatggct       6600
cgacagatct                                                             6610

<210> SEQ ID NO 21
<211> LENGTH: 2525
<212> TYPE: DNA
<213> ORGANISM: Violet Cress

<400> SEQUENCE: 21
agcaatggtt caacatcaac caccaccaca agtccctcct cctccgtcgc agcaatctcc        60
ggtaacacca ctaacggcgg cgtttgggat gagattaggt ggtctagaag gtttgttcgg       120
tccttacggg atacgttttt acacggcggc gaagatagcc gagttaggtt tcacggcgag       180
cactctcgtt ggtatgaaag acgaagagct tgaagatatg atgaatagtc tctctcatat       240
ctttcgttgg gagcttcttg ttggtgaacg ttacggtata aaagctgccg ttagagctga       300
acggaggaga ttgcaagaag aggaggaaga tgaatcttct agacgccgtc atttgcttct       360
ctccgccgct ggtgattccg gcactcacca cgctcttgat gctctctctc aagaaggtac       420
taatattaaa atttatataa ttttttttca cggtttatat atttacgtac ttattgttat       480
acgtatcacg taagtaactt atctatatag gttcaataaa ctgttaaaaa tctatgttca      540
cgtgaccgat tgatataaag ttatatgagt ttttacatga tatatattag agtaatattg      600 tatgataccct agtcgttaac aacataattt aatgaatcat tataaaataa tattgcaatt      660
gttaaggaat ctctattcac attcaacact tctatataaa ttaacttaaa aattgttgac      720
aaacaaaaaa ttaacttaaa aataataaac tcattatgta tatagtatgt gtatagtaac      780
gctattatct atagagtttc acgagtgata gtctgaattt tatttattaa agtcctatta      840
caaagtacga ggaataatat catataatat aattatatac gcgtatatat atttaaattt      900
ttaatgaacg tgcataagt aactgtagat gattggacag gcttatctga ggaaccgatg        960
catcaagacc aaactgacgc ggcgggtaac ggcggattcg gtggttattt ggaatcatca      1020
gtacacggaa agatgaagaa acatcaacca agacgtagaa agaaaccgtt ggtactgacg      1080
tcagttgaaa ccgacgatga cggcaacgat aacgaggatg acgacgggat ggataacggt      1140
aacggaggta ttgggttagg gacggagaga cagagagaac atccgtttat tgtaactgag      1200
cctggggaag tggcacgtgg caaaaagaac ggtttggatt atcttttcca cttgtacgaa      1260
caatgccgtg agttccttct tcaggtccag actattgcta aagaccgtgg cgaaaaatgc      1320
cccaccaagg tatctttctc aagatttaat actagccgtt gatttaattc aattaaatat      1380
```

```
attataacac atgatgtcgg aaagtaggag gtatggtatg gtagggaaag tatatagcca    1440
taatcatgga cagctgtttt aaagtaagtt tgacaagtca cgagttcaga gttttcacta    1500
ggattttttg tttagttatt gctatgtctg gcaaacattt atataggttt tagatttgtt    1560 taatttttt ttattctacc tttagaataa atatagagtt agattttcaa tataaaaaat    1620
gtgacagtca ccgtacaact acgtgtcgag ttagggaaag gagacagttg tttcttgttt    1680
ttggctaaaa cgacataaga tagcaagata cgatgtcctc atgctttaga tactatttct    1740
gcatgcattc acacacacat gtataatgtt taggtgtata tattagctag atatttctat    1800
ttttataatt tgttgggtgc atatatatat taaaaaatag tatagtatat agtgataata    1860
tttagaaaca gtctattgat cagcgggtaa taaagggtct ctactttcca ctagtgaaga    1920
tagtacaaaa tccacgagct ctgtgccatt gcttgtacag acgcacgtta ctaaattctg    1980
agttgttaca gaaaatttaa ccgaataaaa ctctttttaa tttcttcttt caaaaatttg    2040
ggttttgaac atattttttt tggctgttta gtctaacgaa gagctgtatt aaagatactg    2100
tatttatcac tactaaattt attttgaaaa tctagtataa ataaattatt tacttcatat    2160
tgattattat ggtaatgaaa ggttatatgt aaaacaggtg acgaaccaag tgtttaggta    2220
cgctaaaaaa tcaggagcga gttacataaa caaaccaaaa atgcgacact acgttcattg    2280
ttacgctctc cactgcctag acgaagaagc atcaaacgct ctaagaagag cgtttaaaga    2340
acgcggcgag aacgttggct cgtggcgtca ggcttgttac aagccgctag tgaacatagc    2400
ctgtcgtcat ggctgggaca tagacgccgt tttcaacgca catcctcgtc tatctatttg    2460
gtacgttcca actaaactgc gtcagctttg ccatttggag cgtaacaacg ccgttgctgc    2520
ggcgg                                                                2525

<210> SEQ ID NO 22
<211> LENGTH: 9
<212> TYPE: DNA
<213> ORGANISM: Human

<400> SEQUENCE: 22 ggggcgtgg                                                               9

<210> SEQ ID NO 23
<211> LENGTH: 1978
<212> TYPE: DNA
<213> ORGANISM: Hamster

<400> SEQUENCE: 23
cactcgatca ttcgagcaca ttccttcctt ccttcttact gtctcggccc tcacctctac     60
aagcccatgg aacgtttctg caaaggcgct cttgcaccgg cagggtggcc agtccgctgc    120
tgagccctct gcgtgcgcgg ggagcctgtc tgcgcctcgc cggccgccgc taaccatgac    180
catgaccctc cacaccaaag cctcgggaat ggccttgctg caccagatcc aagggaacga    240
gctggagccc ctcagccgcc cgcagctcaa gatgcccctg gagagggccc tgagcgaggt    300
gtacgtggac agcagtaagc ccgcgatgtt caactacccc gagggcgccg cctacgagtt    360
caacgccgcc accgcccccg cgccggtcta cggccagacg ggcatcgcct atggctctgg    420
gtccgaggcg accgccttcg gttccaacag cctggggctt tttccccagc tcaacagcgt    480 gtcgccagc ccgctgatgc tactgcaccc gccgccgccg cagctgtcgc ccttcctgca    540
cccgcacggc cagcaggtgc cctactacct ggagaatgag cctagcgcct atgccgtgcg    600
cgacagcggc cctccagcct tctacagatc taattctgat aatcgacgcc agagtggccg    660
```

```
agagagactg tccagcagca gcgagaaagg aagcatggcc atggagtctg tcaaggagac      720
tcgctactgt gcagtgtgca atgactacgc ctctggctac cattatgggg tctggtcctg      780
tgaaggctgc aaggctttct tcaagagaag tattcaagga cacaatgact acatgtgtcc      840
agctacaaac caatgcacaa tcgacaagaa caggagaaag agctgccagg cctgcaggct      900
gcgcaagtgt tacgaagtag gcatgatgaa aggtgggata cggaaagacc ggagaggagg      960
gagaatgctg aaacacaagc gccagagaga cgacttggaa ggcaggaacg catggggcc     1020 ttcaggagac atgagggcca ccaacctttg gcctagtcct cttgtgatta agcacactaa     1080
gaagaacagc cctgccttgt ccttgacagc cgaccaaatg gtcagtgcct tgttggatgc     1140
tgaaccgccc ttaatctatt ctgaatatga tccttctaga cctttcagcg aagcttcgat     1200
gatgggatta ttgaccaacc tggcagacag ggagttggtt catatgatca actgggcaaa     1260
gagagtgcca ggctttggag acttaaatct ccatgatcag gtccacctcc tggagtgtgc     1320
ctggttggag atcctgatga ttggtctcat ctggcgctcc atggaacacc cagggaagct     1380
cctgtttgct cctaatttgc tcctggacag gaatcagggc aagtgtgtgg agggcatggt     1440
ggagatcttt gacatgttgc tggctacatc agctcggttc cgcatgatgg acctgcaggg     1500
agaggagttt gtgtgcctca aatctatcat tttgcttaat tctggagtgt acacatttct     1560
gtccagcacc ttgaagtctc tggaggagaa ggaccacatc caccgggtcc tggataagat     1620
cacagacact ttgattcacc tgatggccaa agctggcctg acactgcagc agcagcatcg     1680
tcgtctggcc cagctcctcc tcattctttc ccacatccgg cacatgagta acaaaggcat     1740
ggagcacctc tacaacatga aatgcaagaa cgttgtaccc ttctatgacc tgttgctgga     1800
gatgttggat gctcaccgcc tgcataccc cgtcagtcgc atggggggtct ccccagagga     1860 gcccagtcag agccagctga ccaccaccaa ctccacttca tcacattcct tacaaaccta     1920
ctacatcccg tcggaagcag agagtttccc caacacaatc tgagacctcc caggctcc      1978
```

<210> SEQ ID NO 24
<211> LENGTH: 1788
<212> TYPE: DNA
<213> ORGANISM: Pig

<400> SEQUENCE: 24

```
atgaccatga ccctacacac caaagcgtcc ggcatggccc tgctgcacca gatccaagcc       60
aacgagctgg agcccctgaa ccgcccgcag ctcaagatcc ccctggagcg gcccctgggc      120
gaggtgtacg tggacagcag caagcccgcc gtgtataact accccgaggg cgccgcgtac      180
gacttcaacg ccgcggccgc cgcctccgcg cccgtctacg ccagtcgggg cctcgcctac      240
ggcccggggt cggaggcggc ggcgttcggc gccaacggct gggggggctt ccagccgctc      300
aacagcgtgt ctccgagccc gctggtgctg ctgcaccccgc cgccgcagct ctcgcccttc      360
ctgcaccccc acggccaaca ggtgccctat tacctggaga tgagccgag cggctatgcg      420 gtgcgcgagg ccgccctcc cgccttctac aggccaaatt cagataatcg cgccagggt      480 ggcagagaga gattggccag caccagtgac aagggaagca tggccatgga atctgccaag      540
gagactcgct actgtgcagt gtgcaatgac tatgcctcag gctaccatta tggagtttgg      600
tcttgcgagg gctgtaaggc cttcttcaag agaagtattc aaggacataa tgactacatg      660
tgtccagcta ccaaccagtg cacaattgat aagaacagga ggaagagctg tcaggcctgc      720
cggctacgca gtgctacga agtgggcatg atgaaggggg ggatacggaa agaccggaga      780
```

-continued

| | | |
|---|---|---|
| ggagggagaa tgttgaagca caagcgccag agagatgatg gagagggcag gaatgaagcg | 840 | |
| gtgcccctg gagacatgag atctgccaac ctttggccaa gccctctctt gattaaacac | 900 | |
| actaagaaga acagcccggt cttgtccctg acagccgacc agatgatcag tgccttgttg | 960 | |
| gaggctgagc cccccataat ctattccgag tatgatccta ccagacccct cagtgaggct | 1020 | |
| tcaatgatgg gcttgctgac caacctcgca gacaggagc tggtacacat gatcaactgg | 1080 | |
| gcaaagaggg tgccaggatt tttggattta agcctccatg atcaagtgca tcttctggaa | 1140 | |
| tgtgcctggc tagagatcct catgattggt cttgtctggc gctccatgga gcacccaggg | 1200 | |
| aagctcctgt ttgctcctaa cttgctcctg acaggaacc agggcaagtg tgtcgaggga | 1260 | |
| atggtggaga tctttgacat gttgctggct acatcatctc gcttccgtat gatgaatctc | 1320 | |
| cagggagagg agtttgtgtg cctcaaatcc atcattttgc ttaattctgg agtgtacacg | 1380 | |
| tttctgtcca gcaccctgaa gtctctggaa gagaaggacc atatccaccg tgtcctggac | 1440 | |
| aagatcacag acaccttgat ccacctgatg gccaaagcgg gcctgactct gcagcagcag | 1500 | |
| caccggcgtc tcgcgcagct cctcctcatc ctgtctcact tcaggcacat gagtaacaaa | 1560 | |
| ggcatggagc atctgtacaa catgaagtgc aagaacgtgg tgcccctcta tgacctgctg | 1620 | |
| ctggagatgc tggacgccca ccgcctgcac gccccaacca accttggggg cccaccccg | 1680 | |
| gaggacatga gccagagcca gctggccacc tcgggctcaa ctccatcgca ttccttgcaa | 1740 | |
| atgtattaca tcacagggga ggcggagaac ttccccacca caatctga | 1788 | |

<210> SEQ ID NO 25
<211> LENGTH: 1759
<212> TYPE: DNA
<213> ORGANISM: Polyxenus fasciculatus

<400> SEQUENCE: 25

| | | |
|---|---|---|
| tcatatgctt gtctcaaaga ttaagccatg catgtgtaag tacacaccat cctaaggtga | 60 | |
| gaccgcgaat ggctcattaa atcagttatg gttcattaga tgagtccaat cctacttgga | 120 | |
| taactgtggc aattctagag ctaatacacg cctccaagct ctgacctatc gggacgagcg | 180 | |
| cttttattag accaagacca atcgggcttc ggtccgtttc ctttggtgac tctgaataac | 240 | |
| cttttgaaga tcgcacggtc tcgaaccggc gatgcatctt tcaaatgtct gccttatcaa | 300 | |
| ctgtcgatgg taagttatgc gcttaccatg gttgtaacgg gtaacggaga atcagggttc | 360 | |
| gattccggag agggagcctg agaaacggct gccacatcca aggaaggcag caggcacgca | 420 | |
| aattacccac tcccggcacg gggaggtagt gacgaaaaat aacgatgcgg gactcttccg | 480 | |
| aggccccgta atcggaatga gtacacttta aatcctttaa cgaggatcaa ttggagggca | 540 | |
| agtctggtgc cagcagccgc ggtaattcca gctccaatag cgtatactaa agttgttgcg | 600 | |
| gctaaaaagc tcgtagttgg atttcagtcg taggccggtg gtccaccgcc cggtggctac | 660 | |
| tgcctggtct ggacaccttg ccagctctcc ggcgatgctc ttgaccgggt gtcgttggtg | 720 | |
| gctggaacgt ttactttgaa aaaattagag tgctctaagc aggtgctatc ggcttgaata | 780 | |
| acacagcatg gaataatgga acacgacctt ggttctgttc tgttggtctt tggaagccaa | 840 | |
| ggtaatgatt aatagggacg gacggggggca ttcgtattgc gacgctagag gtgaaattct | 900 | |
| tggaccgtcg caagacgaac tactgcgaac gcatttgcca agaacgtttt cattaatcaa | 960 | |
| gaacgaaagt cagaggttcg aaggcgatca gataccgccc tagttctgac cataaacaat | 1020 | |
| gccaaccagc gatccgccgg agttactccc atgactcggc gggcagcttc cgggaaacca | 1080 | |
| aagtgtttgg gttccggggg aagtatggtt gcaaagctga aacttaaagg aattgacgga | 1140 | |

```
agggcaccac caggagtgga gcctgcggct taatttgact caacacggga cacctcaccc    1200
gccccggaca ccggaaggat tgacagactg agagctcttt cttgattcgg tgggtggtgg    1260
tgcatggccg ttcttagttg gtggagcgat ctgtctggtt aattccgata acgaacgaga    1320
ctctagccta ctaactagcc agtcgatcat ttgtcggctg ttcttcttag agggataagc    1380
ggcttttagc cgcatgagat tgagcaataa caggtctgtg atgcccttag atgtccggga    1440
ccgcacgcgc gctacactga tgttgtcagc ttgtttctcc ccttgtccga gaggaccggg    1500
taatccgctg aaccaccttc gtgatagggg tcggggtttg aaattatccc ccgtgaacga    1560
ggaattccca gtaagcgcga gtcataagct cgtgttgatt acgtccctgc cctttgtaca    1620
caccgcccgt cgctactacc gattgaatga tttagtgagg tcttcggact gaggcccggc    1680
gaagcttgct ttgccgacgc tttggaaaga tgatcgaact tgatcattta gaggaagtaa    1740
aagtcgtaac aaggtttcc                                                 1759

<210> SEQ ID NO 26
<211> LENGTH: 7
<212> TYPE: DNA
<213> ORGANISM: Human

<400> SEQUENCE: 26 ccgcccc                                                                 7

<210> SEQ ID NO 27
<211> LENGTH: 228
<212> TYPE: DNA
<213> ORGANISM: Polyxenus lagurus

<400> SEQUENCE: 27
tcatttgtcg gctgttcttc ttagagggat aagcggcttt tagccgcatg agattgagca      60
ataacaggtc tgtgatgccc ttagatgtcc gggaccgcac gcgcgctaca ctgatgttat     120
cagcttgttt ctcccccttgt ccgagaggac cgggtaatcc gctgaaccac cttcgtgata    180
gggatcgggg tttgaaatta tcccccgtga acgaggaatt cccagtaa                  228

<210> SEQ ID NO 28
<211> LENGTH: 2842
<212> TYPE: DNA
<213> ORGANISM: Human

<400> SEQUENCE: 28
acacgcacct catcgacctg gtaaccaatg agattatcac ccaaggacct ccagtggact       60
ggaatgacat tgctggtctc gacctggtga aggctgtcat taaagaggag gttttatggc     120
cagtgttgag gtcagacgcg ttcagtggac tgacggcctt acctcggagc atccttttat     180
ttggacctcg ggggacaggc aaaacattat tgggcagatg catcgctagt cagctggggg     240 ccacatttttt caaaattgcc ggttctggac tagtcgccaa gtggttagga gaagcagaga     300
aaattatcca tgcctctttt cttgtggcca ggtgtcgcca gccctcggtg atttttgtta     360
gtgacattga catgcttctc tcctctcaag tgaatgagga acatagtcca gtcagtcgga     420
tgagaaccga atttctgatg caactggaca ctgtactaac ttcggctgag gaccaaatcg     480
tagtaatttg tgccaccagt aaaccagaag aaatagatga atcccttcgg aggtacttca     540
tgaaacgact tttaatccca cttcctgaca gcacagcgag gcaccagata atagtacaac     600
tgctctcaca gcacaattac tgtctcaatg acaaggagtt tgcactgctc gtccagcgca     660
```

```
cagaaggctt ttctggacta gatgtggctc atttgtgtca ggaagcagtg gtgggccccc      720
tccatgccat gccagccaca gacctttcag ccattatgcc cagccagttg aggcccgtta      780
catatcaaga ctttgaaaat gctttctgca agattcagcc tagcatatct caaaaggagc      840
ttgatatgta tgttgaatgg aacaaaatgt ttggttgcag tcagtgataa cttcttaga       900 aaaaaaaaat gtaatgaatg ttggcacaca cataaaaac ctgctacata gggaatagag       960
cccctttcca gtagagttta aattgcaaag ggtactgggg aagatgacga ttaagttgca     1020
tctttagagt cagggtagat ttggaggaaa agtgcatcaa atgagagctt ctgatttgaa     1080
agccccagat gacagaaagc atatgtggat gctcagttct gttcaagcta gacaacactc     1140
accaaggagc aaggtgcaag tgtgttgatt tcagaaggac atgaacctcg tgtgttgatt     1200
ccattctgct gttctcgaga tttagttgct gtcaagtgcc tggagtggtg ctttatttt      1260 tgtttgcctc acaattacat tggtggcatg tgctaatata aagagcttta acttcaaaca     1320
ttattggact aaagagatga acagttgtgt tatgacagaa aaccagattt ttgccatttt     1380
aagagcaaca gtattcctca atcctgtctg ttctgcagta ttaagctaag aacaggtaaa     1440
acagggtaac ggtaatctgg accttaattt ctgcagttca tttctttaa tgttcttgtc      1500 tgcaaaaact caggaaagtg attgtgattt gtacagtacc tcaaggaat gtgttgaaag      1560 cactatgtac tgctgagagt aataggatag gcttcaatgt tactttatat taaaatgtat     1620
gtttacctca acaattggaa aatagcaagg aaaattactt tgaatgtatc cagaaaaata    1680
ctgaagtgtg atacaactga atatttacag tttaaagtag aaatggaagg atttttttaa    1740
gttcttttac taattatggg gaattaacca gagcagaata attctttatg tcaataactg    1800
caagagttct tagtacattg ctccttgata attaagtgaa aatgttctta aaaggtacac    1860
tggttaattg aaagctactt attcagtttg tgttagtgtc tagacctgtc agccacaaga    1920
cctgtttagg accctgaaag tcacagtacc taaaaactat gactgccttt ttattgcata    1980
ggtggtagtg gtggtgatgg tggtggtagt ttgcaagtta tctcttaaaa ctgctgggaa    2040
tggtgtcatt ctattcacta atctagctta tagacttgcc gtgctgtttg atagaatgca    2100
gaggatagca accaaaacaa atacacaaat aaataaaaac aaaaaccaac caacaaacca    2160
acttacatac atatatatat atccacaaag aacctctcca tctcctcccc ttcttttga    2220 ctccactctt gtcagtgcaa ttttgcttct cattttgaaa tctgggctgt agtgctcctg    2280
ctttatttct acctcagttt tgttacattt ctccttggaaa gtaaagtaga aaattggaag    2340
tggacacaca cactgcaatg tagcttgcca aacatgttac tttgttttct tccatctttc    2400
accgtaaatc tagtttccaa agacatcagc atttgtgctt acttccacct cagtctacca    2460
gccccacccc tacccatggc ataagtgcca tttttcttaa tttcctattt ttctcctgct    2520
ctctgtcaag ttgttctttg tatcctttaa tgctttatgt gcaacctttc attgatagtg    2580
ggctgatgtt tggcaatgct tctgaactgt cacagagcag gctgtagctt ccacagcca    2640 ctgcccatgc ataagcagaa cagcctggcc ttttgaatgt attttcctgg gttttttcc     2700 ccttttcttt tttagtttta gagatgcagt aacaaaactg ttgcaaagca ctggcatttt    2760
atgtattcaa taaataagtg atgtacattt ttaaaaaaat ttaaataaat gcaatgagaa    2820
gccccaaaaa aaaaaaaaaa aa                                              2842
```

<210> SEQ ID NO 29
<211> LENGTH: 381
<212> TYPE: PRT
<213> ORGANISM: violet cress

<400> SEQUENCE: 29

```
Ala Met Val Gln His Gln Pro Pro Gln Val Pro Pro Pro Pro Pro Ser
1               5                   10                  15
Gln Gln Ser Pro Val Thr Pro Leu Thr Ala Ala Phe Gly Met Arg Leu
            20                  25                  30
Gly Gly Leu Glu Gly Leu Phe Gly Pro Tyr Gly Ile Arg Phe Tyr Thr
        35                  40                  45
Ala Ala Lys Ile Ala Glu Leu Gly Phe Thr Ala Ser Thr Leu Val Gly
    50                  55                  60
Met Lys Asp Glu Glu Leu Glu Asp Met Met Asn Ser Leu Ser His Ile
65                  70                  75                  80
Phe Arg Trp Glu Leu Leu Val Gly Glu Arg Tyr Gly Ile Lys Ala Ala
                85                  90                  95
Val Arg Ala Glu Arg Arg Leu Gln Glu Glu Glu Asp Glu Ser
            100                 105                 110
Ser Arg Arg Arg His Leu Leu Leu Ser Ala Ala Gly Asp Ser Gly Thr
        115                 120                 125
His His Ala Leu Asp Ala Leu Ser Gln Glu Asp Asp Trp Thr Gly Leu
    130                 135                 140
Ser Glu Glu Pro Met His Gln Asp Gln Thr Asp Ala Ala Gly Asn Gly
145                 150                 155                 160
Gly Phe Gly Gly Tyr Leu Glu Ser Ser Val His Gly Lys Met Lys Lys
                165                 170                 175
His Gln Pro Arg Arg Lys Lys Pro Leu Val Leu Thr Ser Val Glu
            180                 185                 190
Thr Asp Asp Asp Gly Asn Asp Asn Glu Asp Asp Gly Met Asp Asn
        195                 200                 205
Gly Asn Gly Gly Ile Gly Leu Gly Thr Glu Arg Gln Arg Glu His Pro
    210                 215                 220
Phe Ile Val Thr Glu Pro Gly Glu Val Ala Arg Gly Lys Lys Asn Gly
225                 230                 235                 240
Leu Asp Tyr Leu Phe His Leu Tyr Glu Gln Cys Arg Glu Phe Leu Leu
                245                 250                 255
Gln Val Gln Thr Ile Ala Lys Asp Arg Gly Glu Lys Cys Pro Thr Lys
            260                 265                 270
Val Thr Asn Gln Val Phe Arg Tyr Ala Lys Lys Ser Gly Ala Ser Tyr
        275                 280                 285
Ile Asn Lys Pro Lys Met Arg His Tyr Val His Cys Tyr Ala Leu His
    290                 295                 300
Cys Leu Asp Glu Glu Ala Ser Asn Ala Leu Arg Arg Ala Phe Lys Glu
305                 310                 315                 320
Arg Gly Glu Asn Val Gly Ser Trp Arg Gln Ala Cys Tyr Lys Pro Leu
                325                 330                 335
Val Asn Ile Ala Cys Arg His Gly Trp Asp Ile Asp Ala Val Phe Asn
            340                 345                 350
Ala His Pro Arg Leu Ser Ile Trp Tyr Val Pro Thr Lys Leu Arg Gln
        355                 360                 365
Leu Cys His Leu Glu Arg Asn Asn Ala Val Ala Ala
    370                 375                 380
```

<210> SEQ ID NO 30
<211> LENGTH: 595
<212> TYPE: PRT

<213> ORGANISM: hamster

<400> SEQUENCE: 30

```
Met Thr Met Thr Leu His Thr Lys Ala Ser Gly Met Ala Leu Leu His
1               5                   10                  15

Gln Ile Gln Gly Asn Glu Leu Glu Pro Leu Ser Arg Pro Gln Leu Lys
            20                  25                  30

Met Pro Leu Glu Arg Ala Leu Ser Glu Val Tyr Val Asp Ser Ser Lys
        35                  40                  45

Pro Ala Met Phe Asn Tyr Pro Glu Gly Ala Ala Tyr Glu Phe Asn Ala
    50                  55                  60

Ala Thr Ala Pro Ala Pro Val Tyr Gly Gln Thr Gly Ile Ala Tyr Gly
65                  70                  75                  80

Ser Gly Ser Glu Ala Thr Ala Phe Gly Ser Asn Ser Leu Gly Leu Phe
                85                  90                  95

Pro Gln Leu Asn Ser Val Ser Pro Ser Pro Leu Met Leu Leu His Pro
            100                 105                 110

Pro Pro Pro Gln Leu Ser Pro Phe Leu His Pro His Gly Gln Gln Val
        115                 120                 125

Pro Tyr Tyr Leu Glu Asn Glu Pro Ser Ala Tyr Ala Val Arg Asp Ser
    130                 135                 140

Gly Pro Pro Ala Phe Tyr Arg Ser Asn Ser Asp Asn Arg Arg Gln Ser
145                 150                 155                 160

Gly Arg Glu Arg Leu Ser Ser Ser Glu Lys Gly Ser Met Ala Met
                165                 170                 175

Glu Ser Val Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Leu Glu Gly Arg Asn Asp Met Gly Pro Ser Gly Asp Met Arg Ala
        275                 280                 285

Thr Asn Leu Trp Pro Ser Pro Leu Val Ile Lys His Thr Lys Lys Asn
    290                 295                 300

Ser Pro Ala Leu Ser Leu Thr Ala Asp Gln Met Val Ser Ala Leu Leu
305                 310                 315                 320

Asp Ala Glu Pro Pro Leu Ile Tyr Ser Glu Tyr Asp Pro Ser Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Gly
        355                 360                 365

Asp Leu Asn Leu His Asp Gln Val His Leu Leu Glu Cys Ala Trp Leu
    370                 375                 380

Glu Ile Leu Met Ile Gly Leu Ile Trp Arg Ser Met Glu His Pro Gly
385                 390                 395                 400
```

-continued

```
Lys Leu Leu Phe Ala Pro Asn Leu Leu Leu Asp Arg Asn Gln Gly Lys
            405                 410                 415
Cys Val Glu Gly Met Val Glu Ile Phe Asp Met Leu Leu Ala Thr Ser
            420                 425                 430
Ala Arg Phe Arg Met Met Asp Leu Gln Gly Glu Glu Phe Val Cys Leu
            435                 440                 445
Lys Ser Ile Ile Leu Leu Asn Ser Gly Val Tyr Thr Phe Leu Ser Ser
            450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Arg Arg Leu Ala Gln Leu Leu Leu Ile Leu Ser
            500                 505                 510
His Ile Arg His Met Ser Asn Lys Gly Met Glu His Leu Tyr Asn Met
            515                 520                 525
Lys Cys Lys Asn Val Val Pro Phe Tyr Asp Leu Leu Leu Glu Met Leu
            530                 535                 540
Asp Ala His Arg Leu His Thr Pro Val Ser Arg Met Gly Val Ser Pro
545                 550                 555                 560
Glu Glu Pro Ser Gln Ser Gln Leu Thr Thr Asn Ser Thr Ser Ser
                565                 570                 575
His Ser Leu Gln Thr Tyr Tyr Ile Pro Ser Glu Ala Glu Ser Phe Pro
            580                 585                 590
Asn Thr Ile
        595

<210> SEQ ID NO 31
<211> LENGTH: 595
<212> TYPE: PRT
<213> ORGANISM: pig

<400> SEQUENCE: 31

Met Thr Met Thr Leu His Thr Lys Ala Ser Gly Met Ala Leu Leu His
1               5                   10                  15
Gln Ile Gln Ala Asn Glu Leu Glu Pro Leu Asn Arg Pro Gln Leu Lys
            20                  25                  30
Ile Pro Leu Glu Arg Pro Leu Gly Glu Val Tyr Val Asp Ser Ser Lys
            35                  40                  45
Pro Ala Val Tyr Asn Tyr Pro Glu Gly Ala Ala Tyr Asp Phe Asn Ala
            50                  55                  60
Ala Ala Ala Ala Ser Ala Pro Val Tyr Gly Gln Ser Gly Leu Ala Tyr
65                  70                  75                  80
Gly Pro Gly Ser Glu Ala Ala Ala Phe Gly Ala Asn Gly Leu Gly Gly
                85                  90                  95
Phe Gln Pro Leu Asn Ser Val Ser Pro Ser Pro Leu Val Leu Leu His
            100                 105                 110
Pro Pro Pro Gln Leu Ser Pro Phe Leu His Pro His Gly Gln Gln Val
            115                 120                 125
Pro Tyr Tyr Leu Glu Asn Glu Pro Ser Gly Tyr Ala Val Arg Glu Ala
            130                 135                 140
Gly Pro Pro Ala Phe Tyr Arg Pro Asn Ser Asp Asn Arg Arg Gln Gly
145                 150                 155                 160
Gly Arg Glu Arg Leu Ala Ser Thr Ser Asp Lys Gly Ser Met Ala Met
                165                 170                 175
```

-continued

```
Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
        210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Asn Glu Ala Val Pro Pro Gly Asp Met Arg Ser
            275                 280                 285

Ala Asn Leu Trp Pro Ser Pro Leu Leu Ile Lys His Thr Lys Lys Asn
        290                 295                 300

Ser Pro Val Leu Ser Leu Thr Ala Asp Gln Met Ile Ser Ala Leu Leu
305                 310                 315                 320

Glu Ala Glu Pro Pro Ile Ile Tyr Ser Glu Tyr Asp Pro Thr Arg Pro
                325                 330                 335

Leu Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Leu
        355                 360                 365

Asp Leu Ser Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
        450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Arg Arg Leu Ala Gln Leu Leu Leu Ile Leu Ser
            500                 505                 510

His Phe Arg His Met Ser Asn Lys Gly Met Glu His Leu Tyr Asn Met
        515                 520                 525

Lys Cys Lys Asn Val Val Pro Leu Tyr Asp Leu Leu Leu Glu Met Leu
        530                 535                 540

Asp Ala His Arg Leu His Ala Pro Thr Asn Leu Gly Gly Pro Pro Pro
545                 550                 555                 560

Glu Asp Met Ser Gln Ser Gln Leu Ala Thr Ser Gly Ser Thr Pro Ser
                565                 570                 575

His Ser Leu Gln Met Tyr Tyr Ile Thr Gly Glu Ala Glu Asn Phe Pro
            580                 585                 590
```

```
Thr Thr Ile
        595

<210> SEQ ID NO 32
<211> LENGTH: 171
<212> TYPE: PRT
<213> ORGANISM: Human

<400> SEQUENCE: 32

Met Leu Leu Ser Ser Gln Val Asn Glu Glu His Ser Pro Val Ser Arg
1               5                   10                  15

Met Arg Thr Glu Phe Leu Met Gln Leu Asp Thr Val Leu Thr Ser Ala
            20                  25                  30

Glu Asp Gln Ile Val Val Ile Cys Ala Thr Ser Lys Pro Glu Glu Ile
        35                  40                  45

Asp Glu Ser Leu Arg Arg Tyr Phe Met Lys Arg Leu Leu Ile Pro Leu
    50                  55                  60

Pro Asp Ser Thr Ala Arg His Gln Ile Ile Val Gln Leu Leu Ser Gln
65                  70                  75                  80

His Asn Tyr Cys Leu Asn Asp Lys Glu Phe Ala Leu Leu Val Gln Arg
                85                  90                  95

Thr Glu Gly Phe Ser Gly Leu Asp Val Ala His Leu Cys Gln Glu Ala
            100                 105                 110

Val Val Gly Pro Leu His Ala Met Pro Ala Thr Asp Leu Ser Ala Ile
        115                 120                 125

Met Pro Ser Gln Leu Arg Pro Val Thr Tyr Gln Asp Phe Glu Asn Ala
    130                 135                 140

Phe Cys Lys Ile Gln Pro Ser Ile Ser Gln Lys Glu Leu Asp Met Tyr
145                 150                 155                 160

Val Glu Trp Asn Lys Met Phe Gly Cys Ser Gln
                165                 170

<210> SEQ ID NO 33
<211> LENGTH: 20
<212> TYPE: DNA
<213> ORGANISM: Artificial Sequence
<220> FEATURE:
<223> OTHER INFORMATION: Estrogen Response Element

<400> SEQUENCE: 33
gctctaagaa gaacagcctg                                          20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gctctaagag gaacagcctg                                          20

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
agagagatga tggggagggc aggggtgaag                               30
```

```
<210> SEQ ID NO 36
<211> LENGTH: 6
<212> TYPE: DNA
<213> ORGANISM: Artificial Sequence
<220> FEATURE:
<223> OTHER INFORMATION: Estrogen Response Element

<400> SEQUENCE: 36 aggtca                                                                     6

<210> SEQ ID NO 37
<211> LENGTH: 6
<212> TYPE: DNA
<213> ORGANISM: Artificial Sequence
<220> FEATURE:
<223> OTHER INFORMATION: Estrogen Response Element

<400> SEQUENCE: 37 tgacct                                                                     6

<210> SEQ ID NO 38
<211> LENGTH: 13
<212> TYPE: DNA
<213> ORGANISM: Artificial Sequence
<220> FEATURE:
<223> OTHER INFORMATION: Estrogen Response Element
<220> FEATURE:
<221> NAME/KEY: misc_feature
<222> LOCATION: (1)..(13)
<223> OTHER INFORMATION: n equals unknown

<400> SEQUENCE: 38
ggtcannntg acc                                                            13

<210> SEQ ID NO 39
<211> LENGTH: 13
<212> TYPE: DNA
<213> ORGANISM: Artificial Sequence
<220> FEATURE:
<223> OTHER INFORMATION: Estrogen Response Element
<220> FEATURE:
<221> NAME/KEY: misc_feature
<222> LOCATION: (1)..(13)
<223> OTHER INFORMATION: n equals unknown

<400> SEQUENCE: 39
aatcannntg act                                                            13

<210> SEQ ID NO 40
<211> LENGTH: 5
<212> TYPE: DNA
<213> ORGANISM: Artificial Sequence
<220> FEATURE:
<223> OTHER INFORMATION: Estrogen Response Element

<400> SEQUENCE: 40 ggtca                                                                      5

<210> SEQ ID NO 41
<211> LENGTH: 5
<212> TYPE: DNA
<213> ORGANISM: Artificial Sequence
<220> FEATURE:
<223> OTHER INFORMATION: Estrogen Response Element

<400> SEQUENCE: 41
``` tggtc                                                              5

<210> SEQ ID NO 42
<211> LENGTH: 5
<212> TYPE: DNA
<213> ORGANISM: Artificial Sequence
<220> FEATURE:
<223> OTHER INFORMATION: Estrogen Response Element

<400> SEQUENCE: 42 tgacc                                                              5

<210> SEQ ID NO 43
<211> LENGTH: 22
<212> TYPE: DNA
<213> ORGANISM: Artificial Sequence
<220> FEATURE:
<223> OTHER INFORMATION: Estrogen Response Element

<400> SEQUENCE: 43
attcgatcag ggcggggcga gc                                          22

<210> SEQ ID NO 44
<211> LENGTH: 27
<212> TYPE: DNA
<213> ORGANISM: Artificial Sequence
<220> FEATURE:
<223> OTHER INFORMATION: Estrogen Response Element
<220> FEATURE:
<221> NAME/KEY: misc_feature
<222> LOCATION: (1)..(27)
<223> OTHER INFORMATION: n equals unknown

<400> SEQUENCE: 44
gggcannnnn nnnnnnnnnn nggcggg                                     27

<210> SEQ ID NO 45
<211> LENGTH: 31
<212> TYPE: DNA
<213> ORGANISM: Artificial Sequence
<220> FEATURE:
<223> OTHER INFORMATION: Estrogen Response Element
<220> FEATURE:
<221> NAME/KEY: misc_feature
<222> LOCATION: (1)..(31)
<223> OTHER INFORMATION: n equals unknown

<400> SEQUENCE: 45
ggtcannnnn nnnnnnnnnn nnnnnnggcg g                                31

<210> SEQ ID NO 46
<211> LENGTH: 23
<212> TYPE: DNA
<213> ORGANISM: Artificial Sequence
<220> FEATURE:
<223> OTHER INFORMATION: Estrogen Response Element
<220> FEATURE:
<221> NAME/KEY: misc_feature
<222> LOCATION: (1)..(23)
<223> OTHER INFORMATION: n equals unknown

<400> SEQUENCE: 46
gggccgggnn nnnnnnnngg tca                                         23

<210> SEQ ID NO 47
<211> LENGTH: 5
<212> TYPE: DNA
<213> ORGANISM: Artificial Sequence -continued

```
<220> FEATURE:
<223> OTHER INFORMATION: Estrogen Response Element

<400> SEQUENCE: 47 gggca                                                              5

<210> SEQ ID NO 48
<211> LENGTH: 5
<212> TYPE: DNA
<213> ORGANISM: Artificial Sequence
<220> FEATURE:
<223> OTHER INFORMATION: Estrogen Response Element

<400> SEQUENCE: 48 ggtaa                                                              5

<210> SEQ ID NO 49
<211> LENGTH: 13
<212> TYPE: DNA
<213> ORGANISM: Artificial Sequence
<220> FEATURE:
<223> OTHER INFORMATION: Estrogen Response Element
<220> FEATURE:
<221> NAME/KEY: misc_feature
<222> LOCATION: (1)..(13)
<223> OTHER INFORMATION: n equals unknown

<400> SEQUENCE: 49
ggtcannntg ccc                                                    13
```

METHODS AND COMPOSITIONS IN BREAST CANCER DIAGNOSIS AND THERAPEUTICS

This application claims priority to U.S. Ser. No. 60/304,018, filed Jul. 9, 2001, U.S. Ser. No. 60/262,990, filed Jan. 19, 2001, and U.S. Ser. No. 10/052,092, filed Jan. 18, 2002, all of which are incorporated herein in their entirety.

This invention was developed with funds from the United States Government. The United States Government has certain rights in the invention.

FIELD OF THE INVENTION

The present invention is directed to the fields of cancer and molecular genetics. Specifically, the present invention is directed to the determination of susceptibility to breast cancer and the diagnosis of invasive breast cancer. More specifically, the present invention is directed to a mutation in estrogen receptor alpha (ER) and its association with breast cancer.

BACKGROUND OF THE INVENTION

Invasive breast cancer (IBC) is one of the most common and lethal malignant neoplasms affecting women, especially in Western cultures. The majority of IBCs are thought to develop over long periods of time from certain preexisting benign lesions. There are many types of benign lesions in the human breast, and only a few appear to have significant premalignant potential. The most important premalignant lesions recognized today are referred to as a typical ductal hyperplasia (ADH), a typical lobular hyperplasia (ALH), ductal carcinoma in situ (DCIS), and lobular carcinoma in situ (LCIS). Although DCIS and LCIS possess some malignant properties, such as loss of growth control, they lack the ability to invade and metastasize and, in this sense, are premalignant.

A skilled artisan is aware that investigation of the role of the estrogen receptor in carcinomas is described by Watts et al., J. Steroid Biochem. Molec. Biol. 41(3), 529 (1992); Scott et al., J. Clinic. Invest. 88, 700 (1991); Ince et al., J. Bio. Chem. 268, 14026 (1993); Fuqua et al., Can. Res. 52, 43 (1992); McGuire et al., Mol. Endocr. 5, 1571 (1991); Castles et al., Can. Res. 53, 5934 (1993); and Weigel and deConinck, Can. Res. 53, 3472 (1993). Furthermore, description of the estrogen receptor mRNA may be found in Keaveney et al., J. Mol. Endocr. 6, 111 (1991); Green et al., Nature 320, 134 (1986); White et al., Mol. Endocr. 1, 735 (1987); and Piva et al., J. Steroid Biochem. Molec. Biol. 46, 531 (1993).

U.S. Pat. No. 6,162,606 is directed to identification of defective estrogen receptors associated with the classification of breast tumors which are responsive to or resistant to hormone therapy. Similarly, U.S. Pat. No. 5,563,035 regards monitoring the level of ERF-1, a transcriptional regulator of expression of the estrogen receptor, as being indicative of the response of a breast tumor to various therapies.

There is epidemiological evidence that there are genetic alterations that are closely associated with morphological tumor progression, such as is found in studies in colon carcinoma (Vogelstein and Kinzler, 1993). In this model (Dupont and Page, 1985), breast cancer is hypothesized as evolving from normal ductal epithelium to typical hyperplasia, to a typical hyperplasia, to carcinoma in situ, to invasive carcinoma, and finally to metastatic carcinoma. Recent data also suggests that the majority of hyperplasias share molecular alterations with invasive disease in the same breast (O'Connell et al., 1998), providing genetic evidence that they are related. Unlike colon cancer, very little is known about the specific molecular changes that are associated with the earliest stages of breast cancer evolution. However, it is likely that estrogens are important, since they are potent mitogens for normal breast epithelial cells, and it is believed that the duration of estrogen exposure to the breast epithelium is a significant risk factor for breast cancer development. It is also generally agreed that expression of the estrogen receptor (ER) is relatively low in normal breast epithelium, but is higher in certain premalignant lesions (e.g. typical hyperplasias) (van Agthoven et al., 1994).

Anandappa et al. (2000) detected no sequencing variants, such as single base change mutations, in ER from a panel of human primary breast cancer specimens. However, Zhang et al. (1997) identified an ER mutant in metastatic breast cancer which had a constitutive transactivation function independent of estradiol-binding.

Current human breast cancer management strategies utilize ER status as a predictive factor (McGuire, 1978; Burstein, 1982; Brooks et al., 1980; Degenshein et al., 1980; McGuire et al., 1975; McGuire, 1987; Elledge and McGuire, 1993; Gelbfish et al., 1988; Williams et al., 1987; Kohail et al., 1985; Donegan, 1992; Millis, 1980; McCarty et al., 1980), although none regard the specific mutation of the present invention. Present human breast tumor tissue specimens are subjected to both ligand-binding studies and immunohistochemical analyses to determine ER status (King et al., 1979; Shousha et al., 1989; Shousha et al., 1990). Thus, as has been acknowledged (see, for example, Roger et al., 2000), the art presently lacks a molecular marker for breast tissue, such as a premalignant lesion, which is at risk for breast cancer, particularly for invasive breast cancer, and also lacks a marker for the purpose of improving approaches to risk prediction and treatment strategies. Identification of a specific molecular marker for an altered ER as an early event in breast cancer evolution would be a significant advance in the field and would provide an ideal diagnosis tool for the detection of susceptibility to breast cancer and its subsequent prevention.

SUMMARY OF THE INVENTION

In an embodiment of the present invention there is an isolated estrogen receptor alpha nucleic acid sequence comprising an A908G mutation.

In another embodiment of the present invention there is an isolated estrogen receptor alpha amino acid sequence comprising a K303R substitution.

In an additional embodiment of the present invention there is a method of detecting susceptibility to development of breast cancer in an individual, comprising the steps of obtaining a sample from a breast of the individual, wherein the sample comprises a cell having an estrogen receptor alpha nucleic acid sequence; and assaying the nucleic acid sequence for an A908G mutation, wherein the presence of the mutation in the nucleic acid sequence indicates the individual has breast cancer. In a specific embodiment, the sample is from a premalignant lesion of the breast.

In an additional embodiment of the present invention there is a method of detecting susceptibility to development of invasive breast cancer in an individual, comprising the steps of obtaining a sample from a breast of the individual; and assaying an estrogen receptor alpha nucleic acid sequence from a cell of the sample for an A908G mutation, wherein the presence of the mutation in the nucleic acid sequence detects susceptibility of the premalignant lesion to develop into the invasive breast cancer. In a specific embodiment, the sample is from a premalignant lesion of the breast.

In an additional embodiment of the present invention there is a method of detecting susceptibility to development of invasive breast cancer from a premalignant lesion in a breast, comprising the steps of obtaining a sample from the premalignant lesion; dissecting the sample to differentiate hyperplastic cells in the sample from nonhyperplastic cells; and assaying an estrogen receptor alpha nucleic acid sequence from the hyperplastic cell of the sample for an A908G mutation, wherein the presence of the mutation in the nucleic acid sequence detects susceptibility of the premalignant lesion to develop into the invasive breast cancer. In a specific embodiment, the dissection step comprises removal of the hyperplastic cells from the sample by manual manipulation or by laser capture microdissection. In another specific embodiment, the sample is obtained by biopsy. In a specific embodiment, the assaying step comprises sequencing, single stranded conformation polymorphism, mismatch oligonucleotide mutation detection, or a combination thereof. In an additional specific embodiment, the assaying step is by antibody detection with antibodies to the A908G mutation of the estrogen receptor alpha nucleic acid sequence or is by antibody detection with antibodies to an acetylated estrogen receptor alpha amino acid sequence.

In an additional embodiment of the present invention there is a method of classifying breast cancer in an individual, comprising the steps of obtaining from the individual a sample from the breast, wherein the sample contains a cancer cell; and assaying an estrogen receptor alpha nucleic acid sequence from the cell of the sample for an A908G mutation, wherein the presence of the mutation identifies the breast cancer to be invasive breast cancer. In a specific embodiment, the sample is obtained by biopsy. In another specific embodiment, the assaying step is selected from the group consisting of sequencing, single stranded conformation polymorphism, mismatch oligonucleotide mutation detection, and a combination thereof. In an additional specific embodiment the assaying step is by antibody detection with antibodies to the A908G mutation of the estrogen receptor alpha nucleic acid sequence or by antibody detection with antibodies to an acetylated estrogen receptor alpha amino acid sequence.

In another embodiment of the present invention there is a method of diagnosing breast cancer in an individual, comprising the steps of obtaining a sample from a breast of the individual, wherein the sample comprises a cell having an estrogen receptor alpha nucleic acid sequence; and assaying the nucleic acid sequence for an A908G mutation, wherein the presence of the mutation in the nucleic acid sequence indicates the individual has breast cancer.

In another embodiment of the present invention there is a method of diagnosing breast cancer in an individual, comprising the steps of obtaining a sample from a breast of the individual; dissecting the sample to differentiate a cell suspected of being cancerous from a noncancerous cell; and assaying the cell suspected of being cancerous for an A908G mutation in an estrogen receptor alpha nucleic acid sequence, wherein the presence of the mutation in the nucleic acid sequence indicates the individual has breast cancer. In a specific embodiment, the dissection step comprises removal of the cells suspected of being cancerous from the sample by manual manipulation or by laser capture microdissection. In a specific embodiment, the sample is obtained by biopsy. In another specific embodiment, the assaying step is selected from the group consisting of sequencing, single stranded conformation polymorphism, mismatch oligonucleotide mutation detection, and a combination thereof. In an additional specific embodiment, the assaying step is by antibody detection with antibodies to the A908G mutation of the estrogen receptor alpha nucleic acid sequence or is by antibody detection with antibodies to an acetylated estrogen receptor alpha amino acid sequence.

In another embodiment of the present invention there is a kit for diagnosing an A908G mutation in an estrogen receptor alpha nucleic acid sequence, comprising at least one primer selected from the group consisting of SEQ ID NO:15, SEQ ID NO:16, SEQ ID NO:17, SEQ ID NO:18, SEQ ID NO:33, SEQ ID NO:34, and SEQ ID NO:35. In one embodiment, the primers are extendable. In an alternative embodiment, the primers are nonextendable.

In another embodiment of the present invention there is a monoclonal antibody that binds immunologically to an acetylated estrogen receptor alpha amino acid sequence, or an antigenic fragment thereof.

In another embodiment of the present invention there is a monoclonal antibody that binds immunologically to an A908G mutation in an estrogen receptor alpha nucleic acid sequence.

In an additional embodiment of the present invention there is a method to correct a G mutation at nucleotide 908 of an estrogen receptor alpha nucleic acid sequence in a cell of an individual, comprising the step of administering to the cell an estrogen receptor alpha nucleic acid sequence comprising an A at nucleotide 908. In a specific embodiment, the estrogen receptor alpha nucleic acid sequence comprising an A at nucleotide 908 is present on a vector. In another specific embodiment, the vector is selected from the group consisting of plasmid, viral vector, liposome, and a combination thereof. In an additional specific embodiment, the viral vector is selected from the group consisting of adenoviral vector, retroviral vector, adeno-associated viral vector, or a combination thereof.

In an additional embodiment of the present invention there is a method to prevent breast cancer in an individual, comprising the steps of obtaining a sample from a breast of the individual; identifying in the sample an A908G mutation in a nucleic acid sequence of estrogen receptor alpha; and correcting the A908G mutation, wherein the correction results in the prevention of the breast cancer. In a specific embodiment, the breast sample is from a premalignant lesion of the breast. In another specific embodiment, the correction step comprises administering an estrogen receptor alpha nucleic acid sequence comprising a G at nucleotide 908 to a cell comprising an estrogen receptor alpha nucleic acid sequence containing the A908G mutation.

In an additional embodiment of the present invention there is a method to treat breast cancer in an individual, wherein an estrogen receptor alpha nucleic acid sequence in a breast cell of the individual has an A908G mutation, comprising the step of administering to the cell an estrogen receptor alpha nucleic acid sequence comprising a G at nucleotide 908.

In another embodiment of the present invention there is a method to prevent breast cancer in an individual, comprising the steps of obtaining a sample from a breast of the individual; identifying in the sample an arginine at amino acid residue 303 in an amino acid sequence of estrogen receptor alpha; and administering to the individual an amino acid sequence of estrogen receptor alpha comprising a lysine at amino acid residue 303, wherein the administration results in the prevention of the breast cancer. In a specific embodiment, the breast sample is from a premalignant lesion of the breast.

In an object of the present invention there is a method of identifying a modulator of an estrogen receptor alpha K303R polypeptide, comprising providing a candidate modulator; admixing the candidate modulator with an isolated compound or cell, or a suitable experimental animal; measuring one or more characteristics of the compound, cell or animal; and comparing the characteristic measured with the characteristic of the compound, cell or animal in the absence of the candidate modulator, wherein a difference between the measured characteristics indicates that the candidate modulator is the modulator of the compound, cell or animal.

In another object of the present invention, there is a method of screening for a modulator of an estrogen receptor alpha polypeptide comprising a K303R substitution, comprising introducing to a cell a vector comprising a nucleic acid sequence which encodes the estrogen receptor alpha K303R polypeptide; a vector comprising at least one estrogen-responsive regulatory element operatively linked to a reporter polynucleotide; and a test agent; and assaying expression of the reporter polynucleotide in the presence of the test agent, wherein the test agent is the modulator when the reporter polynucleotide expression changes in the presence of the test agent. In a specific embodiment, at least one of the vectors is transiently transfected into the cell. In another specific embodiment, at least one of the vectors is stably transfected into the cell. In an additional embodiment, when expression of the reporter polynucleotide is upregulated, the modulator is an agonist. In an additional embodiment, when expression of the reporter polynucleotide is downregulated, the modulator is an antagonist. In a further specific embodiment, when the expression of the reporter polynucleotide is downregulated, the modulator is an antagonist. In a specific embodiment, the cell is a mammalian cell. In a further specific embodiment, the mammalian cell is selected from the group consisting of CHO, HepG2, HeLa, COS-1, MCF-7, MDA-MB-231, T47D, ZR-75, MDA-MB-435, BT-20, MDA-MB-468, and HEC-1. In an additional specific embodiment, the estrogen-responsive regulatory element is selected from the group consisting of SEQ ID NO:36, SEQ ID NO:37, SEQ ID NO:38, SEQ ID NO:39, SEQ ID NO:40, SEQ ID NO:41, SEQ ID NO:42; SEQ ID NO:43, SEQ ID NO:44, SEQ ID NO:45, SEQ ID NO:46, SEQ ID NO:47, SEQ ID NO:48, SEQ ID NO:49; SEQ ID NO:22; SEQ ID NO:26, and SEQ ID NO:8. In an additional specific embodiment, the reporter polynucleotide is luciferase, chloramphenicol acetyltransferase, renilla or β-galactosidase. In a specific embodiment, there is a method of treating breast cancer in an individual comprising the step of administering the antagonist to the individual.

In another object of the present invention, there is a method of identifying a polypeptide which interacts with an estrogen receptor alpha polypeptide comprising a K303R substitution, comprising introducing to a cell, a vector comprising a polynucleotide which encodes a chimeric polypeptide comprising the estrogen receptor alpha K303R polypeptide and a DNA binding domain; introducing to the cell, a vector comprising a polynucleotide which encodes a chimeric polypeptide comprising a candidate polypeptide and a DNA activation domain; and assaying for an interaction between the DNA binding domain and the DNA activation domain, wherein when the interaction occurs, the candidate polypeptide is the polypeptide which interacts with the estrogen receptor alpha K303R polypeptide. In a specific embodiment, the polypeptide which interacts with the estrogen receptor alpha K303R polypeptide is an antagonist of the estrogen receptor alpha K303R polypeptide. In a specific embodiment, the interaction is assayed by assaying for a change in expression of a reporter sequence. In a specific embodiment, the cell is a yeast cell. In another specific embodiment, the cell is a mammalian cell. In a further specific embodiment, the DNA activation domain and the DNA binding domain are from GAL4 or LexA. In an additional specific embodiment, the reporter sequence is selected from the group consisting of β-galactosidase, luciferase, chloramphenicol acetyltransferase, and renilla. In a specific embodiment, there is a method of treating an individual for breast cancer, comprising administering the antagonist to the individual.

In another object of the present invention, there is a method of identifying a peptide which interacts with an estrogen receptor alpha K303R polypeptide, comprising obtaining an estrogen receptor alpha K303R polypeptide having an affinity tag and a label; introducing the polypeptide to a substrate comprising a plurality of bacteriophage, wherein the bacteriophage produce a candidate peptide; and determining binding of the polypeptide with the candidate peptide, wherein when the polypeptide binds the candidate peptide, the candidate peptide is the interacting peptide. In a specific embodiment, the label is a color label, a fluorescence label, or a radioactive label. In another specific embodiment, the affinity tag is biotin, GST, histidine, myc, or calmodulin-binding protein.

In an additional object of the present invention, there is a method of identifying a compound for the treatment of breast cancer associated with an estrogen receptor alpha K303R polypeptide, comprising the steps of obtaining a compound suspected of having the activity; and determining whether the compound has the activity. In a specific embodiment, the compound having the activity is an antagonist of the estrogen receptor alpha K303R polypeptide. In a specific embodiment, the method further comprises dispersing the compound in a pharmaceutical carrier; and administering a therapeutically effective amount of the compound in the carrier to an individual having the breast cancer.

Another object of the present invention is the compound obtained by the method of identifying a compound for the treatment of breast cancer associated with an estrogen receptor alpha K303R polypeptide, comprising the steps of obtaining a compound suspected of having the activity; and determining whether the compound has the activity.

An additional object of the present invention is a pharmacologically acceptable composition comprising the compound obtained by the method of identifying a compound for the treatment of breast cancer associated with an estrogen receptor alpha K303R polypeptide, comprising the steps of obtaining a compound suspected of having the activity; and determining whether the compound has the activity; and a pharmaceutical carrier.

Other and further objects, features, and advantages would be apparent and eventually more readily understood by reading the following specification and be reference to the accompanying drawings forming a part thereof, or any examples of the presently preferred embodiments of the invention given for the purpose of the disclosure.

DETAILED DESCRIPTION OF THE INVENTION

Figure 1:
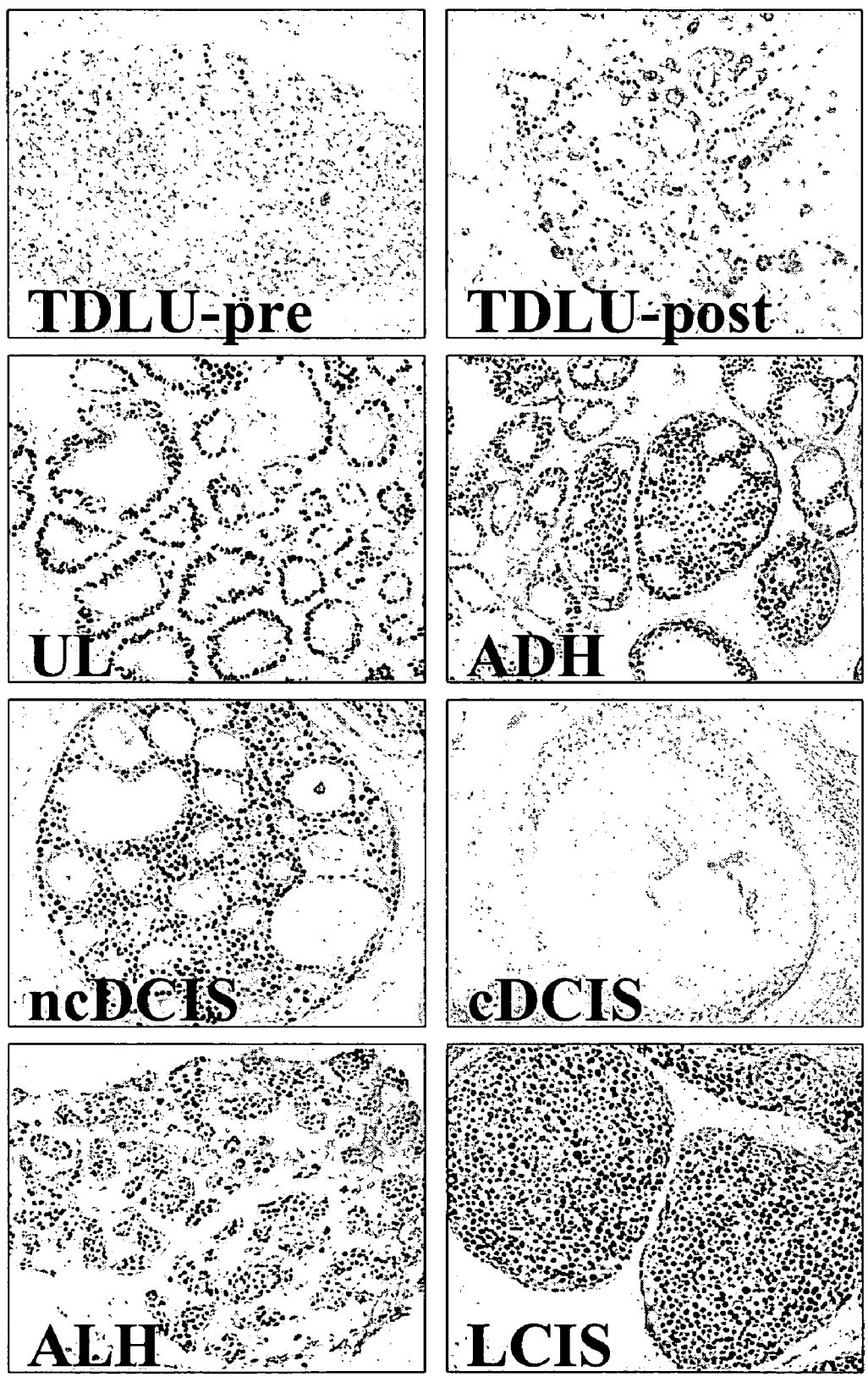
FIG. 1 illustrates examples of typical estrogen receptor (ER) expression in premalignant breast lesions as assayed by immunohistochemistry (small dark nuclei are ER-positive cells).

It will be readily apparent to one skilled in the art that various embodiments and modifications may be made in the invention disclosed herein without departing from the scope and spirit of the invention.

As used in the specification, "a" or "an" may mean one or more. As used in the claim(s), when used in conjunction with the word "comprising", the words "a" or "an" may mean one or more than one. As used herein "another" may mean at least a second or more.

I. Definitions

The term "A908G mutation" as used herein is defined as an adenine (A)-to-guanine (G) base pair transition at nucleotide position 908 in an estrogen receptor alpha nucleic acid sequence, relative to the first nucleotide of the first codon of the translated amino acid sequence. A skilled artisan recognizes that multiple estrogen receptor alpha nucleic acid sequences exist which are, for example, alternative splice variants. Thus, there are some estrogen receptor alpha nucleic acid sequences of different sizes, and the A908G mutation which is present at nucleotide (nt) 908 in the full-length mutated sequence may no longer be at position 908 in a variant sequence. However, a skilled artisan can readily identify the equivalent or analogous sequence in these variants by sequence homology and comparison, and/or by analyzing locations, arrangements or relationships of splicing manipulations. Thus, an estrogen receptor alpha nucleic acid sequence which contains the indicated mutation yet is a variant, such as an alternatively spliced form of the sequence, is still within the scope of the present invention.

The term "agonist" as used herein is defined as a compound or composition which promotes, facilitates, allows, induces, or otherwise assists, activates or increases the function of the estrogen receptor alpha K303R polypeptide.

The term "antagonist" as used herein is defined as a compound or composition which inhibits, stops, deters, impedes, delays, or otherwise prevents the activity and functioning of the estrogen receptor alpha K303R polypeptide.

The term "biopsy" as used herein is defined as removal of a tissue from a breast for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "breast cancer" as used herein is defined as cancer which originates in the breast. In a specific embodiment, the breast cancer spreads to other organs, such as lymph nodes. In a specific embodiment, the breast cancer is invasive and may be metastatic.

The term "cancer" as used herein is defined as a new growth of tissue comprising uncontrolled and progressive multiplication. In a specific embodiment, upon a natural course the cancer is fatal. In specific embodiments, the cancer is invasive, metastatic, and/or anaplastic (loss of differentiation and of orientation to one another and to their axial framework).

The term "invasive" as used herein refers to cells which have the ability to infiltrate surrounding tissue. In a specific embodiment, the infiltration results in destruction of the surrounding tissue. In another specific embodiment, the cells are cancer cells. In a preferred embodiment, the cells are breast cancer cells, and the cancer spreads out of a duct into surrounding breast epithelium. In a specific embodiment, "metastatic" breast cancer is within the scope of "invasive."

The term "K303R substitution" as used herein is defined as the amino acid substitution which results from the A908G mutation in estrogen receptor alpha nucleic acid sequence. The term "Lys303Arg substitution" is used herein interchangeably. A skilled artisan recognizes that multiple estrogen receptor alpha amino acid sequences exist which are, for example, alternative splice variants. Thus, there are some estrogen receptor alpha amino acid sequences of different sizes, and the K303R substitution which is present in the full-length mutated sequence may no longer be at position 303 in the variant sequence. However, a skilled artisan can readily identify the equivalent or analogous sequence in these variants by sequence homology and comparison, and/or by analyzing locations, arrangements or relationships of splicing manipulations. Thus, an estrogen receptor alpha amino acid sequence which contains the indicated mutation yet is a variant, such as an alternatively spliced form of the sequence, is still within the scope of the present invention.

The term "laser capture microdissection" as used herein is defined as the use of an infrared (IR) laser beam to remove a desired cell from a nondesired cell. In preferred embodiments, the desired cell is a cancer cell and the nondesired cell is a normal cell. In another preferred embodiment, the cancer cell is a breast cancer cell.

The term "manual manipulation" as used herein is defined as the selective removal of a desired cell or cells from a nondesired cell or cells by hand. In preferred embodiments, the desired cell is a cancer cell and the nondesired cell is a normal cell. In another preferred embodiment, the cancer cell is a breast cancer cell.

The term "metastatic" as used herein is defined as the transfer of cancer cells from one organ or part to another not directly connected with it. In a specific embodiment, breast cancer cells spread to another organ or body part, such as lymph nodes.

The term "premalignant lesion" as used herein is defined as a collection of cells in a breast with histopathological characteristics which suggest at least one of the cells has an increased risk of becoming breast cancer. A skilled artisan recognizes that the most important premalignant lesions recognized today include unfolded lobules (UL; other names: blunt duct adenosis, columnar alteration of lobules), usual ductal hyperplasia (UDH; other names: proliferative disease without atypia, epitheliosis, papillomatosis, benign proliferative disease), a typical ductal hyperplasia (ADH), a typical lobular hyperplasia (ALH), ductal carcinoma in situ (DCIS), and lobular carcinoma in situ (LCIS). Other lesions which may have premalignant potential include intraductal papillomas, sclerosisng adenosis, and fibroadenomas (especially a typical fibroadenomas). In a specific embodiment, the collection of cells is a lump, tumor, mass, bump, bulge, swelling, and the like. Other terms in the art which are interchangeable with "premalignant lesion" include premalignant hyperplasia, premalignant neoplasia, and the like.

The term "sample from a breast" as used herein is defined as a specimen from any part or tissue of a breast. A skilled artisan recognizes that the sample may be obtained by any method, such as biopsy. In a specific embodiment the sample is obtained by nipple aspirate (see, for example, Sauter et al. (1997)). In another specific embodiment, the sample is from hyperplastic or malignant breast epithelium. In a specific embodiment, the sample is from the epithelium. In another specific embodiment, the sample is from a premalignant lesion. A skilled artisan recognizes that within the scope of the present invention is the embodiment wherein a normal, or benign, sample, such as from an epithelium, is obtained for risk screening.

II. The Present Invention

The best current model of breast cancer evolution suggests that most cancers arise from certain premalignant lesions. The present invention is directed to a common (34%) somatic mutation in the estrogen receptor (ER) α gene in a series of 59 typical hyperplasias, a type of early premalignant breast lesion. The mutation, which affects the border of the hinge and hormone binding domains of ERα, showed increased sensitivity to estrogen as compared to wild-type ERα in stably transfected breast cancer cells, including markedly increased proliferation at subphysiologic levels of estrogen. The mutated ERα exhibits significantly enhanced binding to the TIF-2 (SRC-2) and SRC-3 co-activators and moderately enhanced binding to SRC-1 at low levels of hormone, which in a specific embodiment explains its increased estrogen responsiveness. In a preferred embodiment, this mutation promotes or accelerates the development of cancer from premalignant breast lesions. As such, it is a useful tool for the diagnosis of breast cancer and determination of susceptibility to the development of breast cancer, including determination of the propensity for invasiveness.

A skilled artisan recognizes the existence of a variety of inherited, or somatically acquired, variations in the DNA of the estrogen receptor alpha gene in cells in a breast sample, which, in the latter case, may differ in a mixture of normal and neoplastic cells. As demonstrated in the Examples herein, those cells having DNA that contain an A908G mutation in the estrogen receptor alpha nucleic acid sequence are or will become cancerous, and particularly will be a cell of a breast cancer which will become metastatic. The present invention is directed to methods and compositions related to detection of the A908G mutation.

In an embodiment of the present invention there is an isolated estrogen receptor alpha nucleic acid sequence comprising an A908G mutation.

In another embodiment of the present invention there is an isolated estrogen receptor alpha amino acid sequence comprising a K303R substitution.

In an additional embodiment of the present invention there is a method of detecting susceptibility to development of breast cancer in an individual, comprising the steps of obtaining a sample from a breast of the individual, wherein the sample comprises a cell having an estrogen receptor alpha nucleic acid sequence; and assaying the nucleic acid sequence for an A908G mutation, wherein the presence of the mutation in the nucleic acid sequence indicates the individual has breast cancer. In a specific embodiment, the sample is from a premalignant lesion of the breast.

In an additional embodiment of the present invention there is a method of detecting susceptibility to development of invasive breast cancer in an individual, comprising the steps of obtaining a sample from a breast of the individual; and assaying an estrogen receptor alpha nucleic acid sequence from a cell of the sample for an A908G mutation, wherein the presence of the mutation in the nucleic acid sequence detects susceptibility of the premalignant lesion to develop into the invasive breast cancer. In a specific embodiment, the sample is from a premalignant lesion of the breast.

In an additional embodiment of the present invention there is a method of detecting susceptibility to development of invasive breast cancer from a premalignant lesion in a breast, comprising the steps of obtaining a sample from the premalignant lesion; dissecting the sample to differentiate hyperplastic cells in the sample from nonhyperplastic cells; and assaying an estrogen receptor alpha nucleic acid sequence from the hyperplastic cell of the sample for an A908G mutation, wherein the presence of the mutation in the nucleic acid sequence detects susceptibility of the premalignant lesion to develop into the invasive breast cancer. In a specific embodiment, the dissection step comprises removal of the hyperplastic cells from the sample by manual manipulation or by laser capture microdissection. In another specific embodiment, the sample is obtained by biopsy. In a specific embodiment, the assaying step comprises sequencing, single stranded conformation polymorphism, mismatch oligonucleotide mutation detection, or a combination thereof. In an additional specific embodiment, the assaying step is by antibody detection with antibodies to the A908G mutation of the estrogen receptor alpha nucleic acid sequence or is by antibody detection with antibodies to an acetylated estrogen receptor alpha amino acid sequence. In a further specific embodiment, the assaying step is by detection of SNPs by methods well known in the art.

In an additional embodiment of the present invention there is a method of classifying breast cancer in an individual, comprising the steps of obtaining from the individual a sample from the breast, wherein the sample contains a cancer cell; and assaying an estrogen receptor alpha nucleic acid sequence from the cell of the sample for an A908G mutation, wherein the presence of the mutation identifies the breast cancer to be invasive breast cancer. In a specific embodiment, the sample is obtained by biopsy. In another specific embodiment, the assaying step is selected from the group consisting of sequencing, single stranded conformation polymorphism, mismatch oligonucleotide mutation detection, and a combination thereof.

A skilled artisan recognizes that there are a variety of methods to detect a mutation in a nucleic acid sequence in addition to these methods. Methods regarding allele-specific probes for analyzing particular nucleotide sequences are described by e.g., Saiki et al., Nature 324, 163-166 (1986); Dattagupta, EP 235,726 (U.S. Pat. No. 836,378 (Mar. 5, 1986); U.S. Pat. No. 943,006 (Dec. 29, 1986)); Saiki, WO 89/11548 (U.S. Pat. No. 197,000 (May 20, 1988); U.S. Pat. No. 347,495 (May 4, 1989)). Allele-specific probes are typically used in pairs. One member of the pair shows perfect complementarity to a wildtype allele and the other members to a variant allele. In idealized hybridization conditions to a homozygous target, such a pair shows an essentially binary response. That is, one member of the pair hybridizes and the other does not. An allele-specific primer hybridizes to a site on target DNA overlapping the particular site in question and primes amplification of an allelic form to which the primer exhibits perfect complementarily (Gibbs, 1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch impairs amplification and little, if any, amplification product is generated.

Particular nucleic acid sites can also be identified by hybridization to oligonucleotide arrays. An example is described in WO 95/11995, which includes arrays having four probe sets. A first probe set includes overlapping probes spanning a region of interest in a reference sequence. Each probe in the first probe set has an interrogation position that corresponds to a nucleotide in the reference sequence. That is, the interrogation position is aligned with the corresponding nucleotide in the reference sequence when the probe and reference sequence are aligned to maximize complementarily between the two. For each probe in the first set, there are three corresponding probes from three additional probe sets. Thus, there are four probes corresponding to each nucleotide in the reference sequence. The probes from the three additional probe sets are identical to the corresponding probe from the first probe set except at the interrogation position, which occurs in the same position in each of the four corresponding probes from the four probe sets, and is occupied by a different nucleotide in the four probe sets. Such an array is hybridized to a labeled target sequence, which may be the same as the reference sequence, or a variant thereof. The identity of any nucleotide of interest in the target sequence can be determined by comparing the hybridization intensities of the four probes having interrogation positions aligned with that nucleotide. The nucleotide in the target sequence is the complement of the nucleotide occupying the interrogation position of the probe with the highest hybridization intensity.

WO 95/11995 also describes subarrays that are optimized for detection of variant forms of a precharacterized nucleotide site. A subarray contains probes designed to be complementary to a second reference sequence, which can be an allelic variant of the first reference sequence. The second group of probes is designed by the same principles as above except that the probes exhibit complementarity to the second reference sequence. The inclusion of a second group can be particularly useful for analyzing short subsequences of the primary reference sequence in which multiple mutations are expected to occur within a short distance commensurate with the length of the probes (i.e., two or more mutations within 9 to 21 bases).

An additional strategy for detecting a particular nucleotide site uses an array of probes is described in EP 717,113 (U.S. Pat. No. 327,525 (Oct. 21, 1994). In this strategy, an array contains overlapping probes spanning a region of interest in a reference sequence. The array is hybridized to a labeled target sequence, which may be the same as the reference sequence or a variant thereof. If the target sequence is a variant of the reference sequence, probes overlapping the site of variation show reduced hybridization intensity relative to other probes in the array. In arrays in which the probes are arranged in an ordered fashion stepping through the reference sequence (e.g., each successive probe has one fewer 5' base and one more 3' base than its predecessor), the loss of hybridization intensity is manifested as a "footprint" of probes approximately centered about the point of variation between the target sequence and reference sequence.

Mundy, C. R. (U.S. Pat. No. 4,656,127), for example, discusses a method for determining the identity of the nucleotide present at a particular site that employs a specialized exonuclease-resistant nucleotide derivative. A primer complementary to the allelic sequence immediately 3' to the site is permitted to hybridize to a target molecule obtained from a particular animal or human. If the site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the site of the target molecule was complementary to that of the nucleotide derivative used in the reaction. The Mundy method has the advantage that it does not require the determination of large amounts of extraneous sequence data. It has the disadvantages of destroying the amplified target sequences, and unmodified primer and of being extremely sensitive to the rate of polymerase incorporation of the specific exonuclease-resistant nucleotide being used.

Cohen, D. et al. (French Patent 2,650,840 (U.S. Pat. No. 4,420,902 (Dec. 20, 1983)); PCT Appln. No. WO91/02087) discuss a solution-based method for determining the identity of the nucleotide of a particular site. As in the Mundy method of U.S. Pat. No. 4,656,127, a primer is employed that is complementary to allelic sequences immediately 3' to the site. The method determines the identity of the nucleotide of that site using labeled dideoxynucleotide derivatives, which, if complementary to the nucleotide of the site will become incorporated onto the terminus of the primer.

An alternative method, known as Genetic Bit Analysis or GBA™ is described by Goelet, P. et al. (PCT Appln. No. 92/15712 (U.S. Pat. No. 664,837 (Mar. 5, 1991); U.S. Pat. No. 775,786 (Oct. 11, 1991)). The method of Goelet, P. et al. uses mixtures of labeled terminators and a primer that is complementary to the sequence 3' to a site in question. The labeled terminator that is incorporated is thus determined by, and complementary to, the nucleotide present in the site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase. It is thus easier to perform, and more accurate than the method discussed by Cohen.

An alternative approach, the "Oligonucleotide Ligation Assay" ("OLA") (Landegren, U. et al., Science 241:1077-1080 (1988)) has also been described as capable of detecting a nucleotide sequence variation. The OLA protocol uses two oligonucleotides which are designed to be capable of hybridizing to abutting sequences of a single strand of a target. One of the oligonucleotides is biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923-8927 (1990). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Recently, several primer-guided nucleotide incorporation procedures for assaying particular sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)).

In an additional specific embodiment of the present invention an assaying step is by antibody detection with antibodies to the A908G mutation of the estrogen receptor alpha nucleic acid sequence or by antibody detection with antibodies to an acetylated estrogen receptor alpha amino acid sequence.

In another embodiment of the present invention there is a method of diagnosing breast cancer in an individual, comprising the steps of obtaining a sample from a breast of the individual, wherein the sample comprises a cell having an estrogen receptor alpha nucleic acid sequence; and assaying the nucleic acid sequence for an A908G mutation, wherein the presence of the mutation in the nucleic acid sequence indicates the individual has breast cancer.

In another embodiment of the present invention there is a method of diagnosing breast cancer in an individual, comprising the steps of obtaining a sample from a breast of the individual; dissecting the sample to differentiate a cell suspected of being cancerous from a noncancerous cell; and assaying the cell suspected of being cancerous for an A908G mutation in an estrogen receptor alpha nucleic acid sequence, wherein the presence of the mutation in the nucleic acid sequence indicates the individual has breast cancer. In a specific embodiment, the dissection step comprises removal of the cells suspected of being cancerous from the sample by manual manipulation or by laser capture microdissection. In a specific embodiment, the sample is obtained by biopsy. In another specific embodiment, the assaying step is selected from the group consisting of sequencing, single stranded conformation polymorphism, mismatch oligonucleotide mutation detection, and a combination thereof. In an additional specific embodiment, the assaying step is by antibody detection with antibodies to the A908G mutation of the estrogen receptor alpha nucleic acid sequence or is by antibody detection with antibodies to an acetylated estrogen receptor alpha amino acid sequence. In a specific embodiment, the mutation is detected by SNP analysis, using standard methods in the art. Some methods use extendable primers for incorporating radiolabeled nucleotides, which can then be detected by fluorescence or resonance. For example, PerkinElmer™ (Shelton, Conn.) has the AcycloPrime™ fluorescence polarization SNP detection system which utilizes terminator labeled nucleotides to facilitate detection of the SNP upon fluorescence polarization. Also, Applied Biosystems (Foster City, Calif.) has the ABI PRISM® turbo TaqMan® probes for genotyping by allelic detection which utilizes fluorescent dyes, such as VIC™, and TET and 6-FAM, for detection. In a specific embodiment, the thymidine residues of the probes are replaced with 5-propyne-2'-deoxyuridine, which increases the $T_m$ of these probes by approximately 1° C. per substitution and facilitates design of a shorter probe for greater accuracy.

In another embodiment of the present invention there is a kit for diagnosing an A908G mutation in an estrogen receptor alpha nucleic acid sequence, comprising at least one primer selected from the group consisting of SEQ ID NO:15, SEQ ID NO:16, SEQ ID NO:17, SEQ ID NO:18, SEQ ID NO:33, SEQ ID NO:34, and SEQ ID NO:35. In a specific embodiment, the kit contains primers which are extendable. In an alternative specific embodiment, the kit contains primers which are nonextendable.

In another embodiment of the present invention there is a monoclonal antibody that binds immunologically to an acetylated estrogen receptor alpha amino acid sequence, or an antigenic fragment thereof In another embodiment of the present invention there is a monoclonal antibody that binds immunologically to an A908G mutation in an estrogen receptor alpha nucleic acid sequence.

In an additional embodiment of the present invention there is a method to correct a G mutation at nucleotide 908 of an estrogen receptor alpha nucleic acid sequence in a cell of an individual, comprising the step of administering to the cell an estrogen receptor alpha nucleic acid sequence comprising an A at nucleotide 908. In a specific embodiment, the estrogen receptor alpha nucleic acid sequence comprising an A at nucleotide 908 is present on a vector. In another specific embodiment, the vector is selected from the group consisting of plasmid, viral vector, liposome, and a combination thereof. In an additional specific embodiment, the viral vector is selected from the group consisting of adenoviral vector, retroviral vector, adeno-associated viral vector, or a combination thereof.

In an additional embodiment of the present invention there is a method to prevent breast cancer in an individual, comprising the steps of obtaining a sample from a breast of the individual; identifying in the sample an A908G mutation in a nucleic acid sequence of estrogen receptor alpha; and correcting the A908G mutation, wherein the correction results in the prevention of the breast cancer. In a specific embodiment, the breast sample is from a premalignant lesion of the breast. In another specific embodiment, the correction step comprises administering an estrogen receptor alpha nucleic acid sequence comprising a G at nucleotide 908 to a cell comprising an estrogen receptor alpha nucleic acid sequence containing the A908G mutation.

In an additional embodiment of the present invention there is a method to treat breast cancer in an individual, wherein an estrogen receptor alpha nucleic acid sequence in a breast cell of the individual has an A908G mutation, comprising the step of administering to the cell an estrogen receptor alpha nucleic acid sequence comprising a G at nucleotide 908.

In another embodiment of the present invention there is a method to prevent breast cancer in an individual, comprising the steps of obtaining a sample from a breast of the individual; identifying in the sample an arginine at amino acid residue 303 in an amino acid sequence of estrogen receptor alpha; and administering to the individual an amino acid sequence of estrogen receptor alpha comprising a lysine at amino acid residue 303, wherein the administration results in the prevention of the breast cancer. In a specific embodiment, the breast sample is from a premalignant lesion of the breast.

In an object of the present invention there is a method of identifying a modulator of an estrogen receptor alpha K303R polypeptide, comprising providing a candidate modulator; admixing the candidate modulator with an isolated compound or cell, or a suitable experimental animal; measuring one or more characteristics of the compound, cell or animal; and comparing the characteristic measured with the characteristic of the compound, cell or animal in the absence of the candidate modulator, wherein a difference between the measured characteristics indicates that the candidate modulator is the modulator of the compound, cell or animal.

In another object of the present invention, there is a method of screening for a modulator of an estrogen receptor alpha polypeptide comprising a K303R substitution, comprising introducing to a cell a vector comprising a nucleic acid sequence which encodes the estrogen receptor alpha K303R polypeptide; a vector comprising at least one estrogen-responsive regulatory element operatively linked to a reporter polynucleotide; and a test agent; and assaying expression of the reporter polynucleotide in the presence of the test agent, wherein the test agent is the modulator when the reporter polynucleotide expression changes in the presence of the test agent. In a specific embodiment, at least one of the vectors is transiently transfected into the cell. In another specific embodiment, at least one of the vectors is stably transfected into the cell. In an additional embodiment, when expression of the reporter polynucleotide is upregulated, the modulator is an agonist. In an additional embodiment, when expression of the reporter polynucleotide is downregulated, the modulator is an antagonist. In a further specific embodiment, when the expression of the reporter polynucleotide is downregulated, the modulator is an antagonist. In a specific embodiment, the cell is a mammalian cell. In a further specific embodiment, the mammalian cell is selected from the group consisting of CHO, HepG2, HeLa, COS-1, MCF-7, MDA-MB-231, T47D, ZR-75, MDA-MB-435, BT-20, MDA-MB-468, and HEC-1. In an additional specific embodiment, the estrogen-responsive regulatory element is selected from the group consisting of SEQ ID NO:36, SEQ ID NO:37, SEQ ID NO:38, SEQ ID NO:39, SEQ ID NO:40, SEQ ID NO:41, SEQ ID NO:42; SEQ ID NO:43, SEQ ID NO:44, SEQ ID NO:45, SEQ ID NO:46, SEQ ID NO:47, SEQ ID NO:48, SEQ ID NO:49; SEQ ID NO:22; SEQ ID NO:26, and SEQ ID NO:8. In an additional specific embodiment, the reporter polynucleotide is luciferase, chloramphenicol acetyltransferase, renilla or β-galactosidase. In a specific embodiment, there is a method of treating breast cancer in an individual comprising the step of administering the antagonist to the individual.

In another object of the present invention, there is a method of identifying a polypeptide which interacts with an estrogen receptor alpha polypeptide comprising a K303R substitution, comprising introducing to a cell, a vector comprising a polynucleotide which encodes a chimeric polypeptide comprising the estrogen receptor alpha K303R polypeptide and a DNA binding domain; introducing to the cell, a vector comprising a polynucleotide which encodes a chimeric polypeptide comprising a candidate polypeptide and a DNA activation domain; and assaying for an interaction between the DNA binding domain and the DNA activation domain, wherein when the interaction occurs, the candidate polypeptide is the polypeptide which interacts with the estrogen receptor alpha K303R polypeptide. In a specific embodiment, the polypeptide which interacts with the estrogen receptor alpha K303R polypeptide is an antagonist of the estrogen receptor alpha K303R polypeptide. In a specific embodiment, the interaction is assayed by assaying for a change in expression of a reporter sequence. In a specific embodiment, the cell is a yeast cell. In another specific embodiment, the cell is a mammalian cell. In a further specific embodiment, the DNA activation domain and the DNA binding domain are from GAL4 or LexA. In an additional specific embodiment, the reporter sequence is selected from the group consisting of β-galactosidase, luciferase, chloramphenicol acetyltransferase, and renilla. In a specific embodiment, there is a method of treating an individual for breast cancer, comprising administering the antagonist to the individual.

In another object of the present invention, there is a method of identifying a peptide which interacts with an estrogen receptor alpha K303R polypeptide, comprising obtaining an estrogen receptor alpha K303R polypeptide having an affinity tag and a label; introducing the polypeptide to a substrate comprising a plurality of bacteriophage, wherein the bacteriophage produce a candidate peptide; and determining binding of the polypeptide with the candidate peptide, wherein when the polypeptide binds the candidate peptide, the candidate peptide is the interacting peptide. In a specific embodiment, the label is a color label, a fluorescence label, or a radioactive label. In another specific embodiment, the affinity tag is biotin, GST, histidine, myc, or calmodulin-binding protein.

In an additional object of the present invention, there is a method of identifying a compound for the treatment of breast cancer associated with an estrogen receptor alpha K303R polypeptide, comprising the steps of obtaining a compound suspected of having the activity; and determining whether the compound has the activity. In a specific embodiment, the compound having the activity is an antagonist of the estrogen receptor alpha K303R polypeptide. In a specific embodiment, the method further comprises dispersing the compound in a pharmaceutical carrier; and administering a therapeutically effective amount of the compound in the carrier to an individual having the breast cancer.

Another object of the present invention is the compound obtained by the method of identifying a compound for the treatment of breast cancer associated with an estrogen receptor alpha K303R polypeptide, comprising the steps of obtaining a compound suspected of having the activity; and determining whether the compound has the activity.

An additional object of the present invention is a pharmacologically acceptable composition comprising the compound obtained by the method of identifying a compound for the treatment of breast cancer associated with an estrogen receptor alpha K303R polypeptide, comprising the steps of obtaining a compound suspected of having the activity; and determining whether the compound has the activity; and a pharmaceutical carrier.

III. Estrogen Receptor Alpha

Estrogen, mediated through the estrogen receptor (ER), plays a major role in regulating the growth and differentiation of normal breast epithelium (Pike et al., 1993; Henderson et al., 1988). It stimulates cell proliferation and regulates the expression of other genes, including the progesterone receptor (PgR). PgR then mediates the mitogenic effect of progesterone, further stimulating proliferation (Pike et al., 1993; Henderson et al., 1988). Several studies have assessed ER expression in normal breast epithelium and premalignant lesions. Studies of normal terminal duct lobular units (TDLUs) reported that nearly all (over 90%) express ER, but in a minority (averaging about 30%) of cells for all ages combined (Schmitt, 1995; Mohsin et al., 2000; Allegra et al., 1979; Peterson et al., 1986; Ricketts et al., 1991). In premenopausal women, the average proportion of ER-positive cells in TDLUs is somewhat lower (about 20%), and varies with the menstrual cycle, being twice as high during the follicular as the luteal phase (Ricketts et al., 1991). Proliferation in TDLUs peaks during the luteal phase (Potten et al., 1988), suggesting that the normal mitogenic effect of estrogen may be partially delayed or indirect and mediated by downstream interactions such as that between progesterone and PgR. In postmenopausal women, the average proportion of ER-positive cells in TDLUs is relatively high (about 50%) and stable in the absence of hormone replacement therapy (Mohsin et al., 2000). Very little is know about ER expression in ULs, although one preliminary study reported that virtually all expressed the receptor in over 90% of cells (Mohsin et al., 2000). A few studies have evaluated ER in ADH and collectively agreed that nearly all lesions express very high levels in nearly all cells (Schmitt, 1995; Mohsin et al., 2000; Barnes and Masood, 1990). Many studies have evaluated ER in DCIS and, on average, about 75% of all cases expressed the receptor (Mohsin et al., 2000; Zafrani et al., 1994; Albonico et al., 1996; Berardo et al., 1996; Barnes and Masood, 1990; Helin et al., 1989; Giri et al., 1989; Chaudhuri et al., 1993; Poller et al., 1993; Pallis et al., 1992; Leal et al., 1995; Karayiannakis et al., 1996; Bose et al., 1996). Expression varied with histological differentiation, being highest in non-comedo (non-mammary ductal) lesions, where up to 100% showed expression in over 90% of cells, and lowest in comedo lesions, where only about 30% showed expression in a minority of cells. ER was not expressed in about 25% of DCIS and these were predominately high-grade comedo lesions. Over 90% of LCIS expressed high levels of ER in nearly all cells (Fisher et al., 1996; Rudas et al., 1997; Querzoli et al., 1998; Libby et al., 1998; Giri et al., 1989; Pallis et al., 1992; Paertschuk et al., 1990), which is similar in ALH in a specific embodiment.

Prolonged estrogen exposure is an important risk factor for developing IBC, perhaps by allowing random genetic alterations to accumulate in normal cells stimulated to proliferate (Henderson et al. 1988), which may also be true for cells in premalignant lesions. The very high levels of ER observed in nearly all premalignant lesions (FIG. 1) may contribute to their increased proliferation relative to normal cells by allowing them to respond more effectively to any level of estrogen, even the low concentrations seen in postmenopausal women (Mohsin et al., 2000). FIG. 1 illustrates examples of typical estrogen receptor expression in premalignant breast lesions as assessed by immunohistochemistry (small dark nuclei are ER-positive cells). Terminal duct lobular units (TDLUs) in premenopausal (pre) women usually contain relatively few ER positive cells. In contrast, the majority of cells in TDLUs of postmenopausal (post) express ER. Most premalignant breast lesions show very high levels of ER in nearly all cells, including unfolded lobules (Uls), a typical ductal hyperplasias (ADHs), low grade "non-comedo" ductal carcinoma in situ (ncDCIS), a typical lobular hyperplasias (ALHs), and lobular carcinoma in situ (LCIS). The only significant exception is high grade "comedo" DCIS (cDCIS), which often show low or no ER expression.

In addition to increased levels of expression, there may be other alterations of ER resulting in increased growth in premalignant lesions. For example, in one recent study (Mohsin et al., 2000), proliferation was measured in TDLUs and premalignant lesions from the same breasts in a large number of patients stratified by menopausal status. Proliferation rates in TDLUs were nearly 3-fold lower in postmenopausal compared to premenopausal women, consistent with the expected mitogenic effect of estrogen and progesterone in normal cells. In contrast, the difference in proliferation in premalignant lesions stratified by menopausal status was less than half that of normal cells, suggesting that the hormonal regulation of proliferation in these lesions, in a specific embodiment, is fundamentally abnormal. It is an object of the present invention to diagnose such an abnormality by identifying an A908G mutation in estrogen receptor alpha nucleic acid sequence or a K303R substitution in the amino acid sequence.

IV. Premalignant Lesions of the Breast

Premalignant lesions of the breast are very common, and they are being diagnosed more frequently due to increasing public awareness and screening mammography. They are currently defined by their histological features and their prognosis is imprecisely estimated based on indirect epidemiological evidence (Page and Dupont, 1993). While lesions within specific categories look alike histologically, there must be underlying biological differences causing a subset to progress to IBC. Studies identifying biological prognostic factors in premalignant disease are beginning to emerge (see discussions in Page and Jensen, 1994; Page, 1995; Page et al., 1998; Lakhani, 1999). The histopathological characteristics and anatomic markers associated with premalignant lesions are well known in the art (Cardiff et al., 1977; Bocker, 1997; Page and Dupont, 1990; Stoll, 1999; Lishman and Lakhani, 1999, each of which are incorporated by reference herein in their entirety).

For example, preliminary results from two recent studies suggest that increased levels of ER in normal breast epithelium (Kahn et al., 1998) and certain premalignant lesions (UL, ADH, DCIS) (Mohsin et al., 2000) may be associated with a slightly elevated (2-to-3-fold) risk of developing IBC, and assessing ER status may eventually be important in clinical management. Its most promising role may be in identifying patients with high-risk premalignant lesions who might benefit from hormonal therapy. In the recent NSABP P-1 chemoprevention clinical trial (Fisher et al., 1998), patients with a history of ADH receiving tamoxifen experienced a dramatic decrease (85%) in breast cancer incidence. Nearly all ADH express very high levels of ER, suggesting that highly ER positive premalignant lesions may be particularly susceptible to hormonal therapy. The success of this trial is proof-of-principle that targeting biological alterations in premalignant disease is a rational strategy for the chemoprevention of breast cancer.

Even though microscopic in size, all types of premalignant breast lesions are tumors which expand terminal duct lobular units (TDLUs) and proximal ducts to many times their normal size. Many studies, using a variety of techniques, have measured the magnitude of proliferation in TDLUs and premalignant lesions (Table 1).

TABLE 1

Growth (proliferation and apoptosis) in premalignant breast lesions.

|  | TDLU | UL | ADH | DCIS | ALH | LCIS |
|---|---|---|---|---|---|---|
| Average % Proliferation | 2% | 5% | 5% | 15% | "low" | 2% |
| Average % Apoptosis | 0.6% | "low" | .03 | 5% | "low" | "low" |

Abbreviations:
TDLUs = terminal duct lobular units.
ULs = unfolded lobules.
ADH = atypical ductal hyperplasia.
DCIS = ductal carcinoma in situ.
ALH = atypical lobular hyperplasia.
LCIS = lobular carcinoma in situ.

Proliferation in TDLUs averaged only about 2% overall (Meyer, 1977; Ferguson and Anderson, 1981; Joshi et al., 1986; Longacre and Bartow, 1986; Russo et al., 1987; Going et al., 1988; Potten et al., 1988; Kamel et al., 1989; Schmitt, 1995; Visscher et al., 1996; Mohsin et al., 2000). In premenopausal women the rate fluctuates with the menstrual cycle and is two-fold higher in the luteal than the follicular phase (Potten et al., 1988). The association between hormonal status and proliferation emphasizes the importance of estrogen and progesterone as mitogens for normal breast epithelium (Pike et al., 1993). Proliferation has not been evaluated in unfolded lobules (ULs) with the exception of one preliminary study reporting an average rate of about 5%, which is still 2-to-3-fold higher than in normal TDLUs (Mohsin et al., 2000). Studies of ADH also observed rates averaging about 5% (Mohsin et al., 2000; De Potter et al., 1987; Hoshi et al., 1995). Proliferation has been studied more extensively in DCIS than any other type of premalignant lesion (Mohsin et al., 2000; Meyer, 1986; Locker et al., 1990; Poller et al., 1994; Bobrow et al., 1994; Zafrani et al., 1994; Albonico et al., 1996; Berardo et al., 1996). Rates averaged about 5% in histologically low-grade "non-comedo" ductal carcinoma in situ (DCIS) compared to 20% in high-grade "comedo" lesions. The wide-spread practice of dichotomizing DCIS into non-comedo and comedo subtypes is misleading in the sense that, similar to invasive breast cancer (IBC), DCIS shows tremendous histological diversity along a continuum ranging from very well to very poorly differentiated, and grading systems have been developed which more accurately convey this diversity (Berardo et al., 1996). Proliferation is proportional to differentiation along this continuum, with rates averaging as low as 1% in the lowest grade to more than 70% in the highest grade lesions (Bobrow et al., 1994; Berardo et al., 1996). Proliferation has not been formally studied in ALH but is probably similar to LCIS where the reported average is about 2% (Fisher et al., 1996; Rudas et al., 1997; Querzoli et al., 1998; Libby et al., 1998).

The overall growth of premalignant breast lesions can be viewed simplistically as a balance between cell proliferation and cell death. On average, the cells in all types of premalignant lesions proliferate faster than normal cells in TDLUs, contributing to their positive growth imbalance. Much less is known about cell death in this setting (Table 1). One preliminary study reported significantly lower rates of apoptosis in atypical ductal hyperplasia (ADH) (0.3%) compared to TDLUs (0.6%) in the same breasts, suggesting that the growth of ADH may be the result of both increased proliferation and decreased cell death compared to normal cells (Prosser et al., 1997). However, a few studies have reported rates of apoptosis in DCIS that are much higher (up to 10-fold) than typically seen in normal cells (Prosser et al., 1997; Bodis et al., 1996; Ham et al., 1997), yet DCIS have a profound positive growth imbalance, suggesting that the relationship between cell proliferation and death may not always be accurately portrayed by the static methods used to measure these dynamic processes. Like proliferation, apoptosis seems to vary with histological differentiation in DCIS, being much lower in non-comedo (averaging 0.7%) than comedo (averaging 5.6%) lesions (Prosser et al., 1997). Disturbances of the equilibrium between cell proliferation and death probably result from alterations of several normal growth-regulating mechanisms, including those involving sex hormones, oncogenes, tumor suppressor genes, and many other genetic and epigenetic abnormalities.

V. Laser Capture Microdissection

Developments in gene sequencing and amplification techniques, among others, now allow scientists to extract DNA or RNA from tissue biopsies and cytological smears for pinpoint molecular analysis, such as a point mutation in a nucleic acid sequence. The efficacy of these sophisticated genetic testing methods, however, depends on the purity and precision of the cell populations being analyzed. Simply homogenizing the biopsy sample results in an impure combination of healthy and diseased tissue. Using mechanical tools to manually separate cells of interest from the histologic section is time-consuming and extremely labor-intensive. None of these methods offers the ease, precision and efficiency necessary for modem molecular diagnosis.

The process of laser capture microdissection (LCM) circumvents many problems in the art regarding accuracy, efficiency and purity. A laser beam focally activates a special transfer film which bonds specifically to cells identified and targeted by microscopy within the tissue section. The transfer film with the bonded cells is then lifted off the thin tissue section, leaving all unwanted cells behind (which would contaminate the molecular purity of subsequent analysis). The transparent transfer film is applied to the surface of the tissue section. Under the microscope, the diagnostic pathologist or researcher views the thin tissue section through the glass slide on which it is mounted and chooses microscopic clusters of cells to study. When the cells of choice are in the center of the field of view, the operator pushes a button which activates a near IR laser diode integral with the microscope optics. The pulsed laser beam activates a precise spot on the transfer film immediately above the cells of interest. At this precise location the film melts and fuses with the underlying cells of choice. When the film is removed, the chosen cell(s) are tightly held within the focally expanded polymer, while the rest of the tissue is left behind. This allows multiple homogeneous samples within the tissue section or cytological preparation to be targeted and pooled for extraction of molecules and analysis.

In a commercial system, such as with the instruments and methods of Arcturus (Mountain View, Calif.) (http://www-.arctur.com/), the film is permanently bonded to the underside of a transparent vial cap. A mechanical arm precisely positions the transfer surface onto the tissue. The microscope focuses the laser beam to discrete sizes (presently either 30 or 60 micron diameters), delivering precise pulsed doses to the targeted film. Targeted cells are transferred to the cap surface, and the cap is placed directly onto a vial for molecular processing. The size of the targeting pulses is selected by the operator. The cells adherent to the film retain their morphologic features, and the operator can verify that the correct cells have been procured.

Examples of LCM with Breast Tissue include those available at http://www.arctur.com/technology/lcm_examples/ex_breast.html.

Methods regarding the specific preparations and techniques associated with LCM are well known in the art and are provided at (http://www.arctur.com/technology/protocols.html), including: Paraffin-Embedded Tissue, Frozen Tissue, White Blood Cell Cytospin, De-Paraffinization of Tissue Sections, Hematoxylin and Eosin Staining, Immunohistochemical Staining (IHC), Intercalator Dye Staining (Fluorescence), Methyl Green Staining, Nuclear Fast Red Staining, and Toluidine Blue O Staining.

An example of Laser Capture Microdissection steps, particularly for use with Acturus instruments, includes the following:

1. Prepare. Follow routine protocols for preparing a tissue or smear on a standard microscope slide. Apply a Prep Strip™ to flatten the tissue and remove loose debris prior to LCM.

2. Place. Place a CapSure™ HS onto the tissue in the area of interest. The CapSure™ HS is custom designed to keep the transfer film out of contact with the tissue.

3. Capture. Pulse the low power infrared laser. The laser activates the transfer film which then expands down into contact with the tissue. The desired cell(s) adhere to the CapSure™ HS transfer film.

4. Microdissect. Lift the CapSure™ HS film carrier, with the desired cell(s) attached to the film surface. The surrounding tissue remains intact.

5. Extract. Snap the ExtracSure™ onto the CapSure™ HS. The ExtracSure™ is designed to accept low volumes of digestion buffer while sealing out any non-selected material from the captured cells. Pipette the extraction buffer directly into the digestion well of the ExtracSure™. Place a microcentrifuge tube on top.

6. Analyze. Invert the microcentrifuge tube. After centrifuging, the lysate will be at the bottom of the tube. The cell contents, DNA, RNA or protein, are ready for subsequent molecular analysis.

VI. Mismatch Oligonucleotide Mutation Detection

A skilled artisan recognizes that one method to identify a point mutation in a nucleic acid sequence is by mismatch oligonucleotide mutation detection, also referred to by other names such as oligonucleotide mismatch detection. In a specific embodiment, a nucleic acid sequence comprising the site to be assayed for the mutation is amplified from a sample, such as by polymerase chain reaction, and a mutation is detected with mutation-specific oligonucleotide probe hybridization of Southern or slot blots, or a combination thereof.

In a specific embodiment of the present invention, an A908G mutation in estrogen receptor alpha nucleic acid sequence is identified by methods and/or kits employing oligonucleotide mismatch detection.

VII. Single-Strand Comformation Polymorphism

Single-strand conformation polymorphism (SSCP) (Orita et al., 1989) facilitates detection of polymorphisms, such as single base pair transitions, through mobility shift analysis on a neutral polyacrylamide gel by methods well known in the art. In specific embodiments, the method is subsequent to polymerase chain reaction or restriction enzyme digestion, either of which is followed by denaturation for separation of the strands. The single stranded species are transferred onto a support such as a nylon membrane, and the mobility shift is detected by hybridization with a nick-translated DNA fragment or with RNA. In alternative embodiments, the single stranded product is itself labeled, such as with radioactivity, for identification. Samples manifesting migration shifts in SSCP gels in a specific embodiment are analyzed further by other well known methods, such as by DNA sequencing.

In a specific embodiment of the present invention, an A908G mutation in estrogen receptor alpha nucleic acid sequence is identified by methods and/or kits employing single-strand conformation polymorphism.

VIII. Site-Directed Mutagenesis

Structure-guided site-specific mutagenesis represents a powerful tool for the dissection and engineering of protein-ligand interactions (Wells, 1996, Braisted et al, 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

IX. Nucleic Acid Detection

In addition to their use in directing the expression of estrogen receptor alpha wildtype or mutant proteins, polypeptides and/or peptides, the nucleic acid sequences disclosed herein have a variety of other uses. For example, they have utility as probes or primers for embodiments involving nucleic acid hybridization.

A. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

B. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to estrogen receptor alpha wild-type or mutant are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al, 1990, each of which is incorporated herein by reference in their entirety.

A reverse transcriptase PCR™ amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). Davey et al., European Application No. 329 822 disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

C. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

D. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substititution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

E. Kits

All the essential materials and/or reagents required for detecting estrogen receptor alpha wildtype or mutant sequences in a sample may be assembled together in a kit. This generally will comprise a probe or primers designed to hybridize specifically to individual nucleic acids of interest in the practice of the present invention, including estrogen receptor alpha wildtype or mutant sequences. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

X. Estrogen Receptor α Nucleic Acids

In a preferred embodiment, an estrogen receptor alpha nucleic acid sequence of the present invention contains an A908G mutation.

In specific embodiments, examples of the estrogen receptor alpha nucleic acid sequences which may include the A908G mutation include NM_000125.1 (SEQ ID NO:1); AF242866 (SEQ ID NO:2); AF123496.1 (SEQ ID NO:3); AF120105 (SEQ ID NO:4); U47678.1 (SEQ ID NO:5); M12674.1 (SEQ ID NO:6); X03635.1 (SEQ ID NO:7); AF309825 (SEQ ID NO:19); AF061181 (SEQ ID NO:20); AF184588 (SEQ ID NO:21); AF181077 (SEQ ID NO:23); Z37167 (SEQ ID NO:24); AF173235 (SEQ ID NO:25); X90668 (SEQ ID NO:27); and AK025747 (SEQ ID NO:28).

In other specific embodiments, examples of the estrogen receptor alpha amino acid sequences which may include the K303R substitution include NP_000116.1 (SEQ ID NO:9); AAF65451.1 (SEQ ID NO:10); AAD23565.1 (SEQ ID NO:11); AAB00115.1 (SEQ ID NO:12); AAA52399.1 (SEQ ID NO:13); CAA27284.1 (SEQ ID NO:14); AAF00503.1 (SEQ ID NO:29); AAD53956.1 (SEQ ID NO:30); CAA85524.1 (SEQ ID NO:31); and BAB15231.1 (SEQ ID NO:32).

The term "estrogen receptor alpha wildtype or mutant sequence" as used herein refers respectively to the estrogen receptor alpha wildtype sequence or to a mutant sequence, wherein the mutant sequence comprises an A908G mutation.

A. Nucleic Acids and Uses Thereof

Certain aspects of the present invention concern at least one estrogen receptor alpha wildtype and/or mutant nucleic acid. In certain aspects, the at least one estrogen receptor alpha wildtype and/or mutant nucleic acid comprises a wildtype or mutant estrogen receptor alpha wildtype and/or mutant nucleic acid. In certain aspects, the estrogen receptor alpha wildtype and/or mutant nucleic acid comprises at least one transcribed nucleic acid. In particular aspects, the estrogen receptor alpha wildtype and/or mutant nucleic acid encodes at least one estrogen receptor alpha wildtype and/or mutant protein, polypeptide or peptide, or biologically functional equivalent thereof. In other aspects, the estrogen receptor alpha wildtype and/or mutant nucleic acid comprises at least one nucleic acid segment of SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, SEQ ID NO:28, or at least one biologically functional equivalent thereof.

The present invention also concerns the isolation or creation of at least one recombinant construct or at least one recombinant host cell through the application of recombinant nucleic acid technology known to those of skill in the art or as described herein. The recombinant construct or host cell may comprise at least one estrogen receptor alpha wildtype or mutant nucleic acid, and may express at least one estrogen receptor alpha wildtype or mutant protein, peptide or peptide, or at least one biologically functional equivalent thereof.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e. two or more alleles exist) at a genetic locus in the individuals of a population. As used herein "mutant" refers to a change in the sequence of a nucleic acid or its encoded protein, polypeptide or peptide that is the result of the hand of man.

A nucleic acid may be made by any technique known to one of ordinary skill in the art. Non-limiting examples of synthetic nucleic acid, particularly a synthetic oligonucleotide, include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. No. 5,705,629, each incorporated herein by reference. A non-limiting example of enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Thus, the present invention also encompasses at least one nucleic acid that is complementary to a estrogen receptor alpha wildtype or mutant nucleic acid. In particular embodiments the invention encompasses at least one nucleic acid or nucleic acid segment complementary to the sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28. Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence of formamide, tetramethylammonium chloride or other solvent(s) in the hybridization mixture. It is generally appreciated that conditions may be rendered more stringent, such as, for example, the addition of increasing amounts of formamide.

It is also understood that these ranges, compositions and conditions for hybridization are mentioned by way of non-limiting example only, and that the desired stringency for a particular hybridization reaction is often determined empirically by comparison to one or more positive or negative controls. Depending on the application envisioned it is preferred to employ varying conditions of hybridization to achieve varying degrees of selectivity of the nucleic acid(s) towards target sequence(s). In a non-limiting example, identification or isolation of related target nucleic acid(s) that do not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

One or more nucleic acid(s) may comprise, or be composed entirely of, at least one derivative or mimic of at least one nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refers to a molecule that may or may not structurally resemble a naturally occurring molecule, but functions similarly to the naturally occurring molecule. As used herein, a "moiety" generally refers to a smaller chemical or molecular component of a larger chemical or molecular structure, and is encompassed by the term "molecule."

As used herein a "nucleobase" refers to a naturally occurring heterocyclic base, such as A, T, G, C or U ("naturally occurring nucleobase(s)"), found in at least one naturally occurring nucleic acid (i.e. DNA and RNA), and their naturally or non-naturally occurring derivatives and mimics. Non-limiting examples of nucleobases include purines and pyrimidines, as well as derivatives and mimics thereof, which generally can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

Nucleobase, nucleoside and nucleotide mimics or derivatives are well known in the art, and have been described in exemplary references such as, for example, Scheit, Nucleotide Analogs (John Wiley, New York, 1980), incorporated herein by reference. "Purine" and "pyrimidine" nucleobases encompass naturally occurring purine and pyrimidine nucleobases and also derivatives and mimics thereof, including but not limited to, those purines and pyrimidines substituted by one or more of alkyl, caboxyalkyl, amino, hydroxyl, halogen (i.e. fluoro, chloro, bromo, or iodo), thiol, or alkylthiol wherein the alkyl group comprises of from about 1, about 2, about 3, about 4, about 5, to about 6 carbon atoms. Non-limiting examples of purines and pyrimidines include deazapurines, 2,6-diaminopurine, 5-fluorouracil, xanthine, hypoxanthine, 8-bromoguanine, 8-chloroguanine, bromothymine, 8-aminoguanine, 8-hydroxyguanine, 8-methylguanine, 8-thioguanine, azaguanines, 2-aminopurine, 5-ethylcytosine, 5-methylcyosine, 5-bromouracil, 5-ethyluracil, 5-iodouracil, 5-chlorouracil, 5-propyluracil, thiouracil, 2-methyladenine, methylthioadenine, N,N-diemethyladenine, azaadenines, 8-bromoadenine, 8-hydroxyadenine, 6-hydroxyaminopurine, 6-thiopurine, 4-(6-aminohexyl/cytosine), and the like.

As used herein, "nucleoside" refers to an individual chemical unit comprising a nucleobase covalently attached to a nucleobase linker moiety. A non-limiting example of a "nucleobase linker moiety" is a sugar comprising 5-carbon atoms (a "5-carbon sugar"), including but not limited to deoxyribose, ribose or arabinose, and derivatives or mimics of 5-carbon sugars. Non-limiting examples of derivatives or mimics of 5-carbon sugars include 2'-fluoro-2'-deoxyribose or carbocyclic sugars where a carbon is substituted for the oxygen atom in the sugar ring. By way of non-limiting example, nucleosides comprising purine (i.e. A and G) or 7-deazapurine nucleobases typically covalently attach the 9 position of the purine or 7-deazapurine to the 1'-position of a 5-carbon sugar. In another non-limiting example, nucleosides comprising pyrimidine nucleobases (i.e. C, T or U) typically covalently attach the 1 position of the pyrimidine to 1'-position of a 5-carbon sugar (Kornberg and Baker, DNA Replication, 2nd Ed. (Freeman, San Francisco, 1992). However, other types of covalent attachments of a nucleobase to a nucleobase linker moiety are known in the art, and non-limiting examples are described herein.

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety, and non-limiting examples are described herein.

A non-limiting example of a nucleic acid comprising such nucleoside or nucleotide derivatives and mimics is a "polyether nucleic acid", described in U.S. Pat. No. 5,908,845, incorporated herein by reference, wherein one or more nucleobases are linked to chiral carbon atoms in a polyether backbone. Another example of a nucleic acid comprising nucleoside or nucleotide derivatives or mimics is a "peptide nucleic acid", also known as a "PNA", "peptide-based nucleic acid mimics" or "PENAMs", described in U.S. Pat. Nos. 5,786,461, 5891,625, 5,773,571, 5,766,855, 5,736,336, 5,719,262, 5,714,331, 5,539,082, and WO 92/20702, each of which is incorporated herein by reference. A peptide nucleic acid generally comprises at least one nucleobase and at least one nucleobase linker moiety that is either not a 5-carbon sugar and/or at least one backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Peptide nucleic acids generally have enhanced sequence specificity, binding properties, and resistance to enzymatic degradation in comparison to molecules such as DNA and RNA (Egholm et al., Nature 1993, 365, 566; PCT/EP/01219). In addition, U.S. Pat. Nos. 5,766,855, 5,719,262, 5,714,331 and 5,736,336 describe PNAs comprising naturally and non-naturally occurring nucleobases and alkylamine side chains with further improvements in sequence specificity, solubility and binding affinity. These properties promote double or triple helix formation between a target nucleic acid and the PNA.

U.S. Pat. No. 5,641,625 describes that the binding of a PNA may to a target sequence has applications the creation of PNA probes to nucleotide sequences, modulating (i.e. enhancing or reducing) gene expression by binding of a PNA to an expressed nucleotide sequence, and cleavage of specific dsDNA molecules. In certain embodiments, nucleic acid analogues such as one or more peptide nucleic acids may be used to inhibit nucleic acid amplification, such as in PCR, to reduce false positives and discriminate between single base mutants, as described in U.S. Pat. Ser. No. 5,891,625.

U.S. Pat. No. 5,786,461 describes PNAs with amino acid side chains attached to the PNA backbone to enhance solubility. The neutrality of the PNA backbone may contribute to the thermal stability of PNA/DNA and PNA/RNA duplexes by reducing charge repulsion. The melting temperature of PNA containing duplexes, or temperature at which the strands of the duplex release into single stranded molecules, has been described as less dependent upon salt concentration.

One method for increasing amount of cellular uptake property of PNAs is to attach a lipophilic group. U.S. application Ser. No. 117,363, filed Sep. 3, 1993, describes several alkylamino functionalities and their use in the attachment of such pendant groups to oligonucleosides. U.S. application Ser. No. 07/943,516, filed Sep. 11, 1992, and its corresponding published PCT application WO 94/06815, describe other novel amine-containing compounds and their incorporation into oligonucleotides for, inter alia, the purposes of enhancing cellular uptake, increasing lipophilicity, causing greater cellular retention and increasing the distribution of the compound within the cell.

Additional non-limiting examples of nucleosides, nucleotides or nucleic acids comprising 5-carbon sugar and/or backbone moiety derivatives or mimics are well known in the art.

In certain aspect, the present invention concerns at least one nucleic acid that is an isolated nucleic acid. As used herein, the term "isolated nucleic acid" refers to at least one nucleic acid molecule that has been isolated free of, or is otherwise free of, the bulk of the total genomic and transcribed nucleic acids of one or more cells, particularly mammalian cells, and more particularly human cells. In certain embodiments, "isolated nucleic acid" refers to a nucleic acid that has been isolated free of, or is otherwise free of, bulk of cellular components and macromolecules such as lipids, proteins, small biological molecules, and the like. As different species may have a RNA or a DNA containing genome, the term "isolated nucleic acid" encompasses both the terms "isolated DNA" and "isolated RNA". Thus, the isolated nucleic acid may comprise a RNA or DNA molecule isolated from, or otherwise free of, the bulk of total RNA, DNA or other nucleic acids of a particular species. As used herein, an isolated nucleic acid isolated from a particular species is referred to as a "species specific nucleic acid." When designating a nucleic acid isolated from a particular species, such as human, such a type of nucleic acid may be identified by the name of the species. For example, a nucleic acid isolated from one or more humans would be an "isolated human nucleic acid", a nucleic acid isolated from human would be an "isolated human nucleic acid", and so forth.

Of course, more than one copy of an isolated nucleic acid may be isolated from biological material, or produced in vitro, using standard techniques that are known to those of skill in the art. In particular embodiments, the isolated nucleic acid is capable of expressing a protein, polypeptide or peptide that has the K303R substitution. In other embodiments, the isolated nucleic acid comprises an isolated estrogen receptor alpha wildtype or mutant nucleic acid sequence.

Herein certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises an estrogen receptor alpha wildtype or mutant nucleic acid, and/or encodes an estrogen receptor alpha wildtype or mutant polypeptide or peptide coding sequences. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit.

As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

"Isolated substantially away from other coding sequences" means that the gene of interest, in this case the estrogen receptor alpha gene(s) containing the A908G mutation, forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

In certain embodiments, the nucleic acid is a nucleic acid segment. As used herein, the term "nucleic acid segment", are smaller fragments of a nucleic acid, such as for non-limiting example, those that encode only part of the estrogen receptor alpha wildtype or mutant peptide or polypeptide sequence. In a preferred embodiment, the mutant peptide or polypeptide sequence comprises the K303R substitution. Thus, a "nucleic acid segment" may comprise any part of the estrogen receptor alpha wildtype or mutant gene sequence(s), of from about 2 nucleotides to the full length of the estrogen receptor alpha wildtype or mutant peptide or polypeptide encoding region. In certain embodiments, the "nucleic acid segment" encompasses the full length estrogen receptor alpha wildtype or mutant gene(s) sequence. In particular embodiments, the nucleic acid comprises any part of the SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28 sequence(s), of from about 2 nucleotides to the full length of the sequence disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28.

A non-limiting example of the present invention would be the generation of nucleic acid segments of various lengths and sequence composition for probes and primers based on the sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The length overall length may vary considerably between nucleic acid constructs. Thus, a nucleic acid segment of almost any length may be employed, with the total length preferably being limited by the ease of preparation or use in the intended recombinant nucleic acid protocol.

In a non-limiting example, one or more nucleic acid constructs may be prepared that include a contiguous stretch of nucleotides identical to or complementary to SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28. A nucleic acid construct may be about 3, about 5, about 8, about 10 to about 14, or about 15, about 20, about 30, about 40, about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges", as used herein, means any length or range including or between the quoted values (i.e. all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 1,001, about 1002, etc,; about 50,001, about 50,002, etc; about 750,001, about 750,002, etc.; about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000,003, etc.

In particular embodiments, the invention concerns one or more recombinant vector(s) comprising nucleic acid sequences that encode an estrogen receptor alpha wildtype or mutant protein, polypeptide or peptide that includes within its amino acid sequence a contiguous amino acid sequence in accordance with, or essentially as set forth in SEQ ID NO:9, SEQ ID NO:10, SEQ ID NO:11, SEQ ID NO:12, SEQ ID NO:13, SEQ ID NO:14, SEQ ID NO:29, SEQ ID NO:30, SEQ ID NO:31, or SEQ ID NO:32 corresponding to human SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28. In other embodiments, the invention concerns recombinant vector(s) comprising nucleic acid sequences that encode a human estrogen receptor alpha wildtype or mutant protein, polypeptide or peptide that includes within its amino acid sequence a contiguous amino acid sequence in accordance with, or essentially as set forth in SEQ ID NO:9, SEQ ID NO:10, SEQ ID NO:11, SEQ ID NO:12, SEQ ID NO:13, SEQ ID NO:14, SEQ ID NO:29, SEQ ID NO:30, SEQ ID NO:31, or SEQ ID NO:32. In particular aspects, the recombinant vectors are DNA vectors.

The term "a sequence essentially as set forth in SEQ ID NO:9" means that the sequence substantially corresponds to a portion of SEQ ID NO:9 and has relatively few amino acids that are not identical to, or a biologically functional equivalent of, the amino acids of SEQ ID NO:9. Thus, "a sequence essentially as set forth in SEQ ID NO:1 encompasses nucleic acids, nucleic acid segments, and genes that comprise part or all of the nucleic acid sequences as set forth in SEQ ID NO:1.

The term "biologically functional equivalent" is well understood in the art and is further defined in detail herein. Accordingly, a sequence that has between about 70% and about 80%; or more preferably, between about 81% and about 90%; or even more preferably, between about 91% and about 99%; of amino acids that are identical or functionally equivalent to the amino acids of SEQ ID NO:9, SEQ ID NO:10, SEQ ID NO:11, SEQ ID NO:12, SEQ ID NO:13, SEQ ID NO:14, SEQ ID NO:29, SEQ ID NO:30, SEQ ID NO:31, or SEQ ID NO:32 will be a sequence that is "essentially as set forth in SEQ ID NO:9, SEQ ID NO:10, SEQ ID NO:11, SEQ ID NO:12, SEQ ID NO:13, SEQ ID NO:14, SEQ ID NO:29, SEQ ID NO:30, SEQ ID NO:31, or SEQ ID NO:32", provided the biological activity of the protein, polypeptide or peptide is maintained.

In certain other embodiments, the invention concerns at least one recombinant vector that include within its sequence a nucleic acid sequence essentially as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28. In particular embodiments, the recombinant vector comprises DNA sequences that encode protein(s), polypeptide(s) or peptide(s) exhibiting estrogen receptor alpha wildtype or mutant activity.

The term "functionally equivalent codon" is used herein to refer to codons that encode the same amino acid, such as the six codons for arginine and serine, and also refers to codons that encode biologically equivalent amino acids, which are well known in the art.

Information on codon usage in a variety of non-human organisms is known in the art (see for example, Bennetzen and Hall, 1982; Ikemura, 1981a, 1981b, 1982; Grantham et al., 1980, 1981; Wada et al., 1990; each of these references are incorporated herein by reference in their entirety). Thus, it is contemplated that codon usage may be optimized for other animals, as well as other organisms such as fungi, plants, prokaryotes, virus and the like, as well as organelles that contain nucleic acids, such as mitochondria, chloroplasts and the like, based on the preferred codon usage as would be known to those of ordinary skill in the art.

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28 will be nucleic acid sequences that are "essentially as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28".

It will also be understood that this invention is not limited to the particular nucleic acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:19, SEQ ID NO:20, SEQ ID NO:21, SEQ ID NO:23, SEQ ID NO:24, SEQ ID NO:25, SEQ ID NO:27, or SEQ ID NO:28, or the amino acid sequences of SEQ ID NO:9, SEQ ID NO:10, SEQ ID NO:11, SEQ ID NO:12, SEQ ID NO:13, SEQ ID NO:14, SEQ ID NO:29, SEQ ID NO:30, SEQ ID NO:31, or SEQ ID NO:32, respectively. Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have mutant amino acids sequences.

The nucleic acids of the present invention encompass biologically functional equivalent estrogen receptor alpha wildtype or mutant proteins, polypeptides, or peptides. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide, or to test mutants in order to examine estrogen receptor alpha wildtype or mutant protein, polypeptide or peptide activity at the molecular level.

Fusion proteins, polypeptides or peptides may be prepared, e.g., where the estrogen receptor alpha wildtype or mutant coding regions are aligned within the same expression unit with other proteins, polypeptides or peptides having desired functions. Non-limiting examples of such desired functions of expression sequences include purification or immunodetection purposes for the added expression sequences, e.g., proteinaceous compositions that may be purified by affinity chromatography or the enzyme labeling of coding regions, respectively.

Encompassed by the invention are nucleic acid sequences encoding relatively small peptides or fusion peptides, such as, for example, peptides of from about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, to about 100 amino acids in length, or more preferably, of from about 15 to about 30 amino acids in length; as set forth in SEQ ID NO:9, SEQ ID NO:10, SEQ ID NO:11, SEQ ID NO:12, SEQ ID NO:13, SEQ ID NO:14, SEQ ID NO:29, SEQ ID NO:30, SEQ ID NO:31, or SEQ ID NO:32, and also larger polypeptides up to and including proteins corresponding to the full-length sequences set forth in SEQ ID NO:9, SEQ ID NO:10, SEQ ID NO:11, SEQ ID NO:12, SEQ ID NO:13, SEQ ID NO:14, SEQ ID NO:29, SEQ ID NO:30, SEQ ID NO:31, or SEQ ID NO:32.

As used herein an "organism" may be a prokaryote, eukaryote, virus and the like. As used herein the term "sequence" encompasses both the terms "nucleic acid" and "proteinaceous" or "proteinaceous composition." As used herein, the term "proteinaceous composition" encompasses the terms "protein", "polypeptide" and "peptide." As used herein "artificial sequence" refers to a sequence of a nucleic acid not derived from sequence naturally occurring at a genetic locus, as well as the sequence of any proteins, polypeptides or peptides encoded by such a nucleic acid. A "synthetic sequence", refers to a nucleic acid or proteinaceous composition produced by chemical synthesis in vitro, rather than enzymatic production in vitro (i.e. an "enzymatically produced" sequence) or biological production in vivo (i.e. a "biologically produced" sequence).

XI. Protein Computer Modeling

To determine whether a mutation would likely produce a protein, polypeptide or peptide with a less exposed site and/or motif, the putative location of the altered, moved or added site and/or sequence could be determined by comparison of the mutated sequence to that of the unmutated protein, polypeptide or peptide's secondary and tertiary structure, as determined by such methods known to those of ordinary skill in the art including, but not limited to, X-ray crystallography, NMR or computer modeling. Computer models of various polypeptide and peptide structures are also available in the literature or computer databases. In a non-limiting example, the Entrez database (http://www.ncbi.nlm.nih.gov/Entrez/) may be used by one of ordinary skill in the art to identify target sequences and regions for mutagenesis. The Entrez database is crosslinked to a database of 3-D structures for the identified amino acid sequence, if known. Such molecular models may be used to identify sites and/or flanking sequences in peptides and polypeptides that are more exposed to contact with external molecules, (e.g. receptors) than similar sequences embedded in the interior of the polypeptide or polypeptide. In certain embodiments, when adding at least one site and/or flanking sequence is desirable, regions of the protein that are more exposed to contact with external molecules are preferred as sites to add such a sequence. The mutated or wildtype protein, polypeptide or peptide's structure could be determined by X-ray crystallography or NMR directly before use in in vitro or in vivo assays, as would be known to one of ordinary skill in the art.

XII. Prokaryotic Peptide Display

Molecular analysis of naturally occurring and artificial protein libraries has been greatly improved by the development of various "display" methodologies. The general scheme behind display techniques is the advantageous expression of peptides, and their disposition on some biological surface (phage, cell, etc.). The ability of different version of the displaying organism to present millions and millions of different variants allows the rapid screening of the corresponding library for biological function.

In U.S. Pat. No. 5,821,047, monovalent phage display is described. This method provides for the selection of novel proteins, and variants thereof. The method comprises fusing a gene encoding a protein of interest to the carboxy terminal domain of the gene III coat protein of the filamentous phage M13. The fusion is mutated to form a library of structurally related fusion proteins that are expressed in low quantity on the surface of phagemid candidates.

U.S. Pat. No. 5,571,698 describes directed evolution using an M13 phagemid system. A protein is expression as a fusion with the M13 gene III protein. Successive rounds of mutagenesis are performed, each time selecting for improved biological function, e.g., binding of a protein to a cognate binding partner.

Heterodimer phage libraries are described in U.S. Pat. No. 5,759,817. Filamentous phage comprising a matrix of cpVIII proteins encapsulating a genome encoding first and second polypeptides of an autogenously assembling receptor, such as an antibody, are provided. The receptor is surface-integrated into the phage coat matrix via the cpVIII membrane anchor, presenting the receptor for biological assessment.

Another system, lambdoid phage, also can be used for display purposes. In U.S. Pat. No. 5,672,024, lambdoid phage comprising a matrix of proteins encapsulating a genome encoding first and second polypeptides of an autogenously assembling receptor are prepared. The surface-integrated receptor is available on the surface on the phage for characterization.

Immunoglobulin heavy chain libraries are displayed by phage as described in U.S. Pat. No. 5,824,520. A single chain antibody library is generated by creating highly divergent, synthetic hypervariable regions, followed by phage display and selection. The resulting antibodies were used to inhibit intracellular enzyme activity. Another patent describing antibody display is U.S. Pat. No. 5,922,545.

Another example of phage display can be found in U.S. Pat. No. 5,780,279. This method provides for the identification and selection of novel substrates for enzymes. The method comprises constructing a gene fusion comprising DNA encoding a polypeptide fused to a DNA encoding a substrate peptide, which in turn is fusion to DNA encoding at least a portion of a phage coat protein. The DNA encoding the substrate peptide is mutated at one or more codons, thereby generating a family of mutants. The fusion protein is expressed on the surface of the phagemid particle and subjected to chemical or enzymatic modification of the substrate peptide. Those phagemid particles that have been modified are then separated from those that have not.

Bacteria also have been used successfully to display proteins. U.S. Pat. No. 5,348,867, describes expression of proteins on bacterial surfaces. The compositions and methods provide stable, surface-expressed polypeptide from recombinant gram-negative bacterial cell hosts. A tripartite chimeric gene and its related recombinant vector include separate DNA sequences for directing or targeting and translocating a desired gene product from a cell periplasm to the external cell surface. A wide range of polypeptides may be efficiently surface expressed using this system. See also, U.S. Pat. Nos. 5,508,192 and 5,866,344.

U.S. Pat. No. 5,500,353 describes another bacterial display system. Bacteria (e.g., *Caulobacter*) having a S-layer modified such that the bacterium S-layer protein gene contains one or more in-frame fusions coding for one or more heterologous peptides or polypeptides is described. The proteins are expressed on the surface of the bacterium, which may advantageously be cultured as a film.

XIII. Rational Drug Design

The goal of rational drug design is to produce structural analogs of biologically active compounds. By creating such analogs, it is possible to fashion drugs which are more active or stable than the natural molecules, which have different susceptibility to alteration or which may affect the function of various other molecules. In one approach, one would generate a three-dimensional structure for the antagonist of estrogen receptor alpha K303R polypeptide of the invention or a fragment thereof. This could be accomplished by X-ray crystallography, computer modeling or by a combination of both approaches. An alternative approach involves the random replacement of functional groups throughout the estrogen receptor alpha K303R polypeptide, and the resulting affect on function determined.

It also is possible to isolate a estrogen receptor alpha K303R polypeptide specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have enhanced and improved biological activity, for example, anti-breast cancer activity relative to a starting compound. By virtue of the chemical isolation procedures and descriptions well known in the art, sufficient amounts of the estrogen receptor alpha K303R polypeptide of the invention can be produced to perform crystallographic studies. In addition, knowledge of the chemical characteristics of these compounds permits computer employed predictions of structure-function relationships that facilitate drug design.

XIV. Screening for Modulators of the Protein Function

The present invention further comprises methods for identifying modulators of the function of an estrogen receptor alpha K303R polypeptide. These assays may comprise random screening of large libraries of candidate substances; alternatively, the assays may be used to focus on particular classes of compounds selected with an eye towards structural attributes that are believed to make them more likely to modulate the function of estrogen receptor alpha K303R polypeptide.

By fuction, it is meant that one may assay for antagonist and/or agonist activity of an estrogen receptor alpha K303R polypeptide.

To identify a estrogen receptor alpha K303R polypeptide modulator, one generally will determine the function of estrogen receptor alpha K303R polypeptide in the presence and absence of the candidate substance, a modulator defined as any substance that alters function. For example, a method generally comprises:

(a) providing a candidate modulator;
(b) admixing the candidate modulator with an isolated compound or cell, or a suitable experimental animal;
(c) measuring one or more characteristics of the compound, cell or animal in step (b); and
(d) comparing the characteristic measured in step (c) with the characteristic of the compound, cell or animal in the absence of said candidate modulator, wherein a difference between the measured characteristics indicates that said candidate modulator is, indeed, a modulator of the compound, cell or animal.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may potentially inhibit or enhance estrogen receptor alpha K303R polypeptide activity. The candidate substance may be a protein or fragment thereof, a small molecule, or even a nucleic acid molecule. It may prove to be the case that the most useful pharmacological compounds will be compounds that are structurally related to SERMs. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on an estrogen receptor alpha K303R polypeptide. Regardless of the type of inhibitor or activator identified by the present screening methods, the effect of the inhibition or activator by such a compound results in reduction in the activity of estrogen receptor alpha K303R polypeptide as a transcription factor as compared to that observed in the absence of the added candidate substance.

B. In vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

C. In Cyto Assays

The present invention also contemplates the screening of compounds for their ability to modulate estrogen receptor alpha K303R polypeptide in cells. Various cell lines can be utilized for such screening assays, including cells specifically engineered for this purpose. For example, cells comprising an estrogen receptor alpha K303R polypeptide-expressing vector, a vector comprising an estrogen regulatory element operatively linked to a reporter polynucleotide, and a compound to be screened are contemplated.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

D. In vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

The present invention provides methods of screening for a candidate substance that antagonizes an estrogen receptor alpha K303R polypeptide. In these embodiments, the present invention is directed to a method for determining the ability of a candidate substance to reduce the activity of estrogen receptor alpha K303R polypeptide, generally including the steps of: administering a candidate substance to the animal; and determining the ability of the candidate substance to reduce one or more characteristics of estrogen receptor alpha K303R polypeptide.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

XV. Mimetics

The present inventors contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins. Vita et al. (1998). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids. Weisshoff et al. (1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

XVI. Immunodetection Methods

In still further embodiments, the present invention concerns immunodetection methods for binding, purifying, removing, quantifying and/or otherwise generally detecting biological components such as estrogen receptor alpha protein or nucleic acid components. The estrogen receptor alpha antibodies prepared in accordance with the present invention may be employed to detect wild-type and/or mutant estrogen receptor alpha proteins, polypeptides and/or peptides. In specific embodiments, the antibodies detect an acetylated form of estrogen receptor alpha protein, polypeptide and/or peptide or the antibodies detect an A908G estrogen receptor alpha nucleic acid mutation. The use of wild-type and/or mutant estrogen receptor alpha specific antibodies is contemplated. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

In general, the immunobinding methods include obtaining a sample suspected of containing estrogen receptor alpha protein, polypeptide and/or peptide, and contacting the sample with a first anti-estrogen receptor alpha antibody in accordance with the present invention, as the case may be, under conditions effective to allow the formation of immunocomplexes.

These methods include methods for purifying wild-type and/or mutant estrogen receptor alpha proteins, polypeptides and/or peptides as may be employed in purifying wild-type and/or mutant estrogen receptor alpha proteins, polypeptides and/or peptides from patients' samples and/or for purifying recombinantly expressed wild-type or mutant estrogen receptor alpha proteins, polypeptides and/or peptides. In these instances, the antibody removes the antigenic wild-type and/or mutant estrogen receptor alpha protein, polypeptide and/or peptide component from a sample. The antibody will preferably be linked to a solid support, such as in the form of a column matrix, and the sample suspected of containing the wild-type or mutant estrogen receptor alpha protein antigenic component will be applied to the immobilized antibody. The unwanted components will be washed from the column, leaving the antigen immunocomplexed to the immobilized antibody, which wild-type or mutant estrogen receptor alpha protein antigen is then collected by removing the wild-type or mutant estrogen receptor alpha protein and/or peptide from the column.

The immunobinding methods also include methods for detecting and quantifying the amount of a wild-type or mutant estrogen receptor alpha protein reactive component in a sample and the detection and quantification of any immune complexes formed during the binding process. Here, one would obtain a sample suspected of containing a wild-type or mutant estrogen receptor alpha protein and/or peptide, and contact the sample with an antibody against wild-type or mutant estrogen receptor alpha, and then detect and quantify the amount of immune complexes formed under the specific conditions.

In terms of antigen detection, the biological sample analyzed may be any sample that is suspected of containing a wild-type or mutant estrogen receptor alpha protein-specific antigen, such as a breast tissue section or specimen, a homogenized breast tissue extract, a breast cell, separated and/or purified forms of any of the above wild-type or mutant estrogen receptor alpha protein-containing compositions, or even any biological fluid that comes into contact with the breast tissue. Diseases that may be suspected of containing a wild-type or mutant estrogen receptor alpha protein-specific antigen include, but are not limited to, breast cancer.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any estrogen receptor alpha protein antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The estrogen receptor alpha antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as various forms of cancer, such as breast cancer. Here, a biological and/or clinical sample suspected of containing a wild-type or mutant estrogen receptor alpha protein, polypeptide, peptide and/or mutant is used. However, these embodiments also have applications to non-clinical samples, such as in the titering of antigen or antibody samples, for example in the selection of hybridomas.

In the clinical diagnosis and/or monitoring of patients with various forms of breast cancer, the detection of estrogen receptor alpha mutant, and/or an alteration in the levels of estrogen receptor alpha, in comparison to the levels in a corresponding biological sample from a normal subject is indicative of a patient with cancer, such as breast cancer. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive.

A. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the anti-estrogen receptor alpha antibodies of the invention are immobilized onto a selected surface exhibiting protein affinity, such as a well in a polystyrene microtiter plate. Then, a test composition suspected of containing the wild-type and/or mutant estrogen receptor alpha protein antigen, such as a clinical sample, is added to the wells. After binding and/or washing to remove non-specifically bound immune complexes, the bound wild-type and/or mutant estrogen receptor alpha protein antigen may be detected. Detection is generally achieved by the addition of another anti-estrogen receptor alpha antibody that is linked to a detectable label. This type of ELISA is a simple "sandwich ELISA". Detection may also be achieved by the addition of a second anti-estrogen receptor alpha antibody, followed by the addition of a third antibody that has binding affinity for the second antibody, with the third antibody being linked to a detectable label.

In another exemplary ELISA, the samples suspected of containing the wild-type and/or mutant estrogen receptor alpha protein antigen are immobilized onto the well surface and/or then contacted with the anti-estrogen receptor alpha antibodies of the invention. After binding and/or washing to remove non-specifically bound immune complexes, the bound anti-estrogen receptor alpha antibodies are detected. Where the initial anti-estrogen receptor alpha antibodies are linked to a detectable label, the immune complexes may be detected directly. Again, the immune complexes may be detected using a second antibody that has binding affinity for the first anti-estrogen receptor alpha antibody, with the second antibody being linked to a detectable label.

Another ELISA in which the wild-type and/or mutant estrogen receptor alpha proteins, polypeptides and/or peptides are immobilized, involves the use of antibody competition in the detection. In this ELISA, labeled antibodies against wild-type or mutant estrogen receptor alpha protein are added to the wells, allowed to bind, and/or detected by means of their label. The amount of wild-type or mutant estrogen receptor alpha protein antigen in an unknown sample is then determined by mixing the sample with the labeled antibodies against wild-type and/or mutant estrogen receptor alpha before and/or during incubation with coated wells. The presence of wild-type and/or mutant estrogen receptor alpha protein in the sample acts to reduce the amount of antibody against wild-type or mutant estrogen receptor alpha protein available for binding to the well and thus reduces the ultimate signal. This is also appropriate for detecting antibodies against wild-type or mutant estrogen receptor alpha protein in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

C. Immunodetection Kits

In still further embodiments, the present invention concerns immunodetection kits for use with the immunodetection methods described above. As the estrogen receptor alpha antibodies are generally used to detect wild-type and/or mutant estrogen receptor alpha proteins, polypeptides and/or peptides, or to detect the A908G mutation in estrogen receptor nucleic acid sequence, the antibodies will preferably be included in the kit. However, kits including both such components may be provided. The immunodetection kits will thus comprise, in suitable container means, a first antibody that binds to a wild-type and/or mutant estrogen receptor alpha protein, polypeptide and/or peptide, and/or optionally, an immunodetection reagent and/or further optionally, a wild-type and/or mutant estrogen receptor alpha protein, polypeptide and/or peptide.

In preferred embodiments, monoclonal antibodies will be used. In certain embodiments, the first antibody that binds to the wild-type and/or mutant estrogen receptor alpha protein, polypeptide and/or peptide may be pre-bound to a solid support, such as a column matrix and/or well of a microtitre plate.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and/or all such labels may be employed in connection with the present invention.

The kits may further comprise a suitably aliquoted composition of the wild-type and/or mutant estrogen receptor alpha protein, polypeptide and/or polypeptide, whether labeled and/or unlabeled, as may be used to prepare a standard curve for a detection assay. The kits may contain antibody-label conjugates either in fully conjugated form, in the form of intermediates, and/or as separate moieties to be conjugated by the user of the kit. The components of the kits may be packaged either in aqueous media and/or in lyophilized form.

The container means of the kits will generally include at least one vial, test tube, flask, bottle, syringe and/or other container means, into which the antibody may be placed, and/or preferably, suitably aliquoted. Where wild-type and/or mutant estrogen receptor alpha protein, polypeptide and/or peptide, and/or a second and/or third binding ligand and/or additional component is provided, the kit will also generally contain a second, third and/or other additional container into which this ligand and/or component may be placed. The kits of the present invention will also typically include a means for containing the antibody, antigen, and/or any other reagent containers in close confinement for commercial sale. Such containers may include injection and/or blow-molded plastic containers into which the desired vials are retained.

XVII. Two Hybrid Screen

The term "two hybrid screen" as used herein refers to a screen to elucidate or characterize the function of a protein by identifying other proteins with which it interacts. The protein of unknown function, herein referred to as the "bait" is produced as a chimeric protein additionally containing the DNA binding domain of, for example, GAL4. Plasmids containing nucleotide sequences which express this chimeric protein are transformed into yeast cells, which also contain a representative plasmid from a library containing the respective GAL4 activation domain fused to different nucleotide sequences encoding different potential target proteins. If the bait protein physically interacts with a target protein, the GAL4 activation domain and GAL4 DNA binding domain are tethered and are thereby able to act conjunctively to promote transcription of a reporter gene. If no interaction occurs between the bait protein and the potential target protein in a particular cell, the GAL4 components remain separate and unable to promote reporter gene transcription on their own. One skilled in the art is aware that different reporter genes can be utilized, including β-galactosidase, HIS3, ADE2, or URA3. Furthermore, multiple reporter sequences, each under the control of a different inducible promoter, can be utilized within the same cell to indicate interaction of the GAL4 components (and thus a specific bait and target protein). A skilled artisan is aware that use of multiple reporter sequences decreases the chances of obtaining false positive candidates. Also, alternative DNA-binding domain/activation domain components may be used, such as LexA. One skilled in the art is aware that any activation domain may be paired with any DNA binding domain so long as they are able to generate transactivation of a reporter gene. Furthermore, a skilled artisan is aware that either of the two components may be of prokaryotic origin, as long as the other component is present and they jointly allow transactivation of the reporter gene, as with the LexA system.

Two hybrid experimental reagents and design are well known to those skilled in the art (see The Yeast Two-Hybrid System by P. L. Bartel and S. Fields (eds.) (Oxford University Press, 1997), including the most updated improvements of the system (Fashena et al., 2000). A skilled artisan is aware of commercially available vectors, such as the Matchmaker™ Systems from Clontech (Palo Alto, Calif.) or the HybriZAP® 2.1 Two Hybrid System (Stratagene; La Jolla, Calif.), or vectors available through the research community (Yang et al., 1995; James et al., 1996). In alternative embodiments, organisms other than yeast are used for two-hybrid analysis, such as mammals (Mammalian Two Hybrid Assay Kit from Stratagene (La Jolla, Calif.)) or E. coli (Hu et al., 2000).

In an alternative embodiment, a two-hybrid system is utilized wherein protein-protein interactions are detected in a cytoplasmic-based assay. In this embodiment, proteins are expressed in the cytoplasm, which allows posttranslational modifications to occur and permits transcriptional activators and inhibitors to be used as bait in the screen. An example of such a system is the CytoTrap® Two-Hybrid System from Stratagene™ (La Jolla, Calif.), in which a target protein becomes anchored to a cell membrane of a yeast which contains a temperature sensitive mutation in the cdc25 gene, the yeast homolog for hSos (a guanyl nucleotide exchange factor). Upon binding of a bait protein to the target, hSos is localized to the membrane, which allos activation of RAS by promoting GDP/GTP exchange. RAS then activates a signaling cascade which allows growth at 37° C. of a mutant yeast cdc25H. Vectors (such as pMyr and pSos) and other experimental details are available for this system to a skilled artisan through Stratagene (La Jolla, Calif.). (See also, for example, U.S. Pat. No. 5,776,689, herein incorporated by reference).

Thus, in accordance with an embodiment of the present invention, there is a method of screening for a peptide which interacts with ERα K303R polypeptide comprising introducing into a cell a first nucleic acid comprising a DNA segment encoding a test peptide, wherein the test peptide is fused to a DNA activation domain, and a second nucleic acid comprising a DNA segment encoding at least part of ERα K303R polypeptide, respectively, wherein the at least part of ERα K303R polypeptide, respectively, is fused to a DNA binding domain. Subsequently, there is an assay for interaction between the test peptide and the ERα K303R polypeptide or fragment thereof by assaying for interaction between the DNA activation domain and the DNA binding domain. In a preferred embodiment, the assay for interaction between the DNA binding and activation domains is activation of expression of β-galactosidase. In an alternative embodiment, the ERα K303R polypeptide is fused to the DNA activation domain and the test peptides are fused to the DNA binding domain.

XVIII. Cancer

Tumors are notoriously heterogeneous, particularly in advanced stages of tumor progression (Morton et al., 1993; Fidler and Hart, 1982; Nowell, 1982; Elder et al., 1989; Bystryn et al., 1985). Although tumor cells within a primary tumor or metastasis all may express the same marker gene, the level of specific mRNA expression can vary considerably (Elder et al., 1989). It is, in certain instances, necessary to employ a detection system that can cope with an array of heterogeneous markers. In a specific embodiment, a marker for breast cancer comprises an A908G estrogen receptor alpha nucleic acid sequence or the K303R substitution to which it corresponds, or both.

Thus, while the present invention exemplifies various tumor suppressors as a markers, any marker that is correlated with the presence or absence of cancer may be used in combination with these markers to improve the efficacy of tumor detection and treatment. A marker, as used herein, is any proteinaceous molecule (or corresponding gene) whose production or lack of production is characteristic of a cancer cell. Depending on the particular set of markers employed in a given analysis, the statistical analysis will vary. For example, where a particular combination of markers is highly specific for melanomas or breast cancer, the statistical significance of a positive result will be high. It may be, however, that such specificity is achieved at the cost of sensitivity, i.e., a negative result may occur even in the presence of melanoma or breast cancer. By the same token, a different combination may be very sensitive, i.e., few false negatives, but has a lower specificity.

As new markers are identified, different combinations may be developed that show optimal function with different ethnic groups or sex, different geographic distributions, different stages of disease, different degrees of specificity or different degrees of sensitivity. Marker combinations also may be developed, which are particularly sensitive to the effect of therapeutic regimens on disease progression. Patients may be monitored after surgery, gene therapy, hyperthermia, immunotherapy, cytokine therapy, gene therapy, radiotherapy or chemotherapy, to determine if a specific therapy is effective.

There are many other markers that may be used in combination with these, and other, markers. For example, β-human chorionic gonadotropin (β-HCG) is produced by trophoblastic cells of placenta of pregnant woman and is essential for maintenance of pregnancy at the early stages (Pierce et al., 1981; Talmadge et al., 1984). b-HCG is known to be produced by trophoblastic or germ cell origin tumors, such as choriocarcinoma or testicular carcinoma cells (Madersbacher et al., 1994; Cole et al., 1983). Also ectopic expression of b-HCG has been detected by a number of different immunoassays in various tumors of non-gonadal such as breast, lung, gastric, colon, and pancreas, etc. (McManus et al., 1976; Yoshimura et al., 1994; Yamaguchi et al., 1989; Marcillac et al., 1992; Alfthan et al., 1992). Although the function of b-HCG production in these tumors is still unknown, the atavistic expression of b-HCG by cancer cells and not by normal cells of non-gonadal origin suggests it may be a potentially good marker in the detection of melanoma and breast cancer (Hoon et al., 1996; Sarantou et al., 1997).

Another exemplary example of a marker is glycosyltransferase b-1, 4-N-acetylgalacto-saminyltransferase (GalNAc). GalNAc catalyzes the transfer of N-acetylgalactosamine by b1(r) 4 linkage onto both gangliosides GM3 and GD3 to generate GM2 and GD2, respectively (Nagata et al., 1992; Furukawa et al., 1993). It also catalyzes the transfer of N-acetylgalactosamine to other carbohydrate molecules such as mucins. Gangliosides are glycosphingolipids containing sialic acids which play an important role in cell differentiation, adhesion and malignant transformation. In melanoma, gangliosides GM2 and GD2 expression, are often enhanced to very high levels and associate with tumor progression including metastatic tumors (Hoon et al., 1989; Ando et al., 1987; Carubia et al., 1984; Tsuchida et al., 1987a), although gangliosides are also expressed in melanoma, renal, lung, breast carcinoma cancer cells. The gangliosides GM2 and GD2 are immunogenic in humans and can be used as a target for specific immunotherapy such as human monoclonal antibodies or cancer vaccines (Tsuchida et al., 1987b; Irie, 1985.)

Other markers contemplated by the present invention include cytolytic T lymphocyte (CTL) targets. MAGE-3 is a marker identified in melanoma cells and breast carcinoma. MAGE-3 is expressed in many melanomas as well as other tumors and is a (CTL) target (Gaugler et al., 1994). MAGE-1, MAGE-2, MAGE-4, MAGE-6, MAGE-12, MAGE-Xp, and are other members of the MAGE gene family. MAGE-1 gene sequence shows 73% identity with MAGE-3 and expresses an antigen also recognized by CTL (Gaugler et al., 1994). MART-1 is another potential CTL target (Robbins et al., 1994) and also may be included in the present invention.

Preferred embodiments of the invention involve many different combinations of markers for the detection of cancer cells. Any marker that is indicative of neoplasia in cells may be included in this invention. A preferred marker is an A908G estrogen receptor alpha nucleic acid sequence and/or a K303R substitution in an estrogen receptor alpha nucleic acid sequence.

XIX. Pharmaceutical Preparations

Pharmaceutical compositions of the present invention comprise an effective amount of one or more chimeric polypeptides or chimeric polypeptides and at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one composition or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

In some embodiments, an effective amount of a compositoin of the present invention, such as an antagonist to an estrogen receptor alpha K303R polypeptide, is administered to a cell. In other embodiments, a therapeutically effective amount of a composition of the present invention is administered to an individual for the treatment of disease. The term "effective amount" as used herein is defined as the amount of a composition of the present invention which is necessary to result in a physiological change in the cell or tissue to which it is administered. The term "therapeutically effective amount" as used herein is defined as the amount of a composition of the present invention that eliminates, decreases, delays, or minimizes adverse effects of a disease, such as cancer. A skilled artisan readily recognizes that in many cases the composition may not provide a cure but may only provide partial benefit. In some embodiments, a physiological change having some benefit is also considered therapeutically beneficial. Thus, in some embodiments, an amount of a composition that provides a physiological change is considered an "effective amount" or a "therapeutically effective amount."

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the chimeric polypeptide is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

XX. Methods of Making Transgenic Mice

A particular embodiment of the present invention provides transgenic animals that comprise constructs having the A908G mutation. In another embodiment, the transgenic animal comprises a polynucleotide encoding an estrogen receptor alpha amino acid sequence comprising K303R. Transgenic animals expressing these mutations, recombinant cell lines derived from such animals, and transgenic embryos may be useful in methods for screening for and identifying agents that interact with the estrogen receptor alpha, or affect breast tissue health.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual"

2nd edition (eds., Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 mg/ml in 5 mM Tris, pH 7.4 and 0.1 mM EDTA.

Other methods for purification of DNA for microinjection are described in Hogan et al. Manipulating the Mouse Embryo (Cold Spring Harbor Laboratory, Cold Spring Harbor, N.Y., 1986), in Palmiter et al. Nature 300:611 (1982); in The Qiagenologist, Application Protocols, 3rd edition, published by Qiagen, Inc., Chatsworth, Calif.; and in Sambrook et al. Molecular Cloning: A Laboratory Manual (Cold Spring Harbor Laboratory, Cold Spring Harbor, N.Y., 1989), all of which are incorporated by reference herein.

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by CO2 asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% C02, 95% air until the time of injection. Embryos can be implanted at the two-cell stage.

Randomly cycling adult female mice are paired with vasectomized males. FVB, C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

A skilled artisan is aware that transgenic mice are also commercially available, such as from Charles River Laboratories (Wilmington, Mass.).

EXAMPLES

The following examples are offered by way of example, and are not intended to limit the scope of the invention in any manner.

Example 1

Materials and Methods—Sample Preparation and Nucleotide Sequence Analysis

Histologic slides from archival, clinical specimens were screened microscopically for evidence of hyperplasia. Microdissection of specimens was performed on 55 samples using serial sections from formalin-fixed, paraffin-embedded tissue blocks as described (O'Connell et al., 1999). Briefly, alternative 3- and 10 um-thick sections were cut from the blocks and float mounted on glass slides. The 3-um-thick slides were stained with hematoxylin-eosin and examined under the light microscope to locate regions of normal and hyperplastic tissues; and these areas outlined with a felt-tipped pen. The marked slide was then used as a template to guide manual microdissection from the corresponding regions of the unstained 10-um-thick sections. It was possible to obtain distant normal tissue from 4 of the patients with hyperplasia. A skilled artisan recognizes that there are a variety of methods to isolate desired cells from nondesired cells other than by manual manipulation or LCM. These include physical means of separating out undesired cells from desired cells, such as by centrifugation based on size, or centrifugation with magnetic beads attached to antibodies specific for desired and nondesired cell types.

DNA was liberated from the microdisseced specimens using a modification of the procedure of O'Connell et al (1999). Genomic sequencing was then performed using PCR amplification of isolated DNA using ER primer 1 (nucleotides 1093-1112 (5' primer; 5'-CAAGCGCCAGAGAGAT-GATG-3'); SEQ ID NO:15) and ER primer 2 (nucleotides 1231-1250 (3' primer); 5'-ACAAGGCACTGACCATCTGG-3'; SEQ ID NO:16) of the ER gene (Greene et al., 1996). An aliquot of this amplification was then used to perform single stranded PCR amplification using ER primer 3 (nucleotides 1221-1240 (3' primer); 5'-GACCATCTGGTCGGCCGTCA-3'; SEQ ID NO:17) of the ER gene. After precipitation of the single stranded PCR amplification product, dideoxysequence analysis was performed using ER primer 4 (nucleotides 1099-1119 (5' primer); CAGAGAGAATGATGGGGAGGG-3'; SEQ ID NO:18). In another embodiment, an alternative ER primer is used in lieu of ER primer 4, such as for nucleotides 1101-1130 (SEQ ID NO:35). Genomic DNA was isolated from normal blood samples of 80 healthy women, and utilized for genomic sequence analysis as described above. RNA was also isolated from four additional, frozen hyperplastic lesions, and utilized for RT/PCR amplification, cloning, and sequence analyses as described (Fuqua et al., 1991).

Example 2

Materials and Methods—Stable Transfection and Cell Growth Analyses

The WT ER expression construct was prepared in the pcDNAI vector as described previously (Fuqua et al., 1995). Site directed mutagenesis of this construct was then utilized to generate the A908G transition and the entire coding sequence of ER was verified by dideoxysequence analysis in this clone. The generation of stable transfectants was performed as described by Oesterreich et al. (1993) using cotransfection with the G418-selectable expression vector pSVneo at a ration of 25:1 with the ER plasmids into MCF-7 breast cancer cells. To analyze for expression of both WT or Var sequences, Western blot analyses were performed using the 6F11 antibody (DaKO). Two to three-fold elevated levels of total ER protein were detected in the two WT ER and the three Var clones. In addition, RT/PCR amplification of cDNA from the transfectants (Fuqua et al., 1991) followed by dideoxysequence analysis confirmed that exogenous WT and Var RNA were expressed in the stable transfectants. Furthermore, the relative levels of WT or Var sequences were determined by genomic sequence analysis as described above; the ER Var transfectants contained both WT nucleotide (A) and Var nucleotide (G) sequence in approximately equal ratios on the sequencing gels. For cell growth studies, cells were plated at a density of $2 \times 10^4$ in media containing 10% charcoal-stripped, estrogen-free fetal calf serum and were either left untreated or treated with the indicated increasing estradiol concentrations of $1 \times 10^{-12}$, $1 \times 10^{-11}$, or $1 \times 10^{-9}$ M. The medium was replaced every 48 h and the cells were harvested and counted on days 2, 4, 6, and 8, respectively.

Example 3

Statistical Methods

After taking logarithms to stabilize within group variances, as determined to be appropriate by Box-Cox analysis (Box and Cox, 1996), one-way analysis of variance was used to detect estrogen dose-related differences in growth on Day 8 (i.e. 0 versus $10^{-12}$ M versus $10^{-11}$ M versus $10^{-9}$ M), and to detect differences among estrogen doses ($10^{-12}$ M versus $10^{-11}$ M versus $10^{-9}$ M). The Student-Newman-Keuls multiple range test ($\alpha=0.02$) was used to determine which doses were different from each other. Analyses were preformed using SAS (V6.12, SAS Institute, Cary, N.C.).

Example 4

Materials and Methods—GST Pull-Down Assays

Bacterial expression vectors for GST-wt ER and GST-mutant ER were constructed by PCR amplification of the hinge and hormone binding domains of wild-type ER α and the A908G ER α using a sense primer (nucleotides 756-775 and an antisense primer (nucleotides 1788-1769) (Greene et al., 1996), and then cloning these products into the BamH1-EcoRI sites of pGEX-2kt GST gene fusion vector (Pharmacia). The GST-pull down assays were performed as described (Ding et al., 1998) using recombinant SRC-2 (pSG5-human TIF-2) translated in vitro using the TNT coupled Reticulocyte Lysate System (Promega, Madison, Wis.), as well as recombinant SRC-1 and SRC-3. The reactions were allowed to bind the glutathione-Sepharose 4B beads (Pharmacia) for 1.5 h in the presence of increasing amounts of estradiol at 4° C. Samples were subsequently analyzed by SDS-polyacrylamide gel electrophoresis.

Example 5

Figure 2:
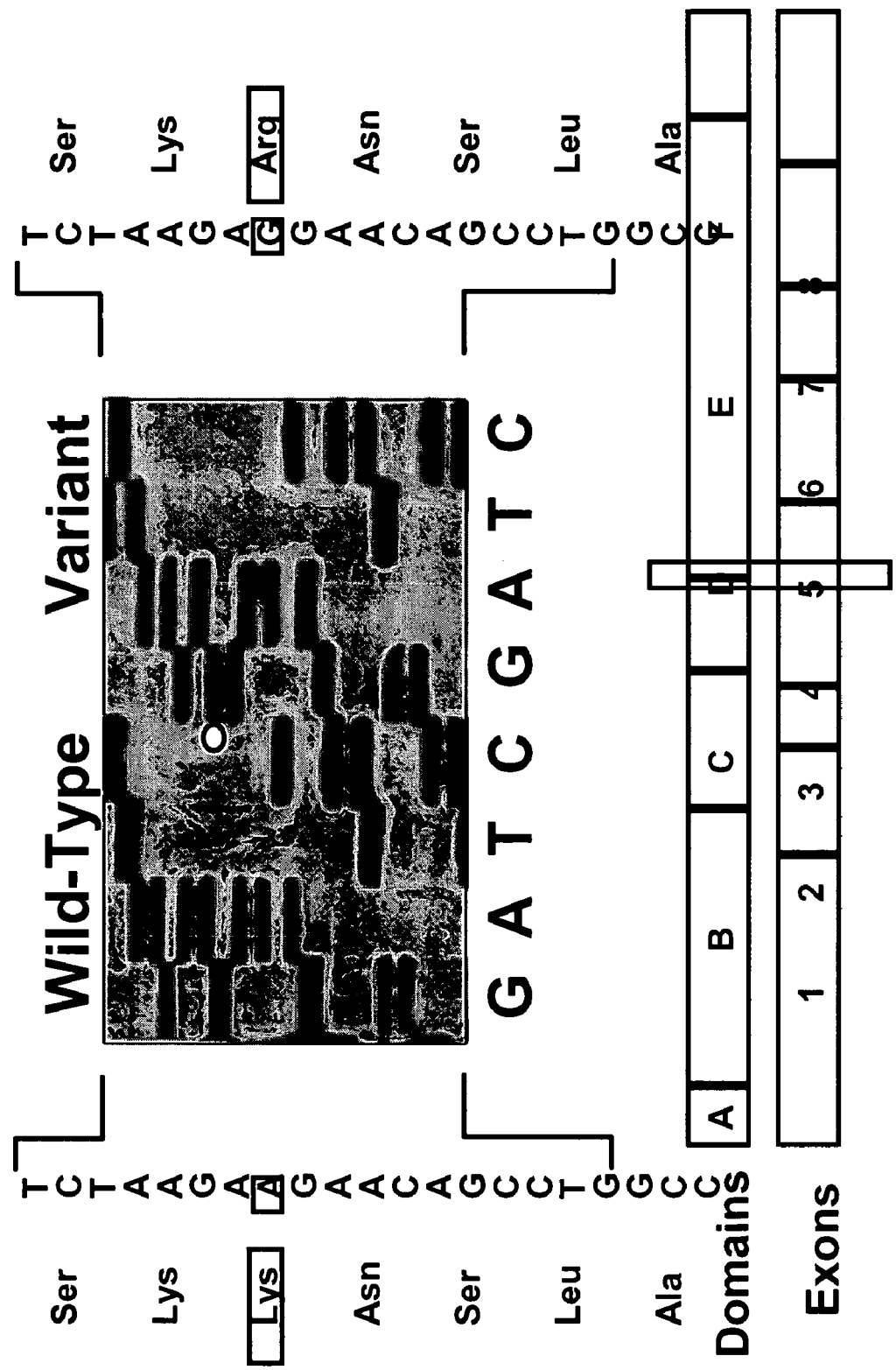
FIG. 2 illustrates sequence analysis of ER Variant (VAR) and Wild-Type (WT) cDNAs isolated from frozen breast hyperplastic tissue. A portion of the sequencing products are shown for wild-type and variant clones demarcating the location of the G transition and Arg substitution. ER domains A through E and the exons across these domains are shown on the bottom panel with the location of the Lys to Arg change demarcated with a box across exon 4 at the end of domain D.

Assay of Estrogen Receptor Alpha Sequence in Early Breast Disease cDNA was prepared by reverse transcription of RNA from 4 typical hyperplasias of the breast, to assay for an altered ER in early breast disease, followed by polymerase chain reaction (PCR) amplification using primers specific for the entire coding domain of ERα (across nucleotides 1182 to 1234). Cloning and sequencing of ER was performed as described in Fuqua et al. (1991) except restriction sites were incorporated into the primers to facilitate cloning into pGEM7zf (+) (Promega Corp., Madison, Wis.). Wildtype ER sequence was identified in two of these premalignant lesions (FIG. 2). However, in the other two lesions an ER α variant was identified with an A to G base pair transition at nucleotide 908 (FIG. 2, top panel). This transition introduces a Lys to Arg substitution at residue 303 within exon 4, at the border between the hinge domain D and the beginning of the hormone-binding domain E of ERα (FIG. 2, bottom diagram). Even though this substitution represents a conservative amino acid change, the size of the study was enlarged, since the data indicates that the amino-terminal region of the ERα hormone-binding domain is important in the generation of a complete transcriptional response in cells (Pierrat et al., 1994). Therefore, archival histological sections of 55 additional typical hyperplasias were microdissected, DNA was isolated, and direct genomic sequencing was performed using primers bordering ERα nucleotide 908. The same ER α alteration in 18/55 of these additional premalignant lesions was identified. Thus, the A908G ERα alteration was present in a total of 20/59 (34%) of the hyperplasias examined.

DNA was prepared from normal breast epithelium adjacent to the hyperplastic lesion of those samples that contained the A908G ERα alteration. The ERα variant sequence was detected in the normal adjacent epithelium of some of these samples tested. Thus, the A908G ER α transition is frequently present in premalignant lesions of the breast, and can occur in the adjacent normal-appearing breast epithelium.

Example 6

THE A908G ERα Mutation is a Somatic Mutation

Figure 3:
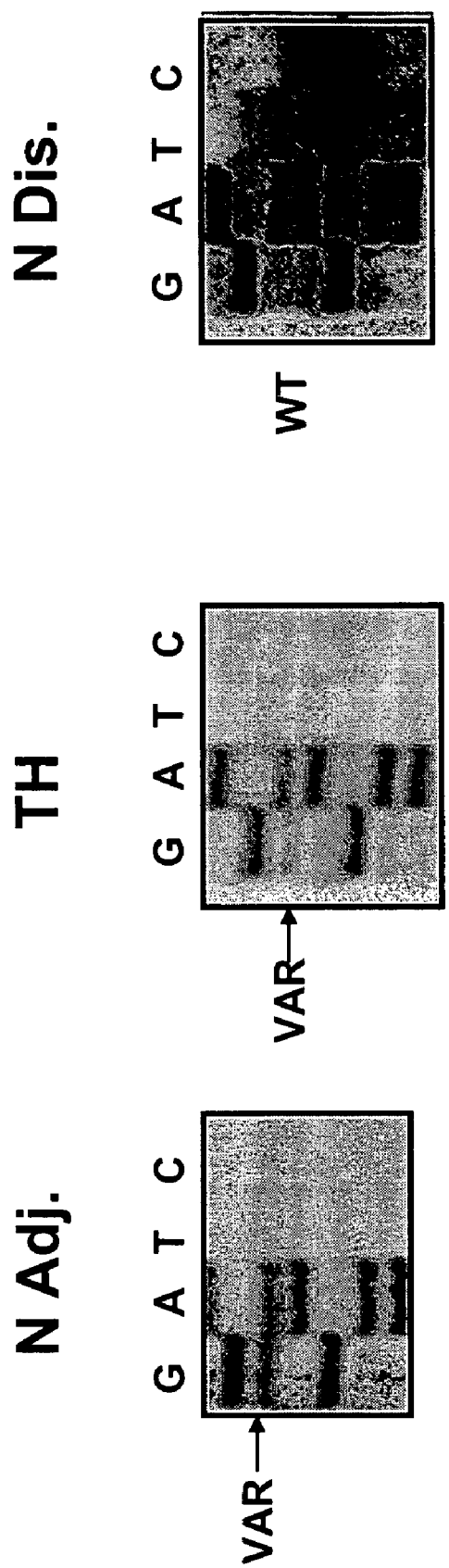
FIG. 3 demonstrates detection of the ER VAR sequence in archival breast specimens by identification of WT and VAR ER sequences in one patient with typical hyperplasia (TH). Normal adjacent breast epithelium (N Adj.), TH, and distant normal epithelium (N Dis.) were all available for analysis from this patient. The position of the A908G sequence is indicated by arrows.

To address whether the ER alteration might represent a somatic change in the breast, rather than a germ-line alteration or a naturally-occurring polymorphism within ERα, distant normal epithelium from 4 of the 20 patients with the A908G ER alteration in their hyperplastic lesion was microdissected. (Only 4 of the patients had sufficient normal distant tissue for analysis.) Manual microdissection on a light box under a dissecting microscope was performed to microdissect archival, formalin-fixed, paraffin-embedded tissue blocks and was precise enough to ensure at least 50% cellularity. DNA was liberated from the microdissected specimens and direct genomic sequence analysis performed. Genomic sequencing of one patient's samples is shown in FIG. 3. Variant A908G ER α sequence was detected along with WT sequence in the normal adjacent DNA (N Adj.) and the typical hyperplasia (TH) DNA from this patient, but the normal distant tissue (N Dis.) displayed only WT ER α sequence. All 4 of the patients with the variant ERα sequence in their hyperplastic lesion exhibited WT sequence in their distant normal tissue. To further strengthen this observation, normal DNA was also examined by direct genomic sequencing of 80 blood samples collected from patients without breast disease. There was no detection of the ERα variant sequence in any of these normal samples. Therefore, the A908G ERa alteration is a somatic mutation appearing frequently in association with breast hyperplasia. Thus, just as LOH can occur in morphologically normal ductal epithelium adjacent to breast cancers (Deng et al., 1996), and may therefore demarcate a localized region predisposed to the development of breast cancer, in a specific embodiment a somatic mutation in ERα within a localized region of normal breast epithelium defines a region of increased risk if the mutation confers a selective advantage to these cells.

Example 7

The A908G ERα Mutation Confers Selective Advantage to Cells

Figure 4:
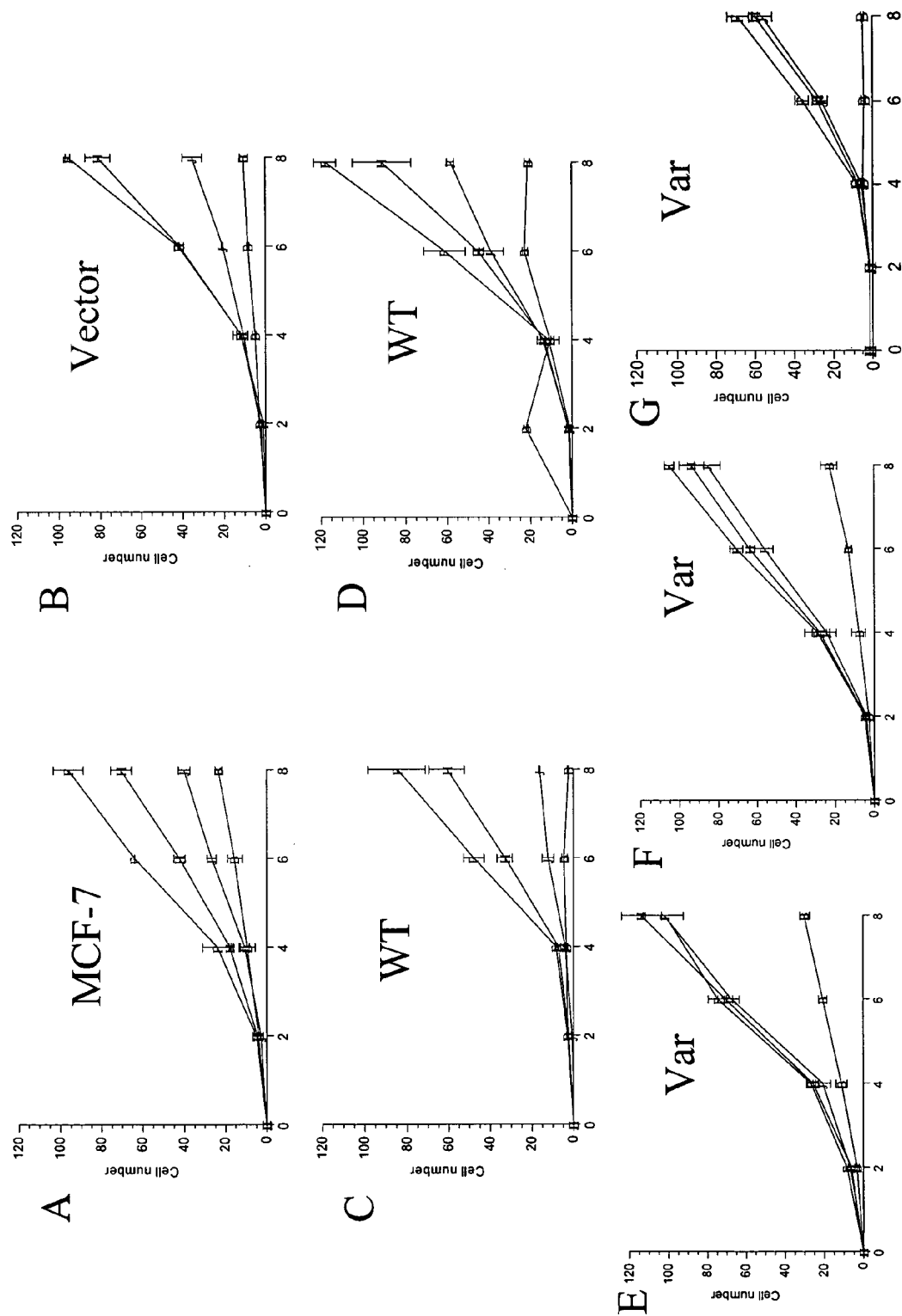
FIG. 4 illustrates growth curves of stable MCF-7 transfectants in response to increasing concentrations of estradiol in the media. Cells were plated at a density of $2 \times 10^4$ in media containing 10% charcoal-stripped, estrogen-free fetal calf serum and were either left untreated [■] or treated with the indicated estradiol concentrations ($1 \times 10^{-12}$[●], $1 \times 10^{-11}$ [π], $1 \times 10^{-9}$[♦] M). The medium was replaced every 48 h and the cells were harvested and counted on days 2, 4, 6, and 8, respectively. Cell number$\times 10^4$ is shown. Panel A demonstrates untransfected parental MCF-7 cells. Panel B demonstrates vector-alone stably transfected cells. Panels C and D demonstrate cells stably transfected with WT ER. Panels E, F, and D demonstrate cells stably transfected with the mutant ER.

The proliferative response to hormones in breast cancer cell transfectants containing the mutation was tested to determine if this ER mutation confers a selective advantage. A CMV-driven mammalian expression vector was prepared for WT ERα and utilized site-directed mutagenesis (Promega, Madison, Wis.) to generate the Lys303Arg substitution. The mutant expression vector was stably introduced into the ER-positive MCF-7 breast cancer cell line that normally expresses WT ERα. This cell line was chosen because it was determined that WT ERα was expressed along with the mutant in the original ⅔ typical hyperplastic lesions which were examined. As a control, the expression vector was also stably transfected alone into MCF-7 cells. Transfected clones were then cultivated in estrogen-depleted medium ($-E_2$) or medium supplemented with increasing amounts of estradiol ($10^{-12}$ to $10^{-9}$M). Both non-transfected MCF-7 cells (FIG. 4, panel A) and vector-alone transfected cells (panel B) exhibited typical estrogen dose response growth curves. Minimal cell growth stimulation was seen with $10^{-12}$M estradiol in these cells. Because it was possible that overexpression of the receptor alone might stimulate the growth of these cells, MCF-7 cells were also transfected with the expression vector for WT ERα, but their estrogen dose response curves (FIG. 4, panels C and D) were not different from the controls (Oesterreich et al., 1993). In contrast, three independent clones expressing the ERα mutation responded to extremely low levels of hormone ($10^{-12}$ M) (FIG. 4, panels E, F, and G) with nearly the same highly proliferative response seen at the highest concentration of estradiol used ($10^{-9}$ M).

Using analysis of variance (Box and Cox, 1996), it was determined that these were highly significant estrogen dose responses in the MCF-7, vector-alone transfected, and WT ERα-transfected cells (p=0.001), but that there was little or no difference in response to differing concentrations of estradiol in each of the three mutant ERα-transfected clones (p=0.41, 0.015, and 0.09, respectively, for clones E, F, and G). The growth-stimulatory effects of low levels of hormone in cells expressing the ERα mutation were even more evident when doubling times were calculated from the growth curves. For example, the doubling time for MCF-7 cells in $10^{-12}$ or $10^{-9}$ M estradiol is 2.2 vs. 1.3 days, respectively. The doubling times for cells expressing the ERα mutant is the same (1.3 days) at either $10^{-12}$ or $10^{-9}$ M of hormone. Thus, the expression of the ERα mutation confers a hypersensitivity to estrogen with an ability to be maximally stimulated in response to physiological levels ($10^{-12}$ to $10^{-11}$ M) of hormone. Thus, the A908G ERα mutation is a gain-of-function mutation that could have a significant biological role in early breast disease.

In one embodiment, one mechanism by which the ERα mutation confers hypersensitivity to low levels of hormone would be an increased binding affinity for estradiol. However, no differences in estradiol affinity were detected between the WT ERα and the A908G ERα mutation using saturation binding Scatchard analyses, nor were there differences in affinity for the antiestrogen tamoxifen.

Figure 5:
FIG. 5 demonstrates interaction of the WT and mutant ERs with SRC-1, SRC-2 and SRC-3 in vitro.

In an alternative embodiment, one mechanism by which the ERα mutation confers hypersensitivity to low levels of hormone might be altered affinity for ER co-regulators. It is now understood that many of the cell-type and tissue-specific effects of ERα are dependent on the cellular pool of co-regulatory factors that bind to and influence its transcriptional activity (reviewed in Horowitz et al., 1997), many of which act as signaling intermediates between the ER and the general transcriptional machinery, or directly have enzymatic activities such as histone acetyltransferase activity. The A908G ERα mutation occurs in a region implicated in binding to certain of these co-regulatory proteins, such as L7/SPA (Jackson et al., 1997) and the SRC-1 family of co-activators (Onate et al., 1998). For example, efficient interaction of SRC-1 with the progesterone receptor hormone-binding domain requires the presence of hinge sequences (Onate et al., 1998). Thus, the ability of WT and mutant ERα to interact with SRC-2 (TIF-2) (Voegel et al., 1996), a member of the SRC-1 family, was compared using in vitro GST pull-down assays (Ding et al., 1998). GST-WT ERα and GST-ERα mutant fusion constructs containing the hinge and hormone binding domains were prepared. Full-length SRC-1, SRC-2 and SRC-3 were synthesized in vitro in the presence of $[^{35}S]$methionine and then tested for specific hormone-dependent binding to the immobilized GST-ER fusion proteins (FIG. 5) by incubating with Sepharose beads containing immobilized GST, GST-WT ER, and GST-A908G mutant ER with or without estradiol. Bound SRC-1, SRC-2 and SRC-3 were eluted and observed by SDS-PAGE and autoradiography. Input SRC-1, SRC-2 and SRC-3 are shown (10%), as is nonspecific GST binding in the absence of estradiol. Increasing levels of estradiol used were: $4\times10^{-8}$, $5\times10^{-8}$, $6\times10^{-8}$, $7\times10^{-8}$, and $1\times10^{-6}$M. Both receptors bound SRC-1, SRC-2 and SRC-3 in the presence ($10^{-6}$ M), but not the absence of estradiol. However, the mutant required much less hormone for efficient binding. Even at the lowest estradiol concentration tested, $4\times10^{-8}$M, the mutant ER efficiently bound SRC-2 and SRC-3, whereas WT ERα exhibited neglible binding at this concentration. The mutant ER also bound SRC-1 co-activator, although not to the same extent as SRC-2 and SRC-3. This data indicates that the Lys303Arg substitution enhances SRC-1, SRC-2 and SRC-3 binding by lowering the concentration of hormone required to facilitate the formation of the co-activator:ER hydrophobic groove binding surface (Shiau et al., 1998) within the ER hinge/ligand binding domain. In another embodiment, an additional mechanism includes this residue in the ER as a site for acetylation. An Arg substitution at this site could render it incapable of being acetylated, and/or the substitution could reduce the net negative charge if surrounding Lys residues in the ER are indeed acetylated. Altered co-activator binding has also been reported for a Tyr537Asn ERα mutation (Tremblay et al., 1998) that was identified in a metastatic bone lesion from a breast cancer patient (Zhang et al., 1997). Thus, it is important that both of these in vivo ERα mutations drastically affect the ability of the receptor to bind to co-regulatory proteins.

Example 8

Single Strand Conformation Polymorphism (SSCP) Analysis of ER Mutation

Figure 6:
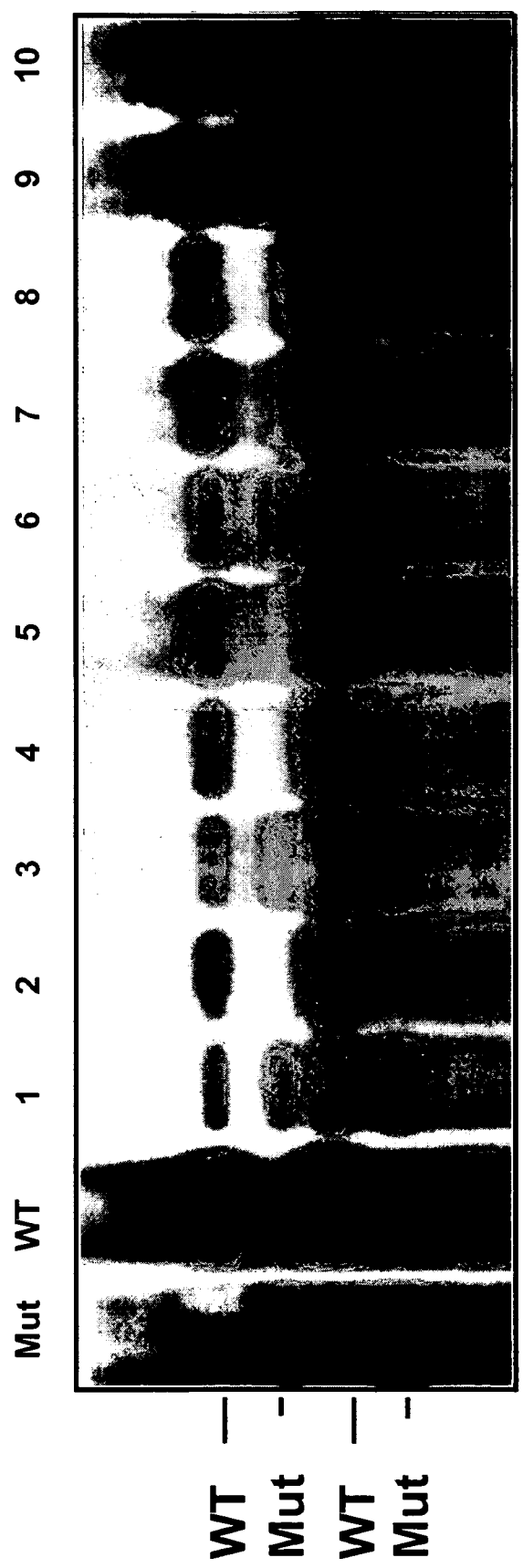
FIG. 6 demonstrates detection of the ER Mutant (Mut) in archival breast specimens, including identification of WT and Mut ER alleles in 10 typical breast hyperplasias. Both Mut and WT plasmid DNAs were included as positive controls for the location of the migration of their respective alleles (first two lanes). The ten hyperplastic lesions are labeled 1 through 10.

A skilled artisan recognizes that there are multiple methods known in the art to identify a mutation, including SSCP. Additional clinical samples were examined by manually microdissecting permanent sections of 10 typical hyperplasias. Manual microdissection on a light box under a dissecting microscope was performed to microdissect archival, formalin-fixed, paraffin-embedded tissue blocks and was precise enough to ensure at least 50% cellularity. DNA was liberated from the microdissected specimens as described (Fuqua et al., 1991) and SSCP analysis performed (Orita et al., 1989) using primers spanning across ER nucleotide 908 (FIG. 6). SSCP was performed as previously described (Elledge et al., 1993) except ER primers were used for PCR amplification (nucleotides 1093-1112 (5' primer; SEQ ID NO:15) and 1231-1250 (3' primer; SEQ ID NO:16) of the ER gene (Greene et al., 1986). The gels were electrophoresed in 0.5×TBE at room temperature for 14 h. To be scored as having an alteration, a DNA sample had to produce an abnormal SSCP pattern using separate DNA aliquots and amplified on different days with negative controls.

Five of the hyperplasias (samples 2, 4, 5, 7, and 8) displayed band mobilities which were identical to those of the complementary strands of the PCR fragment from the WT ER control DNA. However, in five of the hyperplasias (samples 1, 3, 6, 9, and 10) four bands could be detected. These results indicated that the DNA from these later five hyperplasias had two different ER alleles, one WT and the other migrating identical with the mutant (Mut) ER allele. Further proof that these faster migrating bands contained the A908G transition was obtained by cutting the region corresponding to the Mut band from the dried gel, cloning the fragment, and dideoxy-sequence analyzing to confirm.

Example 9

Oligonucleotide Mismatch Mutation Detection

A sensitive oligonucleotide mismatch hybridization method (Moul et al., 1992) was used to detect the ER alleles in a cancer patient. In addition, laser capture microdissection was utilized to more precisely enrich for the specific lesions present concomitantly in this patient.

A nested PCR amplification procedure was used to amplify the laser capture microdissected material (Bonner, 1997) where the outside primers correspond to those used in the SSCP analysis described above in a 30 µl reaction volume, and then 1.5 µl of this was then reamplified with ER primer sequences corresponding to nucleotides 1101-1130 (5') and 1220-1239 (3') of the ER gene (Greene et al., 1986). The samples were then denatured in 0.4 M NaOH, 25 mM EDTA at 95° C., then neutralized with 1 M Tris-HCl pH 7.4 before slotting on the nylon membranes. Oligonucleotide probes corresponding to the WT (SEQ ID NO:33; 5'-GCTCTAA-GAAGAACAGCCTG-3') or Mutant (SEQ ID NO:34; 5'-GCTCTAAGAGGAACAGCCTG-3') (corresponding to nucleotides 1191 to 1210 of the ER gene (Greene et al., 1986)) were end-labeled with T4 kinase. The membrane was prehybridized in 5×SSPE, 0.5% SDS, 5×Denhardt's and washed at 60° C. 2×SSPE, 0.1% SDS followed by a wash at 68° C. in 5×SSPE. 0.1% SDS. Control WT or Mut plasmid DNAs were also amplified, slotted, and hybridized as positive controls for hybridization; samples without added DNA were included as negative controls during amplification.

Figure 7:
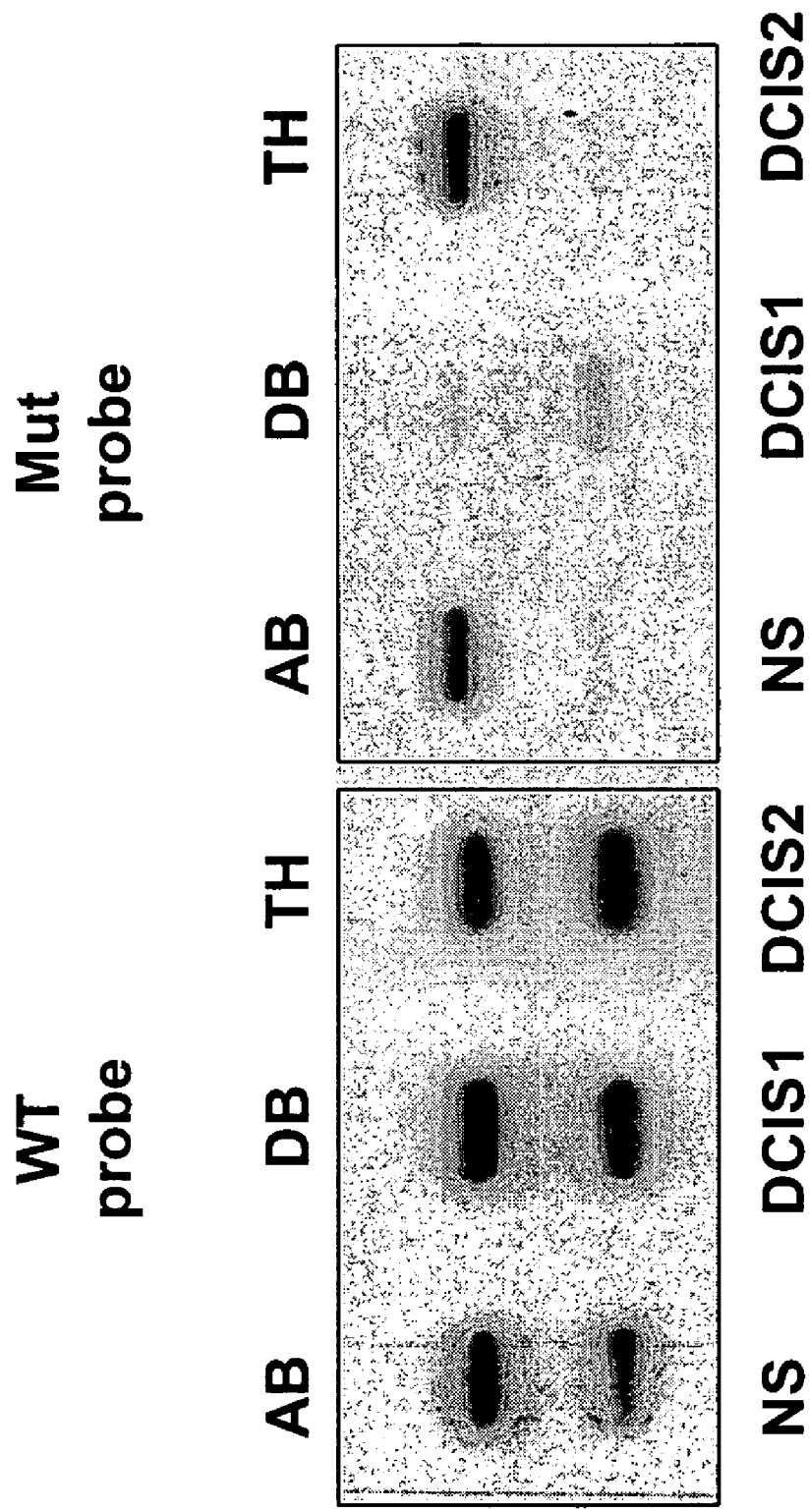
FIG. 7 illustrates oligonucleotide mismatch hybridization of one patient with concurrent breast lesions. Laser capture microdissection was used to precisely microdissect with an enrichment of >90% cellularity. PCR-amplified fragments were obtained from normal breast epithelium adjacent to a hyperplasia (AB), normal breast epithelium distant from malignant breast lesions (DB), TH, normal skin (NS) and two different DCIS lesions (DCIS 1 and 2) and slotted in duplicate onto nylon membranes (Micro Separation, Inc., Westboro, Mass.). The panel on the left was hybridized with an oligonucleotide to the WT ER sequence, while the panel on the right was hybridized with an oligonucleotide specific for the Mut sequence.

The variant sequence was detected in the normal adjacent breast epithelium (AB), the hyperplastic lesion (H), and one ductal carcinoma in situ (DCIS) lesion using an oligonucleotide probe specific for the variant, but not in normal skin (NS), normal distant breast epithelium (DB), or another independent DCIS lesion in this patient (FIG. 7, right panel). Both WT (FIG. 7, left panel) and mutant ER alleles were present in this patient.

Example 10

Incidence of the A908G Mutation in Invasive Breast Cancers

In a specific embodiment of the present invention, breast cancer samples from invasive breast tumors are assayed by standard methods, such as those described herein, for the A908G mutation in estrogen receptor alpha nucleic acid sequence. A skilled artisan recognizes that there are presently two types of invasive breast cancer: Node-negative and Node-positive. In approximately half of women with invasive breast cancer, the lymph nodes are invaded (Node-positive), and there are also micrometastases elsewhere within the body. In approximately half of women with invasive breast cancer, the cancer has not spread to the lymph nodes.

|  | Ca. from Node-negative women | Ca. from Node-positive women |
|---|---|---|
| Wild-type | 16 | 4 |
| Mutant | 10 | 23 |

(p = 0.00062 Fisher's Exact Test, two sided)

Therefore, the frequency of the mutation in invasive breast tumors=33/53=62%. Thus, the A908G mutation is identified in both Node-negative and Node-positive invasive breast cancers.

Example 11

Screening for Antagonists and Agonists of ERα K303R Polypeptide

In some embodiments of the present invention, candidates for drugs are screened which are useful for treatment of a breast cancer related to the A908G mutation in ERα polynucleotide and/or the ERα K303R polypeptide which it encodes. In specific embodiments, antagonists or agonists are screened for which affect the activity of the ERα K303R polypeptide.

A skilled artisan recognizes that a variety of methods known in the art are available to screen for antagonists or agonists of ERα K303R polypeptide. For example, transfection assays are utilized (such as described in Barkhem et al. (1997); Cowley et al. (1997); and Sun et al. (1999), all of which are incorporated by reference herein in their entirety) wherein a cell is transiently or stably transfected with an expression vector comprising the ER form to be tested against, a reporter expression construct operably linked to at least one estrogen response element, such as 5'-AGGTCA-3' (SEQ ID NO:36); 5'-TGACCT-3' (SEQ ID NO:37); 5'-GGT- CAnnnTGACC-3' (SEQ ID NO:38); 5'-AATCAnnnTGACT-3' (SEQ ID NO:39); 5'-GGTCA-3' (SEQ ID NO:40); 5'-TGGTC-3' (SEQ ID NO:41); 5'-TGACC-3' (SEQ ID NO:42); 5'-ATTCGATCAGGGCGGGGCGAGC-3' (from SP1; SEQ ID NO:43); 5'-GGGCA(N)$_{16}$GGCGGG-3' (c-myc; SEQ ID NO:44); 5'-GGTCA(N)$_{21}$GGCGG-3' (ckb; SEQ ID NO:45); 5'-GGGCCGGG(N)$_{10}$GGTCA-3' (cathepsin D; SEQ ID NO:46); 5'-GGGCA-3' (hsp27; SEQ ID NO:47); 5'-GGTAA-3' (cathepsin D; SEQ ID NO:48); 5'-GGTCA(N)3TGCCC-3' (uteroglobin; SEQ ID NO:49); 5'-GGGGCGTGG-3' (c-fos; SEQ ID NO:22); 5'-CCGCCCC-3' (e2f; SEQ ID NO:26); 5'-TGA(C/G)TCA-3' (AP1; SEQ ID NO:8). A compound to be tested is administered to the cell, and the expression level of the reporter expression construct is assayed in the presence of the test compound and compared to expression levels in its absence. A test compound which downregulates expression of the reporter polynucleotide is considered an antagonist, and a test compound which upregulates expression of the reporter polynucleotide is considered an agonist.

In alternative embodiments for drug/antagonist/agonist screening, a two hybrid assay is performed, such as is described in Slentz-Kesler et al. (2000), incorporated by reference herein in its entirety. In a specific embodiment, a polynucleotide encoding the ERα K303R polypeptide as a fusion polypeptide with a DNA binding domain is transformed into a yeast or mammalian cell. The population of corresponding yeast or mammalian cells further comprise a library of expression vectors producing chimeric polypeptides comprising a DNA activation and a library candidate. Interaction of the ERα K303R polypeptide with a particular library candidate is visualized by assaying expression of a reporter sequence expression influenced by the interaction of the corresponding DNA activation and binding domains. A skilled artisan recognizes that multiple DNA activation and binding domains are available, including GAL4 or LexA. Also, controls are performed to eliminate any false positives.

In another embodiment to identify and design drugs for ERα K303R polypeptide-associated breast cancer, particularly antagonists and agonists, a phage peptide display assay is employed, such as is described in Sparks et al. in *Phage Display of Peptides and Proteins, A Laboratory Manual* (Academic, San Diego), incorporated by reference herein. In this embodiment, an affinity-tagged labeled ERα K303R polypeptide is exposed to a nitrocellulose membrane comprising bacteriophage plaques each of which comprise a peptide. Binding of the ERα K303R polypeptide to the peptide is assayed, and the resultant peptides are identified. In some embodiments, the affinity selection of the phage-displayed peptide libraries is conducted on the ERα K303R polypeptide in different conditions, such as in an apo form, ligand-bound form, and so forth. The resultant peptides are analyzed, allowing rational drug design to ensue based on the analysis.

In an additional embodiment, other methods are known to evaluate the effects of an antagonist vs. an agonist of a receptor-binding substance on a selected type of cells containing an endogenouse intra-cellular hormone receptor, such as is described in U.S. Pat. No. 5,578,445, incorporated by reference herein. Therein, an in vitro method is disclosed wherein a test substance and a reference substance, known to be either an antagonist or an agonist of the receptor, is incubated with cells, and the magnitude of the selected cellular response resulting from the hormone/receptor interaction is analyzed.

In another embodiment, drug candidates/antagonists/agonists for ERα K303R polypeptide are analyzed by mass spectrometry (Witkowska et al., 1997) or by X-ray crystallography (Shiau et al., 1998), both of which are incorporated by reference herein in their entirety. A skilled artisan recognizes that the National Center for Biotechnology Information provides a structural database (http://www.ncbi.nlm.nih.gov/entrez/query.fcgi?db=PubMed) containing many protein structures, including estrogen receptor. Analyses of the ERα K303R polypeptide by these methods provide significant structural detail so that, for example, an antagonist to fit a particular structural domain can be designed. In one embodiment, X-ray crystallography is performed on the ERα K303R polypeptide bound to a specific ligand, such as estradiol, tamoxifen, raloxifene, droloxigene, GW 5638, idoxifene, CP336156, or LY353381. Such an analysis facilitates design of a drug which will antagonize the activity of the ERα K303R polypeptide, such as for the treatment of breast cancer. For mass spectrometry methods to facilitate drug screen/antagonist/agonist analysis, methods may be employed which are similar to Witkowska et al. (1997), wherein structural comparisons were made between two structurally similar compounds. In a particular embodiment, the mass spectrometry analysis provides information on binding sites for cofactors.

In one embodiment of the present invention, there is a method of designing an agent which affects the activity of an estrogen receptor alpha K303R polypeptide, comprising determining the crystal structure of a purified estrogen receptor alpha K303R polypeptide; and analyzing a model of the crystal structure, wherein the agent is designed based on the analysis.

In another embodiment of the present invention there is a method of designing an agent which affects the activity of an estrogen receptor alpha K303R polypeptide, comprising determining the crystal structure of a purified estrogen receptor alpha K303R polypeptide in the presence of a compound which interacts with the estrogen receptor alpha K303R polypeptide; and analyzing a model of the crystal structure, wherein the agent is designed based on the analysis. In a specific embodiment, the analyzing step comprises computer modeling. In another specific embodiment, the crystal structure is determined in the presence of an estrogen receptor ligand.

In an additional embodiment of the present invention, there is a method of designing an agent which affects the activity of an estrogen receptor alpha K303R polypeptide, comprising analyzing the structure of the polypeptide by mass spectrometry, wherein the structure of the polypeptide suggests the design of the activity-affecting agent. In a specific embodiment, the activity-affecting agent is an antagonist. In another specific embodiment, the activity-affecting agent is an agonist.

Example 12

Significance of the Present Invention

In summary, it is shown that a large proportion of premalignant breast hyperplasias express an altered ERα that is hypersensitive to the effects of estrogen. Furthermore, the alteration results from a somatic mutation in the breast with this mutation affecting the ability of the receptor to bind to the SRC-1, SRC-2, and SRC-3 co-activators. There is an increasing body of evidence, both epidemiological (Dupont and Page, 1985) and molecular (O'Connell et al., 1998), suggesting that these premalignant lesions are both risk factors and direct precursors of invasive breast cancer. However, hyperplasias are relatively common in the breast, and only a small fraction of them will progress to cancer. Prior to the methods and compositions of the present invention, those in the art have been unable to differentiate which of these lesions are genetically stable, or the biological differences driving some of them to progress. An ERα mutation that confers a proliferative advantage, such as hypersensitivity to hormone, in a specific embodiment provides a favorable cellular environment accelerating the accumulation of additional genetic events important for tumor progression.

Premalignant breast lesions are microscopic masses with a positive growth imbalance, and the hypersensitive ERα mutation is likely an important factor contributing to this imbalance. Hormone levels normally fluctuate during the menstrual cycle in premenopausal women, and levels are considerably lower in postmenopausal women. In one embodiment, an ER mutation hypersensitive to estradiol provides a continuous mitogenic stimulus to the breast epithelium even during phases of low circulating hormone, especially in postmenopausal women, thus elevating their risk for breast cancer. Thus, in a preferred embodiment, there is a correlation between risk for breast cancer and expression of this ERα mutation, which will allow genetic analysis for the mutation in premalignant lesions to be crucial to identify patients who would benefit from preventive measures.

Example 13

Ductal Hyperplasias in K303R Transgenic Mice

Figure 8:
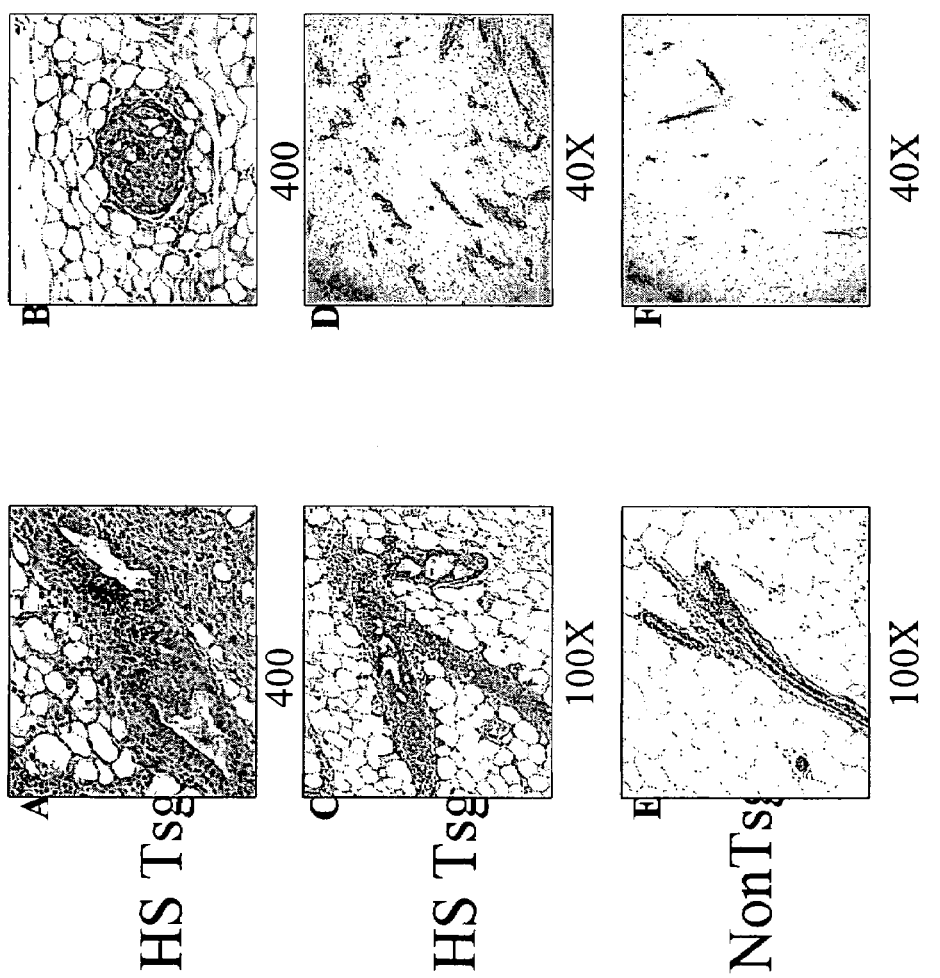
FIGS. 8A through 8D demonstrates ductal hyperplasias in K303R transgenic mice.
FIGS. 8E-8F show nontransgenic mammary gland controls.

Transgenic mice expressing the K303R mutation were generated by standard means in the art. The mice at the time of filing of the nonprovisional application have matured to 18 months, and they have developed ductal hyperplasias (FIG. 8, panels A through D). Nontransgenic mainmary glands are shown in panels 8E and 8F. The H&E-stained histological sections shown in panels 8A and 8B clearly demonstrate the development of ductal hyperplasias in the transgenic mice with luminal epithelial cells beginning to stratify in the ductal lumen in the mammary glands. Panel 8B shows a duct whose lumen is completely filled with epithelial cells. In a specific embodiment of the present invention, the hypersensitive ER mutation provides a proliferative advantage, especially by providing a continuous mitogenic stimulus to the epithelium even in an environment of low circulating hormones, such as these virgin mice.

Ductal hyperplasias are composed of both an increase in the number of epithelial cell layers within the duct (shown in panel 8C), as well as an increase in the number of small ducts within a given area (shown in panel 8D). These increases in the transgenic animals are more clearly observed when one compares the histological sections from nontransgenic mammary glands (shown in panels 8E and 8F).

Figure 9:
FIG. 9 shows a comparison of ductal epithelium from K303R transgenic mice versus nontransgenic mice.
Figure 9:

FIG. 9 shows that the K303R transgenic animals have increased proliferation as compared to nontransgenic animals in the ductal epithelium. Proliferation was measured by immunohistochemistry with an antibody to phosphorylated histone H1b, a surrogate marker of S-phase.

Thus, the data in FIGS. 8 and 9 show that expression of the K303R mutation, which was originally identified in human breast hyperplastic lesions, is indeed an important factor contributing to abnormal ductal growth and the development of proliferating ductal hyperplasias.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference herein.

Patents

U.S. Pat. No. 3,817,837, issued Jun. 18, 1974
U.S. Pat. No. 3,850,752, issued Nov. 26, 1974
U.S. Pat. No. 3,939,350, issued Feb. 17, 1976
U.S. Pat. No. 3,996,345, issued Dec. 7, 1976
U.S. Pat. No. 4,196,265, issued Apr. 1, 1980
U.S. Pat. No. 4,215,051, issued Jul. 29, 1980
U.S. Pat. No. 4,275,149, issued Jun. 23, 1981
U.S. Pat. No. 4,277,437, issued Jul. 7, 1981
U.S. Pat. No. 4,366,241, issued Dec. 28, 1982
U.S. Pat. No. 4,340,535, issued Jul. 20, 1982
U.S. Pat. No. 4,472,509, issued Sep. 18, 1984
U.S. Pat. No. 4,554,101, issued Nov. 19, 1985
U.S. Pat. No. 4,683,195, issued Jul. 28, 1987
U.S. Pat. No. 4,683,202, issued Jul. 28, 1987
U.S. Pat. No. 4,740,463, issued Apr. 26, 1988
U.S. Pat. No. 4,800,159, issued Jan. 24, 1989
U.S. Pat. No. 4,816,567, issued Mar. 28, 1989
U.S. Pat. No. 4,867,973, issued Sep. 19, 1989
U.S. Pat. No. 4,883,750, issued Nov. 28, 1989
U.S. Pat. No. 4,938,948, issued Jul. 3, 1990
U.S. Pat. No. 5,021,236, issued Jun. 4, 1991
U.S. Pat. No. 5,138,045, issued Aug. 11, 1992
U.S. Pat. No. 5,196,066, issued Mar. 23, 1993
U.S. Pat. No. 5,262,311, issued Nov. 16, 1993
U.S. Pat. No. 5,279,721, issued Jan. 18, 1994
U.S. Pat. No. 5,342,774, issued Aug. 30, 1994
U.S. Pat. No. 5,565,332, issued Oct. 15, 1996
U.S. Pat. No. 5,633,365, issued May 27, 1997
U.S. Pat. No. 5,665,549, issued Sep. 9, 1997
U.S. Pat. No. 5,693,762, issued Dec. 2, 1997
U.S. Pat. No. 5,840,873, issued Nov. 24, 1998
U.S. Pat. No. 5,843, 640, issued Dec. 1, 1998
U.S. Pat. No. 5,843,650, issued Dec. 1, 1998
U.S. Pat. No. 5,843,651, issued Dec. 1, 1998
U.S. Pat. No. 5,843,663, issued Dec. 1, 1998
U.S. Pat. No. 5,846,708, issued Dec. 8, 1998
U.S. Pat. No. 5,846,709, issued Dec. 8, 1998
U.S. Pat. No. 5,846,717, issued Dec. 8, 1998
U.S. Pat. No. 5,846,726, issued Dec. 8, 1998
U.S. Pat. No. 5,846,729, issued Dec. 8, 1998
U.S. Pat. No. 5,846,783, issued Dec. 8, 1998
U.S. Pat. No. 5,849,481, issued Dec. 15, 1998
U.S. Pat. No. 5,849,483, issued Dec. 15, 1998
U.S. Pat. No. 5,849,486, issued Dec. 15, 1998
U.S. Pat. No. 5,849,487, issued Dec. 15, 1998
U.S. Pat. No. 5,849,497, issued Dec. 15, 1998
U.S. Pat. No. 5,849,546, issued Dec. 15, 1998
U.S. Pat. No. 5,849,547, issued Dec. 15, 1998
U.S. Pat. No. 5,851,770, issued Dec. 22, 1998
U.S. Pat. No. 5,851,772, issued Dec. 22, 1988
U.S. Pat. No. 5,853,990, issued Dec. 29, 1998
U.S. Pat. No. 5,853,993, issued Dec. 29, 1998
U.S. Pat. No. 5,853,992, issued Dec. 29, 1998
U.S. Pat. No. 5,856,092, issued Jan. 5, 1999
U.S. Pat. No. 5,858,652, issued Jan. 12, 1999
U.S. Pat. No. 5,861,244, issued Jan. 19, 1999
U.S. Pat. No. 5,863,732, issued Jan. 26, 1999
U.S. Pat. No. 5,863,753, issued Jan. 26, 1999
U.S. Pat. No. 5,866,331, issued Feb. 2, 1999
U.S. Pat. No. 5,866,336, issued Feb. 2, 1999
U.S. Pat. No. 5,866,337, issued Feb. 2, 1999
U.S. Pat. No. 5,900,481, issued May 4, 1999

U.S. Pat. No. 5,905,024, issued May 18, 1999
U.S. Pat. No. 5,910,407, issued Jun. 8, 1999
U.S. Pat. No. 5,912,124, issued Jun. 15, 1999
U.S. Pat. No. 5,912,145, issued Jun. 15, 1999
U.S. Pat. No. 5,912,148, issued Jun. 15, 1999
U.S. Pat. No. 5,916,776, issued Jun. 29, 1999
U.S. Pat. No. 5,916,779, issued Jun. 29, 1999
U.S. Pat. No. 5,919,626, issued Jul. 6, 1999
U.S. Pat. No. 5,919,630, issued Jul. 6, 1999
U.S. Pat. No. 5,922,574, issued Jul. 13, 1999
U.S. Pat. No. 5,925,517, issued Jul. 20, 1999
U.S. Pat. No. 5,925,525, issued Jul. 20, 1999
U.S. Pat. No. 5,928,862, issued Jul. 27, 1999
U.S. Pat. No. 5,928,869, issued Jul. 27, 1999
U.S. Pat. No. 5,928,870, issued, Jul. 27, 1999
U.S. Pat. No. 5,928,905, issued Jul. 27, 1999
U.S. Pat. No. 5,928,906, issued Jul. 27, 1999
U.S. Pat. No. 5,929,227, issued Jul. 27, 1999
U.S. Pat. No. 5,932,413, issued Aug. 3, 1999
U.S. Pat. No. 5,932,451, issued Aug. 3, 1999
U.S. Pat. No. 5,935,791, issued Aug. 10, 1999
U.S. Pat. No. 5,935,825, issued Aug. 10, 1999
U.S. Pat. No. 5,939,291, issued Aug. 17, 1999
U.S. Pat. No. 5,942,391, issued Aug. 24, 1999
European Application No. 320 308
European Application No. 329 822
European Application No. EP 431,523
European Application No. EP 329,822
GB Application No. 2 202 328
PCT Application No. PCT/US87/00880
PCT Application No. PCT/US89/01025
PCT Application WO 88/10315
PCT Application WO 89/06700
PCT Application WO 90/07641
PCT Application No. PCT/US87/00880
PCT Application No. PCT/US89/01025
PCT Application WO 88/10315
PCT Application WO 89/06700
PCT Application WO 94/10343
PCT Application WO 94/23050
PCT Application WO 95/10265

PUBLICATIONS

Abbondanzo et al., Breast Cancer Res. Treat., 16: 182 (#151), 1990.
Albonico G, Querzoli P, Feretti S, Magri E, Nenci I. Biophenotypes of breast carcinoma in situ defined by image analysis of biological parameters. Path Res Pract 1996;192:117-123.
Alfthan et al., Cancer Res., 52:4628-4633, 1992.
Allegra J C, Lippman M E, Green L, Barlock A, Simon R, Thompson E B, et al. Estrogen receptor values in patients with benign breast disease. Cancer 1979;44: 228-231.
Allred et al., Breast Cancer Res. Treat., 16: 182(#149), 1990.
Altschul et al., J. Mol. Biol., 215:403-410, 1990.
Anandappa et al. Int. J. Cancer 88:209-216, 2000.
Ando et al., Int. J. Cancer, 40:12-17, 1987.
Antibodies: A Laboratory Manual, Cold Spring Harbor Laboratory, Cold Spring Harbor Press, Cold Spring Harbor, N.Y., 1988.
Atherton et al., Biol. of Reproduction, 32, 155-171, 1985.
Ausubel, Brent, Kingston, Moore, Seidman, Smith, Struhl, eds., Current Protocols in Molecular Biology (Wiley, New York), 1994.
Ballard-Barbash R, Griffin M R, Fisher L D, et al. Estrogen receptors in breast cancer. Am J Epidemiol 1986; 124: 77-84.
Barany and Merrifield, "The Peptides, Gross and Meienhofer, eds", Academic Press, New York, 1-284, 1979.
Barnes R, Masood S. Potential value of hormone receptor assay in carcinoma in situ of breast. Am J Clin Pathol 1990;94:533-537.
Basombrio, Cancer Res., 30:2458-2462, 1970.
Berardo M, Hilsenbeck S G, Allred D C. Histological grading of noninvasive breast cancer and its relationship to biological features. Lab Invest 1996;74(15A):#68.
Berberian et al., Science, 261:1588-1591, 1993.
Bittner et al., Methods in Enzymol, 153:516-544, 1987.
Bobrow L G, Happerfield L C, Gregory W M, Springall R D, Millis R R. The classification of ductal carcinoma in situ and its association with biological markers. Sem Diagnostic Pathol 1994; 11: 199-207.
Bocker W, (1997) Preneoplasia of the breast. Verh Dtsch Ges Pathol 81:502-13.
Bodis S, Siziopikou K P, Schitt S J, Harris J R, Fisher D E. Extensive apoptosis in ductal carcinoma in situ of the breast. Cancer 1996;77:1831-1835.
Boel et al., Immunity, 2(2):167-75, 1995.
Bonner, R. F. Science 278, 1481 (1997)
Boon et al., J. Exp. Med., 152:1184-1193, 1980.
Boring et al., Cancer Statistics, 1994.
Bose S, Lesser M L, Norton L, Rosen P P. Immunophenotype of intraductal carcinoma. Arch Pathol Lab Med 1996;120(1):81-85.
Box, G. E. P. and Cox, D. R.: Analysis of transformations. J Royal Statist Soc Series B, 26: 211-251, 1996.
Brooks S C, Saunders D E, Singhakowinta A, et al. Relation of tumor content with response of patient to endocrine therapy. Cancer 1980; 46:2775-8.
Brown et al., Breast Cancer Res. Treat., 16: 192(#191), 1990.
Brunner et al., J. Immunol., 124:1627-1634, 1980.
Burstein N A. Overall principles of cancer management. In: Cancer manual, $6^{th}$ ed. Boston: American Cancer Society, Mass. Div., 1982. pp. 67-71.
Bystryn et al., Cancer Res., 45:5603-5607, 1985.
Campbell, In: Monoclonal Antibody Technology, Laboratory Techniques in Biochemistry and Molecular Biology, Vol. 13, Burden & Von Knippenberg (Eds.), Elseview, Amsterdam, pp. 71-74; 75-83, 1984.
Capaldi et al., Biochem. Biophys. Res. Comm., 76:425, 1977.
Cardiff, R. D. et al. Biology of breast neoplasia. Cancer. June vol. 39:Supplement:2734-2746.
Carubia et al., Biochem. Biophys. Res. Commun., 120: 500-504, 1984.
Chaudhuri B, Crist K A, Mucci S, Malafa M, Chaudhuri P K. Distribution of estrogen receptor in ductal carcinoma in situ of the breast. Surgery 1993; 113:134-137.
Chen et al., Proc. Am. Urol. Assn., 153: 267A, 1995.
Chien et al., Proc. Nat. Acad. Sci. USA, 88:9578-9582, 1991.
Chinault and Carbon, Gene, 5:111-126, 1979.
Chomczynski and Mackey, Anal. Biochem., 225:163-164, 1995.
Cleary et al., Trends Microbiol., 4:131-136, 1994.
Cohen, Science, 259:1691-1692, 1993
Cole et al., Endocrinology, 113:1176-1178, 1983.
Cooper J A, Rohan T E, Cant E L, et al. Risk factors for breast cancer by oestrogen receptor status: a population-based case-control study. Br J Cancer 1989;59: 119-25.

Cox et al., J. Virol., 67(9):5664-5667, 1993.

Datta et al., J. Clin. Oncol., 12:475-482, 1994.

Degenshein G A, Bloom N, Tobin E. The value of progesterone receptor assays in the management of advanced breast cancer. Cancer 1980;46:2789-93.

Deng, G., Lu, Y., Zlotnikov, G., Thor, A. D., Smith, H.: Loss of heterozygosity in normal tissue adjacent to breast carcinomas. Science, 274: 2057-2059, 1996.

Denton et al., J Pathol, 167(2):187-91, 1992.

De Jager R, Abdel-Nabi H, Serafini A, Pecking A, Klein J L, Hanna M G Jr., "Current status of cancer immunodetection with radiolabeled human monoclonal antibodies" Semin Nucl. Med 23(2):165-179, 1993.

De Potter C R, Praet M M, Slavin R E, Verbeeck P, Roels H J. Feulgen DNA content and mitotic activity in proliferative breast disease: a comparison with ductal carcinoma in situ. Histopathology 1987;7:1307-1319.

Dholakia et al., J. Biol. Chem., 264, 20638-20642, 1989.

Diamond et al., J. Urol., 128:729-734, 1982.

Ding, X. F, et al.: Nuclear receptor-binding sites of coactivators glucocorticoid receptor interacting protein 1 (GRIP1) and steroid receptor coactivator 1 (SRC-1): multiple motifs with differentbinding specificities. Mol Endocrinol, 12:302-313, 1998.

Donahue et al., J. Biol. Chem., 269: 8604-8609, 1994.

Donegan W L. Prognostic factors, stage, and receptor status in breast cancer. Cancer 1992;70:1755-64.

Doolittle M H and Ben-Zeev O, "Immunodetection of lipoprotein lipase: antibody production, immunoprecipitation, and western blotting techniques" Methods Mol Biol., 109:215-237, 1999.

Dupont, W. D. and Page, D. L.: Risk factors for breast cancer in women with proliferative breast disease. N Engl J Med., 31: 146-151,1985.

Dzau et al., Proc. Natl. Acad. Sci. USA, 93:11421-11425, 1996.

Elder et al., Cancer Res., 49:5091-5096, 1989.

Elledge R M, McGuire W L. Prognostic factors and therapeutic decisions in axillary node-negative breast cancer. Ann Rev Med 1993;44:201-10.

Fearon et al., Am J Clin Nutr, 47 (1):42-48, 1988.

Ferguson D J P, Anderson T J. Morphological evaluation of cell turnover in relation to the menstrual cycle in the "resting" human breast. Br J Cancer 1981;44:177-181.

Fidler and Hart, Science, 217:998-1001, 1982.

Fidler, et al., Res Immunol., 144:(4)284-7; discussion 294-8, 1983.

Fisher E R, Costantino J, Fisher B, Palekar A S, Paik sM, Suarex C M, et al. Pathologic findings from the National Surgical Adjuvant Breast Progect (NSABP) protocol B-17. Cancer 1996;78:1403-1416.

Fitzpatrick, T. B., In: The American Cancer Society Cancer Handbook. Ch. 30, pp. 532-547, Doubleday & Co., Garden City, N.Y. (Arthur I. Holleb, M. D., ed.) 1986.

Forrest, A. P., J. Natl. Cancer Inst., 82:1525, 1990.

Frohman, In: PCR Protocols: A Guide To Methods And Applications, Academic Press, N.Y., 1990.

Fuqua, S. A. W., Wiltschke, C., Castles, C., Wolf, D., and Allred, D. C: A role for estrogen receptor variants in endocrine resistance. Endocrine-Related Cancer, 2:19-25, 1995.

Fuqua, S. A. W., Fitzgerald, S. D., Chamness, G. C., Tandon, A. K., McDonnell, D. P., Nawaz, Z., O'Malley, B. W., McGuire, W. L.: A variant human breast tumor estrogen receptor with constitutive transcriptional activity. Cancer Research, 51: 105-109, 1991.

Furukawa et al., Proc. Natl. Acad. Sci. (USA), 90:1972-1976, 1993.

Fynan et al., Proc. Natl. Acad. Sci. USA, 90:11478-11482, 1993.

Gal et. al., Lab. Invest., 68(1):18, 1993.

Gaugler et al., J. Exper. Med., 179:921-930, 1994.

Gefter et. al., Somatic Cell Genet., 3: 231-236, 1977.

Gelbfish G A, Davidson A I, Kopel S, et al. Relationship of estrogen and progesterone receptors to prognosis in breast cancer. Ann Surg 1988:207(1):75-9.

Giri D D, Dundas A C, Nottingham J F, Underwood J C E. Oestrogen receptors in benign epithelial lesions and intraduct carcinomas of the breast: an immunohistological study. Histopathology 1989;15:575-584.

Goding, In: Monoclonal Antibodies: Principles and Practice, 2d ed., Academic Press, Orlando, Fla., pp. 65-66, and 71-74, 1986.

Going J J, Anderson T J, Battersby S, Macintyre C C A. Proliferative and secretory activity in human breast during natural and artificial cycles. Am J Pathol 1988;130: 193-204.

Gomella et. al., J. Urolology, 158:326-337, 1997.

Greene, G. L., et al.: Sequence and expression of human estrogen receptor complementary DNA. Science, 231: 1150, 1986.

Gross, Cancer Res., 3:326-333, 1943.

Gulbis B and Galand P, "Immunodetection of the p21-ras products in human normal and preneoplastic tissues and solid tumors: a review" Hum Pathol 24(12):1271-1285, 1993.

Ham H J, Shen K L, Yueh K C, Ho L I, Yu J C, Chiu S C, et al. Apoptosis occurs more frequency in intraductal carcinoma than in infiltrating duct carcinoma of human breast cancer and correlates with altered p53 expression: detected by terminal-deoxynucleotidyl-transferase-mediated dUTP-FITC nick end labelling (TUNEL). Histopathology 1997;31:534-539.

Helin H J, Helle M J, Kallioneimi O P, Isona J J. Immunohistochemical determination of estrogen and progesterone receptors in human breast carcinoma: correlation with histopathology and DNA flow cytometry. Cancer 1989;63:1761-1767.

Henderson B E, Ross R, Bernstein L. Estrogens as a cause of human cancer: the Richard and Hindau Rosenthal Foundation Award Lecture. Cancer Res 1988;48:246-253.

Hess et. al., J. Adv. Enzyme Reg., 7:149, 1968.

Hewitt et. al., Br J Cancer, 33 (3) p 241-59, 1976.

Hewitt et al., Br Med J, 2 (6033):477, 1976.

Hitzeman et al., J. Biol. Chem., 255:2073, 1980.

Holland et al., Biochemistry, 17:4900, 1978.

Hollingsworth et al., Int J Cancer, 57(2):198-203, 1994.

Hoon et al., Int J Cancer, 69(5):369-74, 1996.

Hoon et al., J. Immunol., 154:730-737, 1995.

Hoon et al., J. Urol., 150(6):2013-2018, 1993.

Hoon et al., Int. J. Cancer, 43:857-862, 1989.

Horowitz K B, Jackson, T A, Bain D. L., Richer J. K., Takimoto, G. S., Tung L.: Nuclear receptor coactivators and corepressors. Mol Endocrinol, 10: 1167-1177, 1997.

Innis et al., PCR Protocols, Academic Press, Inc., San Diego Calif., 1990.

Inouye et al., Nucleic Acids Res., 13: 3101-3109, 1985.

Irie, In: M. Torisu and T. Yoshida (eds), Basic mechanisms and clinical treatment of tumor metastasis, pp. 371-384, Academic Press, Tokyo, 1985.

Jackson, T. A., Richer J. K., Bain, D. L., Takimoto, G. S., Tung L., Horowitz, K. B.: The partial agonist activity of antagonist occupied steroid receptors is controlled by a novel hinge domain-binding coactivator L7/SPA and the corepressors N-CoR or SMRT. Mol Endcrinol, 11: 693-705, 1997.

Johnson et al., Peptide Turn Mimetics" IN: Biotechnology And Pharmacy, Pezzuto et al., eds., Chapman and Hall, New York, 1993.

Jones, Genetics, 85: 12, 1977.

Joshi K, Smith J A, Perusinghe N, Monoghan P. Cell proliferation in the human mammary epithelium: differential contribution by epithelial and myoepithelial cells. Am J Pathol 1986;124:199-206.

Kahn S A, Rogers M A M, Khurana K K, Meguid M M, Numann P J. Estrogen receptor expression in benign breast epithelium and breast cancer risk. J Natl Cancer Inst 1998;89:37-42.

Kamel O W, Franklin W A, Ringus J C, Meyer J S. Thymidine labeling index and Ki-67 growth fraction in lesions of the breast. American J Pathol 1989;134(1):107-113.

Kang et al., Science, 240:1034-1036, 1988.

Karayiannakis A J, Bastounis E A, Chatzigianni E B, Makri G G, Alexiou D, Karamanakos P. Immunohistochemical detection of oestrogen receptors in ductal carcinoma in situ of the breast. Eur J Surg Oncol 1996;22(6):578-582.

Khatoon et al., Ann. of Neurology, 26, 210-219, 1989.

King et al., J. Biol. Chem., 269, 10210-10218, 1989.

King R J B, Redgrave S, Hayward J L, Millis R R, Rubens R D. The measurement of receptors for oestradiol and progesterone in human breast tumors. In: Steroid receptor assay in human breast tumors King, R J B, editor, Methodological & Clinical Aspects, Alpha Omega. Cardiff, 1979. pp. 55-72.

Kingsman et al., Gene, 7: 141, 1979.

Klein et al., Cancer Res., 20:1561-1572, 1960.

Kohail H M, Elias E G, El-Nowiem S A, et al. A multifactorial analysis of steroid hormone receptors in stages I and II breast cancer. Ann Surg 1985;201(5):611-7.

Kohler and Milstein, Eur. J. Immunol. 6:511-519, 1976.

Kohler and Milstein, Nature, 256:495-497, 1975.

Kohler et al., Methods Enzymol., 178:3, 1989.

Kreier et al., Infection, Resistance and Immunity, Harper & Row, New York, (1991)).

Kripke, J. Natl. Canc. Inst., 53:333-1336, 1974.

Kwoh et al., Proc. Nat. Acad. Sci. USA, 86: 1173, 1989.

Kwon, B. S, J Invest. Dermatol., 100(2 Suppl):134S-140S, 1993.

Kyte and Doolittle, J. Mol. Biol., 157:105-132, 1982.

Lakhani, S. R. The transition from hyperplasia to invasive carcinoma of the breast. J. Path. 187:272-278 (1999).

Leal C B, Schmitt F C, Bento M J, Maia N C, Lopes C S. Ductal carcinoma in situ of the breast. Histologic categorization and its relationship to ploidy and immunohistochemical expression of hormone receptors, p53, and c-erbB-2 protein. Cancer 1995;75:2123-2131.

Lehmann et al., Proc. Nat'l Acad. Sci. USA, 86:9891-9895, 1989.

Lehmann, et al., Cancer Res., 47:841-845, 1987.

Lenert et al., Science, 248:1639-1643, 1990.

Levy et al., Adv. Cancer Res., 24:1-59, 1977.

Liang and Pardee, Science, 257: 967-971, 1992.

Liang et al., Cancer Res., 52:6966-6968, 1992.

Libby A L, O'Connell P, Allred D C. Lobular carcinoma in situ; biological features including loss of heterozygosity. Modem Pathol 1998;11 A112.

Lin and Guidotti, J. Biol. Chem., 264:14408-14414, 1989.

Lishman, S. C. and S. R. Lakhani, Histopathology 1999, 35, 195-200.

Locker A P, Horrocks C, Gilmour A S, Ellis I O, Dowle C S, Elston C W, et al. Flow cytometric and histological analysis of ductal carcinoma in situ of the breast. Br J Surg 1990;77:564-567.

Longacre T A, Bartow S A. A correlative morphologic study of human breast and endometrium in the menstrual cycle. Am J Surg Pathol 1986;10:382-393.

Lowy et al., Cell, 22: 17, 1980.

Madersbacher et al., Cancer Res., 54:5096-5100, 1994.

Marcillac et al., Cancer Res., 52:3901-3907, 1992.

Maryanski et al., Eur. J. Immunol., 124:1627-1634, 1980.

Maryanski et al., Eur. J. Immunol., 12:406-412, 1982.

McCarty K S, Barton T K, Fetter B F, et al. Correlation of estrogen and progesterone receptors with histologic differentiation in mammary carcinoma. Cancer 1980;46:2851-8.

McGuire W L, Pearson O H, Segaloff A. Predicting hormone responsiveness in human breast cancer. In: McGuire W L, Carbone P P, Vollmer E D, editors. Estrogen receptors in breast cancer. New York: Raven Press, 1975, pp. 17-30.

McGuire W L. Prognostic factor for recurrence and survival in human breast cancer. Breast Cancer Res Treat 1987:10:5-9.

McGuire W L. Hormone receptors: their role in predicting prognosis and responses to endocrine therapy. Semin Oncol 1978;5:428-33.

McManus et al., Cancer Res., 36:3476-3481, 1976.

Melcher and Johnson, Mol. Cell Biol., 15:2839-2848, 1995.

Merrifield, Science, 232: 341-347, 1986.

Meyer J S. Cell proliferation in normal human breast ducts, fibroadenomas, and other ductal hyperplasias measured by nuclear labeling with tritiated thymidine. Human Pathol 1977;8:67-81.

Meyer J S. Cell kinetics of histologic variants of in situ breast carcinoma. Breast Cancer Res Treat 1986;7:171-180.

Millis R R. Correlation of hormone receptors with pathological features in human breast cancer. Cancer 1980; 46:2869-71.

Mohsin S K, Hilsenbeck S G, Allred D C. Estrogen receptors and growth control in premalignant breast disease. Modern Pathol 2000(13):28A(#145).

Mok et al., Gynecol. Oncol., 52: 247-252, 1994.

Morton et al., Cancer, 71:3737-3743, 1993.

Mosmann, J. Immunol. Methods, 65:55-63, 1983.

Moul, J. W., Theune, S. M., Change, E. H. Genes Chromo Cancer 5, 109 (1992).

Mulligan, Science, 260:926-932, 1993.

Nagata et al., J. Biol. Chem, 267:12082-12089, 1992.

Nakamura et al., In: Handbook of Experimental Immunology (4th Ed.), Weir, E., Herzenberg, L. A., Blackwell, C., Herzenberg, L. (eds). Vol. 1, Chapter 27, Blackwell Scientific Publ., Oxford, 1987.

Natali et al., Cancer, 59:55-63, 1987.

Nordlund et al., J. Invest. Dermatol, 92:53S-60S, 1989.

Nowell, P. C. Genetic instability in cancer cells: relationship to tumor cell heterogeneity. TUMOR CELL HETEROGENEITY, Owens, A. H., Coffey, D. S., Baylin, S. B. (eds.). New York, Academic Press (1982) pp. 351-365.

O'Connell, P., Fischback, K., Hilsenbeck, S., Fuqua, S. A. W., Clark, G. M., Osborne, C. K., and Allred, D. C.: Loss of heterozygosity at D145S62 and metastatic potential of breast cancer. JNCI, 91:1391-1397, 1999.

O'Connell P, Pekkel V, Fuqua S, Osborne C K, Allred D C: Loss-of-heterozygosity in precursor lesions of breast cancer. JNCI, 90:697-703, 1998.

Oesterreich, S., Weng, C-N, Qiu, M., Hilsenbeck, S. G., Osborne, C. K., Fuqua, S. A. W.: Heat shock protein 27 is correlated with growth and drug resistance in human breast cancer cells. Cancer Research, 53:4443-4448, 1993.

O'Hare et al., Proc. Nat'l Acad. Sci. USA, 78: 1527, 1981.

Ohara et al., Proc. Nat'l Acad. Sci. USA, 86: 5673-5677, 1989.

Onate, S. A., Boonyaratanakornkit, V., Spencer, T. E., Tsai, S. Y., Tsai, M-J., Edwards, D. P., O'Malley, B. W.: The steroid receptor coactivator-1 contains multiple receptor interacting and activation domains that cooperatively enhance the activation function 1(AF1) and AF2 domains of steroid receptors. J. Biol Chem, 273:12101-12108, 1998.

Orita, M et al., Detection of polymorphisms of human DNA by gel electrophoresis as single-strand conformation polymorphisms. Proc. Natl. Acad. Sci. U.S.A. (1989) 86(6):2766-70.

O'Shannessy et al., J. Immun. Meth., 99, 153-161, 1987.

Owens & Haley, J. Biol. Chem., 259:14843-14848, 1987.

Page, D. L. The woman at high risk for breast cancer. Importance of hyperplasia. Surg Clin North Am. 1996 April; 76(2):221-30.

Page, D. L., Dupont, W. D. Anatomic markers of human premalignancy and risk of breast cancer. Cancer. Sep. 15, 1990;66(6 Suppl):1326-35.

Page, D. L., Jensen, R. A. Evaluation and management of high risk and premalignant lesions of the breast. World J. Sur. 1994, 18: 32-38.

Page, D. L. et al. Premalignant and malignant disease of the breast: the roles of the pathologist. Mod. Path. 11(2): 120-128.

Palladino et al., Canc. Res., 47:5074-5079, 1987.

Pallis L, Wilking N, Cedermark B, Rutqvist L E, Skoog L. Receptors for estrogen and progesterone in breast carcinoma in situ. Anticancer Res 1992;12:2113-2115.

Peterson O W, Hoyer P E, van Deurs B. Frequency and distribution of estrogen receptor-positive cells in normal, nonlactating human breast tissue. J Natl Cancer Inst 1986;77:343-349.

Pierrat, B. Heery, D. M., Chambon, P., Losson, R.: A highly conserved region in the hormone-binding domain of the human estrogen receptor functions as an efficient transactivation domain in yeast. Gene, 143: 193-200, 1994.

Pike M C, Spicer D V, Dahmoush L, Press M F. Estrogens, progestins, normal breast cell proliferation, and breast cancer risk. Epidemiologic Reviews 1993;15(1):17-35.

Pinkel, et al., Proc Natl Acad Sci U S A, 83(9):2934-8, 1986.

Poller D N, Silverstein M J, Galea M, Locker A P, Elston C W, Blarney R W, et al. Ductal carcinoma in situ of the breast: a proposal for a new simplified histological classification association between cellular proliferation and c-erbB-2 protein expression. Modem Pathol 1994;7:257-262.

Poller D N, Snead D R J, Roberts E C, Galea M, Bell J A, Gilmour A, et al. Oestrogen receptor expression in ductal carcinoma in situ of the breast: relationship to flow cytometric analysis of DNA and expression of the c-erbB-2 oncoprotein. Br J Cancer 1993;68:156-161.

Potten C S, Watson R J, Williams G T, Tickle S, Roberts S A, Harris M, et al. The effect of age and menstrual cycle upon proliferative activity of the normal human breast. Br J Cancer 1988;58:163-170.

Potter & Haley, Meth. in Enzymol., 91, 613-633, 1983.

Prehn, et al., J. Natl. Canc. Inst., 18:769-778, 1957.

Prosser J, Hilsenbeck S G, Fuqua S A W, O'Connell P, Osborne C K, Allred DC. Cell turnover (proliferation and apoptosis) in normal epithelium and premalignant lesions in the same breast. Lab Invest 1997;76:24A (119).

Querzoli P, Albonico G, Ferretti S, Rinaldi R, Beccati D, Corcione S, et al. Modulation of biomarkers in minimal breast carcinoma: a model for human breast carcinoma progression. Cancer 1998;83(1):89-97.

Remington's Pharmaceutical Sciences, 15th ed., pp. 1035-1038 and 1570-1580; 624-652.

Ricketts D, Tumbull L, Tyall G, Bakhshi R, Rawson N S B, Gazet J C, et al. Estrogen and progesterone receptors in the normal female breast. Cancer Res 1991;51:1817-1822.

Robbins et al., Cancer Res, 54(12):3124-6, 1994.

Robzyk and Kassir, "A simple and highly efficient procedure for rescuing autonomous plasmids from yeast," Nucl. Acids Res., 20:3790, 1992.

Roger, P. et al., Human Path., 31(5):593-600.

Rubinstein et al., J. Natl. Cancer Inst., 82:1113-1120, 1990.

Rudas M, Neumayer R, Gnant M, Mittelbock M, Jakesz R, Reiner A. p53 protein expression, cell proliferation and steroid hormone receptros in ductal and lobular in situ carcinomas of the breast. Eur J Cancer 1997;33(1):39-44.

Russo J, Calaf G R L, Russo I H. Influence of age and gland topography on cell kinetics of normal breast tissue. J Natl Cancer Inst 1987;78:413-418.

Sager et al., FASEB J., 7: 964-970, 1993.

Sambrook, Fritsch, Maniatis, In: *Molecular Cloning: A Laboratory Manual*, Vol. 1, Cold Spring Harbor Laboratory Press, Cold Spring Harbor, N.Y., Ch. 7,7.19-17.29, 1989.

Santerre et al., Gene, 30:147, 1984.

Sarantou et al., Cancer Res, 57(7):1371-6, 1997.

Sauter E R, Ross E, Daly M, Klein-Szanto A, Engstrom P F, Sorling A, Malick J, Ehya H. Nipple aspirate fluid: a promising non-invasive method to identify cellular markers of breast cancer risk. Br J Cancer 1997;76(4): 494-501.

Sasso et al, J. Immunol., 142:2778-2783, 1989.

Schmitt F C. Multistep progression from an oestorgen-dependent growth towards an autonomous growth in breast cancinogenesis. European J Cancer 1995;31 A(12):2049-2052.

Serrano et al., Nature, 366:704-707, 1993.

Serrano et al., Science, 267:249-252, 1995.

Shorki et al., J. Immunol., 146:936-940, 1991.

Shiau, A. K., Bartad, D., Loria, P. M., Cheng, L., Kushner, P. J., Agard, D. A., Greene, G. L.: The structural basis of estrogen receptor/coactivator recognition and the antagonism of this interaction by tamoxifen. Cell, 85:927-937, 1998.

Shousha S, Coady A T, Stamp T, James J R, Alaghband-Zadeh J. Oestrogen receptors in mucinous carcinoma of the breast: an immunohistological study using paraffin wax sections. J Clin Pathol 1989;42:902-5.

Shousha S, Stamp T, James JR, Alaghband-Zadeh J. Immunohistological study of oestrogen receptors in breast carcinomas that are biochemically receptor negative. J Clin Pathol 1990;43:239-42.

Silvermann et al., J. Clin. Invest., 96:417-426, 1995.

Smith and Johnson, "Single-step purification of polypeptides expressed in *Escherichia coli* as fusions with glutathione S-transferase," Gene, 67:31-40, 1988.

Stewart and Young, Solid Phase Peptide Synthesis, 2d. ed., Pierce Chemical Co., 1984.

Stinchcomb et al., Nature, 282: 39, 1979.

Stoll, B. A. Premalignant breast lesions: role for biological markers in predicting progression to cancer. Eur. J. Cancer 35(5): 693-697.

Sun and Cohen, Gene, 137:127-132, 1993.

Szybalska et al., Proc. Nat'l Acad. Sci. USA, 48: 2026, 1962.

Talmadge et al., Nature, 307:37-40, 1984.

Tam et al., J. Am. Chem. Soc., 105:6442, 1983.

Tang et al., Nature, 356:152-154, 1992.

Traversari et al., Immunogenetics, 35(3):145-52, 1992.

Traversari et al, J Exp Med., 176(5):1453-7, 1992.

Tremblay, G. B., Tremblay, A., Labrie, F., Giguere, V.: Ligand-independent activation of the estrogen receptors alpha and beta by mutations of a conserved tyrosine can be abolished by antiestrogens. Cancer Research, 58: 877-881, 1998.

Tschemper et al., Gene, 10: 157, 1980.

Tsuchida et al., J. Natl. Cancer Inst., 78:45-54, 1987a.

Tsuchida et al., J. Natl. Cancer Inst., 78:55-60, 1987b.

Ulmer et al., Science, 259:1745-1749, 1993.

Van den Eynde, et al., Biochem Soc Trans, 23(3):681-6, 1995.

Van den Eynde et al., J Exp Med, 182(3):689-98, 1995.

Van Der Bruggen, Traversari, Chomez, Lurquin, De Plaen, Van Den Eynde, Knuth, Boon, "A gene encoding an antigen recognized by cytolytic T lymphocytes on a human melanoma," Science, 254:1643-1647, 1991.

Van Agthoven, T., Timmermans, M., Foekens, J. A., Dorssers, L. C., Henzen-Logmans, S. C.: Differential expression of estrogen, progesterone, and epidermal growth factor receptors in normal, benign, and malignant human breast tissue using dual staining immunohistochemistry. Am J Pathol., 144: 1238-1246, 1994.

Van Pel et al., J. Exp. Med., 157:1992-2001, 1983.

Vijayasardahi et al., J. Experimental Medicine, 171(4): 1375-1380, 1990.

Visscher D W, Gingrich D S, Buckley J, Tabaczka P, Crissman J D. Cell cycle analysis of normal, atrophic, and hyperplastic breast epithelium using two-color multiparametric flow cytometry. Analytical Cellular Pathol 1996;12(2):115-124.

Visualization of Nucleic Acids" Gerad Morell Ed., CRC publ., 1995.

Voegel, J. J., Heine, M. J. S., Zechel, C. Chambon, P.O., Gronemeyer, H.: TIF-2, a 160 kDa transcriptional mediator for the ligand-dependent activation function AF-2 of nuclear receptors EMBO J., 15:101, 1996.

Vogelstein, B. and Kinzler, K. W.: The multistep nature of cancer. Trends Genet, 9:138-141, 1993.

Wagner et al., Science, 260:1510-1513, 1993.

Walker et al., Proc. Nat'l Acad. Sci. USA, 89:392-396 1992.

Wang et al., In: Animal Cell Technology: Basic & Applied Aspects, S. Kaminogawa et al., (eds), vol. 5, pp 463-469, Kluwer Academic Publishers, Netherlands, 1993.

Watson et al., Cancer Res., 54: 4598-4602, 1994.

Weitzel and Patel, GATA, 11 (5-6) 165-170, 1994.

Weitzel et al., Genomics, 14:309-319, 1992.

Welsh et al., Nucleic Acids Res., 20: 4965-4970, 1992.

Whitton et al., J. Virol., 67:(1)348-352,1993.

Wigler et al., Cell, 11: 223, 1977.

Wigler et al., Proc. Nat'l Acad. Sci. USA, 77: 3567, 1980.

Williams M R, Todd J H, Ellis I O, et al. Oestrogen receptors in primary and advanced breast cancer: an 8 year review of 704 cases. Br J Cancer 1987;55:67-73.

Wong et al., Int. J. Oncol., 3: 13-17, 1993.

Wu et al., Genomics, 4:560, 1989

Yamaguchi et al., Br. J. Cancer, 60:382-384, 1989.

Yoshimura et al., Cancer, 73:2745-2752, 1994.

Zhang, Q-X, Borg, A., Wolf, D. M., Oesterreich, S., Fuqua, S. A. W.: An estrogen receptor mutant with strong hormone-independent activity from a metastatic breast cancer. Cancer Research 57:1244-1249, 1997.

Zafrani B, Leroyer A, Fourquet A, Laurent M, Torphilme D, Validire P, et al. Mammographically detected ductal in situ carcinoma of the breast analyzed with a new classification. A study of 127 cases: correlation with estrogen and progesterone receptors, p53, and c-erbB-2 proteins, and proliferative activity. Sem Diagnostic Pathol 1994;11:208-214.

One skilled in the art readily appreciates that the patent invention is well adapted to carry out the objectives and obtain the ends and advantages mentioned as well as those inherent therein. Mutations, kits, sequences, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. An isolated nucleic acid molecule comprising SEQ ID NO:34.

2. The nucleic acid molecule of claim 1, wherein said molecule is between 20 and 100 nucleotides.

3. The nucleic acid molecule of claim 1, wherein said molecule is from 20 to 30 nucleotides in length.

4. The nucleic acid molecule of claim 1, wherein said molecule is up to 1-2 kilobases in length.

5. The nucleic acid molecule of claim 1 wherein said nucleic acid sequence is a DNA.

6. The nucleic acid molecule of claim 1 wherein said nucleic acid sequence is a RNA.

7. The nucleic acid molecule of claim 1, wherein said molecule is about 21 nucleotides in length.

8. The nucleic acid molecule of claim 1, wherein said molecule is about 22 nucleotides in length.

9. The nucleic acid molecule of claim 1, wherein said molecule is about 23 nucleotides in length.

10. An isolated nucleic acid molecule that has 90% or more identity to the full length of SEQ ID NO:6 and comprises SEQ ID NO:34, or the complement thereof.

* * * * *